US011780906B2

(12) United States Patent
Grossman et al.

(10) Patent No.: US 11,780,906 B2
(45) Date of Patent: *Oct. 10, 2023

(54) COMPOSITIONS AND METHODS FOR THE TREATMENT OF IMMUNODEFICIENCY

(71) Applicant: ADMA Biologics, Inc., Ramsey, NJ (US)

(72) Inventors: Adam S. Grossman, Saddle River, NJ (US); James Mond, Silver Spring, MD (US); Jerrold B. Grossman, Saddle River, NJ (US); Dov A. Goldstein, New York, NY (US)

(73) Assignee: ADMA BIOMANUFACTURING, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/750,470

(22) Filed: May 23, 2022

(65) Prior Publication Data

US 2022/0403008 A1 Dec. 22, 2022

Related U.S. Application Data

(63) Continuation of application No. 16/901,993, filed on Jun. 15, 2020, now Pat. No. 11,339,206, which is a continuation of application No. 15/978,692, filed on May 14, 2018, now Pat. No. 10,683,343, which is a continuation of application No. 15/811,486, filed on Nov. 13, 2017, now Pat. No. 9,969,793, which is a continuation of application No. 14/592,727, filed on Jan. 8, 2015, now Pat. No. 9,815,886.

(60) Provisional application No. 62/069,589, filed on Oct. 28, 2014.

(51) Int. Cl.
| | | |
|---|---|---|
| *A61K 39/395* | (2006.01) | |
| *C07K 16/06* | (2006.01) | |
| *A61K 39/42* | (2006.01) | |
| *C07K 16/08* | (2006.01) | |
| *C07K 16/10* | (2006.01) | |
| *A61K 39/155* | (2006.01) | |
| *A61K 45/06* | (2006.01) | |
| *G01N 33/68* | (2006.01) | |
| *C07K 16/12* | (2006.01) | |
| *A61K 39/00* | (2006.01) | |

(52) U.S. Cl.
CPC ............ *C07K 16/06* (2013.01); *A61K 39/155* (2013.01); *A61K 39/39516* (2013.01); *A61K 39/42* (2013.01); *A61K 45/06* (2013.01); *C07K 16/08* (2013.01); *C07K 16/10* (2013.01); *C07K 16/1009* (2013.01); *C07K 16/1027* (2013.01); *C07K 16/1203* (2013.01); *C07K 16/1232* (2013.01); *C07K 16/1242* (2013.01); *C07K 16/1271* (2013.01); *C07K 16/1275* (2013.01); *C07K 16/1282* (2013.01); *C07K 16/1285* (2013.01); *C07K 16/1289* (2013.01); *G01N 33/6854* (2013.01); *A61K 2039/507* (2013.01); *C07K 2317/10* (2013.01); *C07K 2317/21* (2013.01); *C07K 2317/31* (2013.01); *C07K 2317/76* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,021,540 | A | 5/1977 | Pollack et al. |
| 4,174,388 | A | 11/1979 | McAleer et al. |
| 4,256,631 | A | 3/1981 | Yokoo et al. |
| 4,305,870 | A | 12/1981 | Liu et al. |
| 4,346,073 | A | 8/1982 | Aronson et al. |
| 4,356,170 | A | 10/1982 | Jennings et al. |
| 4,402,939 | A | 9/1983 | Fournier |
| 4,482,483 | A | 11/1984 | Curry et al. |
| 4,587,121 | A | 5/1986 | Collins et al. |
| 4,617,379 | A | 10/1986 | Dobkin et al. |
| 4,659,563 | A | 4/1987 | Dobkin |
| 4,665,159 | A | 5/1987 | Dobkin |
| 4,717,564 | A | 1/1988 | Dobkin |
| 4,717,766 | A | 1/1988 | Dobkin |
| 4,801,450 | A | 1/1989 | Collins et al. |

(Continued)

FOREIGN PATENT DOCUMENTS

| | | |
|---|---|---|
| AU | 692678 | 3/1996 |
| AU | 2002368447 | 6/2004 |

(Continued)

OTHER PUBLICATIONS

Groothuis et al., Antimicrobial agents and chemotherapy vol. 35, pp. 1469-1473 (Year: 1991).*

(Continued)

*Primary Examiner* — Shanon A. Foley
*Assistant Examiner* — Myron G Hill
(74) *Attorney, Agent, or Firm* — Casimir Jones SC; Tyler Sisk

(57) ABSTRACT

The present invention relates to compositions and methods for the treatment of immunodeficiency (e.g., primary immunodeficiency disease). In particular, the invention provides human plasma immunoglobulin compositions containing select antibody titers specific for a plurality of respiratory pathogens, methods of identifying human donors and donor samples for use in the compositions, methods of manufacturing the compositions, and methods of utilizing the compositions (e.g., for prophylactic administration and/or therapeutic treatment (e.g., passive immunization (e.g., immuneprophylaxis))).

20 Claims, 14 Drawing Sheets

(56) References Cited

U.S. PATENT DOCUMENTS

| | | | |
|---|---|---|---|
| 4,863,730 | A | 9/1989 | Karpas |
| 5,360,897 | A | 11/1994 | Anderson et al. |
| 5,412,077 | A | 5/1995 | Siber et al. |
| 5,455,032 | A | 10/1995 | Kenny et al. |
| 5,505,945 | A | 4/1996 | Gristina |
| 5,530,102 | A | 6/1996 | Gristina et al. |
| 5,582,827 | A | 12/1996 | Siber et al. |
| 5,614,382 | A | 3/1997 | Metcalf |
| 5,679,768 | A | 10/1997 | Briles et al. |
| 5,728,387 | A | 3/1998 | Briles et al. |
| 5,804,193 | A | 9/1998 | Briles et al. |
| 5,817,312 | A | 10/1998 | Gristina et al. |
| 5,847,112 | A | 12/1998 | Kniskern et al. |
| 5,891,438 | A | 4/1999 | Silverman |
| 5,965,141 | A | 10/1999 | Briles et al. |
| 6,224,880 | B1 | 5/2001 | Chan et al. |
| 6,372,216 | B1 | 4/2002 | Piazza |
| 6,692,739 | B1 | 2/2004 | Patti et al. |
| 6,929,930 | B2 | 8/2005 | Choi et al. |
| 6,962,700 | B1 | 11/2005 | Pollack |
| 6,984,492 | B2 | 1/2006 | Betez et al. |
| 7,045,131 | B2 | 5/2006 | Patti et al. |
| 7,488,486 | B2 | 2/2009 | Shimoni et al. |
| 7,597,891 | B2 | 10/2009 | Simon |
| 8,252,546 | B2 | 8/2012 | Briles et al. |
| 8,354,249 | B2 | 1/2013 | Nur et al. |
| 9,107,906 | B1 * | 8/2015 | Grossman .......... C07K 16/1275 |
| 9,714,283 | B2 * | 7/2017 | Grossman .......... C07K 16/1203 |
| 9,815,886 | B2 * | 11/2017 | Grossman .............. A61K 39/42 |
| 9,969,793 | B2 * | 5/2018 | Grossman ............ A61K 39/155 |
| 10,683,343 | B2 * | 6/2020 | Grossman .............. C07K 16/10 |
| 11,339,206 | B2 * | 5/2022 | Grossman .............. A61K 45/06 |
| 2002/0051788 | A1 | 5/2002 | Pozsgay |
| 2002/0159997 | A1 | 10/2002 | Patti et al. |
| 2003/0105307 | A1 | 6/2003 | Sampson et al. |
| 2003/0118591 | A1 | 6/2003 | Levy |
| 2003/0133929 | A1 | 7/2003 | Cham |
| 2003/0147922 | A1 | 8/2003 | Capiau et al. |
| 2003/0162260 | A1 | 8/2003 | Minion et al. |
| 2004/0052804 | A1 | 3/2004 | Arumugham et al. |
| 2004/0228879 | A1 | 11/2004 | Deschamps et al. |
| 2005/0031646 | A1 | 2/2005 | Capiau et al. |
| 2005/0053605 | A1 | 3/2005 | Betz et al. |
| 2005/0287146 | A1 | 12/2005 | Patti et al. |
| 2006/0002961 | A1 | 1/2006 | Capiau et al. |
| 2006/0093626 | A1 | 5/2006 | Capiau et al. |
| 2006/0110407 | A1 | 5/2006 | Stopera et al. |
| 2006/0198848 | A1 | 9/2006 | Betz et al. |
| 2006/0222651 | A1 | 10/2006 | Patti et al. |
| 2007/0037170 | A1 | 2/2007 | Nur et al. |
| 2007/0154492 | A1 | 7/2007 | Michon et al. |
| 2007/0231344 | A1 | 10/2007 | Leadbetter et al. |
| 2007/0249550 | A1 | 10/2007 | Sitkovsky |
| 2009/0004218 | A1 | 1/2009 | Hacohen et al. |
| 2009/0232798 | A1 | 9/2009 | Betz et al. |
| 2009/0269359 | A1 | 10/2009 | Scuderi et al. |
| 2010/0040601 | A1 | 2/2010 | Cantin et al. |
| 2010/0074922 | A1 | 3/2010 | Biemans |
| 2010/0143394 | A1 | 6/2010 | Kasmi et al. |
| 2010/0266625 | A1 | 10/2010 | Tai et al. |
| 2011/0020386 | A1 | 1/2011 | Gierahn et al. |
| 2011/0059085 | A1 | 3/2011 | Kim |
| 2012/0121578 | A1 | 5/2012 | Block |
| 2013/0108619 | A1 | 5/2013 | Melamed |

FOREIGN PATENT DOCUMENTS

| | | |
|---|---|---|
| CA | 2472818 | 12/2005 |
| CA | 2749367 | 7/2010 |
| CN | 1241937 | 1/2000 |
| CN | 1899609 | 1/2007 |
| CN | 101024079 | 8/2007 |
| CN | 101130071 | 2/2008 |
| CN | 101374548 | 2/2009 |
| CN | 101590224 | 12/2009 |
| CN | 101785857 | 7/2010 |
| CN | 102068690 | 5/2011 |
| CO | 5210947 | 10/2002 |
| EP | 0035429 | 9/1981 |
| EP | 0161188 | 11/1985 |
| EP | 0168322 | 1/1986 |
| EP | 0186576 | 7/1986 |
| EP | 0208375 | 1/1987 |
| EP | 0378881 | 7/1990 |
| EP | 0383184 | 8/1990 |
| EP | 0399001 | 11/1990 |
| EP | 0427347 | 5/1991 |
| EP | 0449856 | 10/1991 |
| EP | 0471177 | 2/1992 |
| EP | 0477508 | 4/1992 |
| EP | 0497524 | 8/1992 |
| EP | 0497525 | 8/1992 |
| EP | 0571538 | 12/1993 |
| EP | 0622081 | 11/1994 |
| EP | 0625910 | 11/1994 |
| EP | 0720485 | 7/1996 |
| EP | 0778781 | 6/1997 |
| EP | 0831901 | 4/1998 |
| EP | 0848011 | 6/1998 |
| EP | 0877624 | 11/1998 |
| EP | 0894008 | 2/1999 |
| EP | 0969873 | 1/2000 |
| EP | 0971945 | 1/2000 |
| EP | 0977588 | 2/2000 |
| EP | 0983087 | 3/2000 |
| EP | 1015027 | 7/2000 |
| EP | 1019437 | 7/2000 |
| EP | 1035137 | 9/2000 |
| EP | 1076662 | 2/2001 |
| EP | 1109576 | 6/2001 |
| EP | 1124576 | 8/2001 |
| EP | 1137789 | 10/2001 |
| EP | 1162998 | 12/2001 |
| EP | 1171159 | 1/2002 |
| EP | 1296715 | 4/2003 |
| EP | 1317279 | 6/2003 |
| EP | 1501542 | 2/2005 |
| EP | 1558280 | 8/2005 |
| EP | 1590373 | 11/2005 |
| EP | 1638601 | 3/2006 |
| EP | 1651261 | 5/2006 |
| EP | 1704167 | 9/2006 |
| EP | 1776962 | 4/2007 |
| EP | 1791860 | 6/2007 |
| EP | 1838345 | 10/2007 |
| EP | 1868645 | 12/2007 |
| EP | 1880735 | 1/2008 |
| EP | 1928418 | 6/2008 |
| EP | 1962899 | 9/2008 |
| EP | 2167531 | 3/2010 |
| EP | 2180901 | 5/2010 |
| EP | 2277535 | 1/2011 |
| JP | 2010260849 | 11/2010 |
| JP | 2011057713 | 3/2011 |
| KR | 20110068831 | 6/2011 |
| WO | WO 91/01146 | 2/1991 |
| WO | WO 91/12819 | 9/1991 |
| WO | WO 93/15758 | 8/1993 |
| WO | WO 94/04195 | 3/1994 |
| WO | WO 95/13294 | 5/1995 |
| WO | WO 96/21465 | 7/1996 |
| WO | WO 96/40225 | 12/1996 |
| WO | WO 97/20940 | 6/1997 |
| WO | WO 98/18931 | 5/1998 |
| WO | WO 98/33521 | 8/1998 |
| WO | WO 98/39450 | 9/1998 |
| WO | WO 99/03884 | 1/1999 |
| WO | WO 99/15205 | 4/1999 |
| WO | WO 99/40936 | 8/1999 |
| WO | WO 99/47168 | 9/1999 |
| WO | WO 00/12132 | 3/2000 |
| WO | WO 01/72337 | 3/2000 |
| WO | WO 00/56360 | 9/2000 |
| WO | WO 00/61761 | 10/2000 |

(56) References Cited

FOREIGN PATENT DOCUMENTS

| WO | WO 00/62801 | 10/2000 |
|---|---|---|
| WO | WO 00/63385 | 10/2000 |
| WO | WO 01/96368 | 12/2001 |
| WO | WO 02/40518 | 5/2002 |
| WO | WO 02/056909 | 7/2002 |
| WO | WO 03/040170 | 5/2003 |
| WO | WO 03/051392 | 6/2003 |
| WO | WO 2004/064864 | 8/2004 |
| WO | WO 2004/097000 | 11/2004 |
| WO | WO 2005/058940 | 6/2005 |
| WO | WO 2005/065382 | 7/2005 |
| WO | WO 2005/108580 | 11/2005 |
| WO | WO 2005/120563 | 12/2005 |
| WO | WO 2006/027685 | 3/2006 |
| WO | WO 2006/065137 | 6/2006 |
| WO | WO 2006/084467 | 8/2006 |
| WO | WO 2007/068907 | 6/2007 |
| WO | WO 2007/071711 | 6/2007 |
| WO | WO 2007/109129 | 9/2007 |
| WO | WO 2007/113598 | 10/2007 |
| WO | WO 2007/116028 | 10/2007 |
| WO | WO 2007/116322 | 10/2007 |
| WO | WO 2007/116409 | 10/2007 |
| WO | WO 2008/021076 | 2/2008 |
| WO | WO 2008/081014 | 7/2008 |
| WO | WO 2008/081022 | 7/2008 |
| WO | WO 2008/102173 | 8/2008 |
| WO | WO 2008/119358 | 10/2008 |
| WO | WO 2008/157590 | 12/2008 |
| WO | WO 2009/000826 | 12/2008 |
| WO | WO 2009/016515 | 2/2009 |
| WO | WO 2009/076158 | 6/2009 |
| WO | WO 2009/106085 | 9/2009 |
| WO | WO 2009/143413 | 11/2009 |
| WO | WO 2010/015701 | 2/2010 |
| WO | WO 2010/064243 | 6/2010 |
| WO | WO 2010/109324 | 9/2010 |
| WO | WO 2010/109325 | 9/2010 |
| WO | WO 2010/141312 | 12/2010 |
| WO | WO 2010/150242 | 12/2010 |
| WO | WO 2011/031893 | 3/2011 |
| WO | WO 2011/067758 | 6/2011 |
| WO | WO 2011/080595 | 7/2011 |
| WO | WO 2011/103588 | 8/2011 |
| WO | WO 2011/110241 | 9/2011 |
| WO | WO 2011/110531 | 9/2011 |

OTHER PUBLICATIONS

Adler et al., Findings and conclusions from CMV hyperimmune globulin treatment trials. Journal of Clinical Virology,(2009). 46:S54-S57.
Aschermann et al., The other side of immunoglobulin G: suppressor of inflammation. Clinical & Experimental Immunology, (2010). 160(2), 161-167.
Ben-Nathan et al., Using high titer West Nile intravenous immunoglobulin from selected Israeli donors for treatment of West Nile virus infection. BMC infectious diseases, (2009). 9(1), 18.
Bhakdi et al., Human hyperimmune globulin protects against the cytotoxic action of staphylococcal alpha-toxin in vitro and in vivo. Infection and immunity, (1989). 57(10), 3214-3220.
Casadevall et al., Passive antibody therapy for infectious diseases. Nature Reviews Microbiology, (2004). 2(9), 695-703.
Casadevall et al., Serum therapy revisited: animal models of infection and development of passive antibody therapy. Antimicrobial agents and chemotherapy, (1994). 38(8), 1695-1702.
Cohn et al., Preparation and properties of serum and plasma proteins; a system for the separation into fractions of the protein and lipoprotein components of biological tissues and fluids, J Am Chem Soc, 62, 459-475 (1946).
Cortez et al., Immune-globulin prophylaxis of respiratory syncytial virus infection in patients undergoing stem-cell transplantation. The Journal of infectious diseases, (2002). 186(6), 834-838.
Corthesy, Recombinant secretory IgA for immune intervention against mucosal pathogens, Biochem. Soc. Trans. 1997; 25:471-475.
Crottet et al., Expression, purification and biochemical characterization of recombinant murine secretory component: a novel tool in mucosal immunology, Biochem. J. 1999; 341:299-306.
De Hennezel, et al., Effective combination therapy for invasive pneumococcal pneumonia with ampicillin and intravenous immunoglobulins in a mouse model. Antimicrobial agents and chemotherapy, (2001). 45(1), 316-318.
Devincenzo et al., Respiratory syncytial virus immune globulin treatment of lower respiratory tract infection in pediatric patients undergoing bone marrow transplantation—a compassionate use experience, Bone Marrow Transplantation, vol. 25, No. 2, Jan. 1, 2000 (2090-91-91), pp. 161-165.
Dorner et al., At what stage should virus inactivation be carried out?, Dev Biol Stand 1993 vol. 81, pp. 137-143.
European Search Report of co-pending European patent application No. 15190963.7 dated May 3, 2016.
Falsey et al., A Summary of the Study of a Polyclonal Human IVIG with A Standardized High-Levels of RSV Neutralizing Antibodies, IDSA International Conference, Aug. 21, 2013.
Falsey et al., Acute respiratory tract infection in daycare centers for older persons, J Am Geriatr Soc. 1995;43:30-36.
Falsey et al., Human metapneumovirus infections in young and elderly adults, J Infect Dis. 2003;187:785-790.
Falsey et al., The "common cold" in frail older persons: impact of rhinovirus and coronavirus in a senior daycare center, J Am Geriatr Soc. 1997;45:706-711.
Falsey et al., Viral respiratory infections in the institutionalized elderly: clinical and epidemiologic findings, J Am Geriatr Soc. 1992;40:115-119.
Gelfand, Clinical uses of intravenous immunoglobulin continue to expand, Medscape Allergy & Immunology, 2004, pp. 1-4.
Hamill et al., IgG Antibody Reactive with Five Serotypes of *Streptococcus pneumoniae* in Commercial Intravenous Immunoglobulin Preparations, The Journal of Infectious Diseases, vol. 166, No. 1 (Jul. 1992), pp. 38-42.
Hemming et al., Hyperimmune globulins in prevention and treatment of respiratory syncytial virus infections. Clinical microbiology reviews, (1995). 8(1), 22-33.
Hügler et al., Prevention of postherpetic neuralgia with varicella-zoster hyperimmune globulin. European journal of pain, (2002). 6(6), 435-445.
Ishizaka et al., Successful intravenous immunoglobulin therapy for recurrent pneumococcal otitis media in young children. European journal of pediatrics, (1994). 153(3), 174-178.
Jones et al., Controlled trial of Pseudomonas immunoglobulin and vaccine in burn patients, Lancet. Dec. 13, 1980;2(8207):1263-5.
Keller and Stiehm, Passive Immunity in Prevention and Treatment of Infectious Diseases, Clin. Microbiol. Rev. 2000, 13(4): pp. 602-614.
Kudoyarova-Zubavichene et al., Preparation and use of hyperimmune serum for prophylaxis and therapy of Ebola virus infections. Journal of Infectious Diseases, (1999). 179(Supplement 1), S218-S223.
Lake,Do we really need long-term hepatitis B hyperimmune globulin? What are the alternatives?. Liver Transplantation, (2008). 14(S2), S23-S26.
Lejtenyi et al., Consistency of protective antibody levels across lots of intravenous immunoglobulin preparations. Journal of Allergy and Clinical Immunology, (2008). 121(1), 254-255.
Lullau et al., Antigen binding properties of purified immunoglobulin A and reconstituted secretory immunoglobulin A antibodies, J. Biol. Chem. 1996; 271:16300-16309.
Meijvis et al., Therapy in pneumonia: what is beyond antibiotics?. Arterial and venous thrombosis: more in common than previously thought, 21. (2011).
Mofenson et al.,Intravenous immune globulin for the prevention of bacterial infections in children with symptomatic human immunodeficiency virus infection. The National Institute of Child Health

(56) References Cited

OTHER PUBLICATIONS and Human Developments Intravenous Immunoglobulin Study Group, The New England Journal of Medicine, Jul. 11, 1991, vol. 325, No. 2, pp. 73-80.

Murphy et al., Dissociation between serum neutralizing and glycoprotein antibody responses of infants and children who received inactivated respiratory syncytial virus vaccine. Journal of clinical microbiology, (1986). 24(2), 197-202.

Nation et al., Tetanus—the use of human hyperimmune globulin in treatment. California medicine, (1963). 98(6), 305.

Navarrete-Navarro et al., Improved serological response to human diploid cell rabies vaccine when given simultaneously with antirabies hyperimmune globulin. Archives of medical research, (1999). 30(4), 332-337.

Nimmerjahn, F., & Ravetch, J. V., Anti-inflammatory actions of intravenous immunoglobulin. Annu. Rev. Immunol., (2008). 26, 513-533.

Oncely, J. L. et al., The Separation of the Antibodies, Isoagglutinins, Prothrombin, Plasminogen and B1-Lipoprotein into subfractions of human plasma, J. Am Chem Soc. 71:541-550 (1949).

Orange et al., Primary Immunodeficiency Committee of the American Academy of Allergy, Asthma and Immunology. Use of intravenous immunoglobulin in human disease: a review of evidence by members of the Primary Immunodeficiency Committee of the American Academy of Allergy, Asthma and Immunology. J Allergy Clin Immunol, (2006) 117(4 Suppl), S525-S553.

Ottolini et al., Effectiveness of RSVIG prophylaxis and therapy of respiratory syncytial virus in an immunosuppressed animal model. Bone marrow transplantation, (1999). 24(1), 41-45.

Ramakrishna et al., Passively administered pooled human immunoglobulins exert IL-10 dependent anti-inflammatory effects that protect against fatal HSV encephalitis, Plos Pathogens. 2011. 7:6:e1002071.

Roe et al., Passive immunization of mice against Klebsiella aerogenes. British journal of experimental pathology,(1986). 67(1), 25-32.

Shurin et al., Bacterial polysaccharide immune globulin for prophylaxis of acute otitis media in high-risk children, The Journal of Pediatrics, Nov. 1993, pp. 801-810.

Siber et al., Protective activity of a human respiratory syncytial virus immune globulin prepared from donors screened by microneutralization assay. Journal of Infectious Diseases, (1992). 165(3), 456-463.

Siber et al., Comparison of antibody concentrations and protective activity of respiratory syncytial virus A immune globulin and conventional immune globulin, Journal of Infectious Diseases. JID, University of Chicago Press, Chicago, IL, vol. 169, No. 6, Jan. 1, 1994 (1994-81-81), pp. 1368-1373.

Siber et al., Preparation of human hyperimmune globulin to Haemophilus influenzae b, *Streptococcus pneumoniae*, and Neisseria meningitidis. Infection and immunity, (1984). 45(1), 248-254.

Simoes et al., Respiratory syncytial virus-enriched globulin for the prevention of acute otitis media in high-risk children, Journal of Pediatrics v 129, No. 2, pp. 214-219, 1996.

Stiehm, Standard and special human immune serum globulins as therapeutic agents, Pediatrics, (1979)vol. 63, No. 1, 301-319.

Stott et al, Respiratory syncytial virus. Brief review, Archives of Virology, 84:1-52 (1985).

Teschner et al., A new liquid, intravenous immunoglobulin product (IGIV 10%) highly purified by a state-of-the-art process, Vox Sang. Jan. 2007;92(1):42-55.

US FDA standards for immune globulin preparation (37 CFR §§640.100; 640.101; 640.102; 640.103; and 640.104, Apr. 1, 2013).

World Health Organization. Pneumococcal conjugate vaccine for childhood immunization, WHO position paper. Wkly Epidemiol Rec, (2007). 82(12), 93-104.

World Intellectual Property Organization, Patent Landscape Report on Vaccines for Selected Infectious Diseases, 2012.

Wu et al., Immunoprophylaxis of RSV Infection: Advancing from RSV-IGIV to Palivizumab and Motavizumab, Curr Topics Microbiol Immunol. vol. 317, pp. 103-123, 2008.

Zaia et al., A practical method for preparation of varicella-zoster immune globulin, The Journal of Infectious Diseases, vol. 137, No. 5, 601-604 (1978).

\* cited by examiner

Whole Blood Analysis Data, Day -3

Whole Blood Analysis Data, Days 4 and 10 p.i.

II-82 White Blood Cells Day 4p.i.

II-82 White Blood Cells Day 10p.i.

II-82 Lymphocytes Day 4p.i.

II-82 Lymphocytes Day 10p.i.

limit of detection 2 log10 PFU/g

COMPOSITIONS AND METHODS FOR THE TREATMENT OF IMMUNODEFICIENCY

This application is a continuation of U.S. application Ser. No. 16/901,993, filed Jun. 15, 2020, now allowed, which is a continuation of U.S. application Ser. No. 15/978,692, filed May 14, 2018, now allowed, which is a continuation of U.S. application Ser. No. 15/811,486, filed Nov. 13, 2017, now U.S. Pat. No. 9,969,793, which is a continuation of U.S. application Ser. No. 14/592,727, filed Jan. 8, 2015, now U.S. Pat. No. 9,815,886, which claims the benefit of U.S. Provisional Application No. 62/069,589, filed Oct. 28, 2014, each of which is incorporated herein by reference in its entirety.

FIELD OF THE INVENTION

The present invention relates to compositions and methods for the treatment of immunodeficiency (e.g., primary immunodeficiency disease). In particular, the invention provides human plasma immunoglobulin compositions containing select antibody titers specific for a plurality of respiratory pathogens, methods of identifying human donors and donor samples for use in the compositions, methods of manufacturing the compositions, and methods of utilizing the compositions (e.g., for prophylactic administration and/or therapeutic treatment (e.g., passive immunization (e.g., immune-prophylaxis))).

BACKGROUND OF THE INVENTION

While most people have intact immune systems that serve to protect them from the wide variety of infectious organisms that commonly infect people including viruses, bacteria and fungi, many individuals have impaired or compromised immunity. There are many components to the immune system all of which cooperate to reject foreign invading pathogens. The humoral immune system that produces circulating antibody is one of the principal components that is often found to be lacking in immunocompromised individuals either at birth or may be a defect that is acquired. Immunodeficiency may be classified as primary or secondary.

Primary Immunodeficiency Diseases (PIDD) are a group of more than 150 diseases in which part of a subject's immune system is missing or does not function normally. To be considered a primary immunodeficiency, the cause of the immune deficiency must not be secondary in nature (e.g., caused by other disease, drug treatment, or environmental exposure to toxins). Most primary immunodeficiencies are genetic disorders and are diagnosed in children, although less severe forms may not be recognized until adulthood. About 1 in 500 people are born with a primary immunodeficiency.

Most immunodeficiencies (e.g., primary and secondary) result in a faulty humoral or cell mediated immune response toward infectious pathogens. The absence of a healthy, properly functioning humoral immune system (that part of the immune system required for generation of antibodies that are ultimately responsible for eradicating infection) renders a person susceptible to many infections. Infusion of immunoglobulin has been shown to reconstitute the ability of these immune defective individuals to defend themselves against infection Commercially available immunoglobulins are derived from pooled human serum, collected, processed, and distributed for sale by the blood and plasma products industry. The first purified human immunoglobulin G (IgG) preparation used clinically was immune serum globulin which was produced in the 1940s (Cohn, E. J., et al "J. Am Chem. Soc., 68:459-475 (1946)) and Oncely, J. L. et al., J. Am Chem Soc. 71:541-550 (1949). The immunoglobulin produced by this method demonstrated a molecular distribution having a high molecular weight, when analyzed by way of high resolution size exclusion chromatography. Immunoglobulin has historically been used primarily to prevent infections in patients who are immune deficient. Immunoglobulin obtained from the plasma of thousands of different donors contains antibodies to many of the pathogens that the donor individuals have encountered in their lifetime and it is these antibodies when infused into patients with PIDD that prevent them from suffering serious infections However, significant limitations exist with currently available immunoglobulin products. Since immunoglobulin from thousands of random donors is pooled the antibody titers to the many infectious organisms (e.g., pathogens) for which protection is sought varies greatly and very often is not sufficient to meet the immune needs of the immune suppressed individual (e.g., in case of a serious infection with a pathogen).

SUMMARY OF THE INVENTION

The present invention relates to compositions and methods for the treatment of immunodeficiency (e.g., primary immunodeficiency disease). In particular, the invention provides pooled human plasma immunoglobulin compositions, methods of identifying human plasma for use in the compositions, methods of manufacturing the compositions, and methods of utilizing the compositions (e.g., for prophylactic administration and/or therapeutic treatment (e.g., passive immunization (e.g., immune-prophylaxis))).

Accordingly, in one embodiment, the invention provides a composition comprising pooled plasma samples obtained from 1000 or more selected human subjects (e.g., human plasma donors), wherein the pooled plasma comprises elevated levels (e.g., selected, consistent and/or standardized levels), compared to the pathogen-specific antibody titers found in a mixture of plasma samples obtained from 1000 or more random human subjects (e.g., human plasma donors), of pathogen-specific antibody titers to one or more (e.g., two, three, four, or more) respiratory pathogens. The invention is not limited by the type of respiratory pathogens for which the pooled plasma comprises elevated levels of pathogen-specific antibody titers. The pooled plasma composition may comprise elevated levels of pathogen-specific antibody titers to one or more of respiratory syncytial virus, influenza A virus, influenza B virus, parainfluenza virus type 1, parainfluenza virus type 2, metapneumovirus, coronavirus, *S. pneumonia, H. influenza, L. pneumophila*, group A *Streptococcus*, or any other respiratory pathogen known in the art or described herein. In another embodiment, the pooled plasma from selected plasma donors comprises elevated levels, compared to the pathogen-specific antibody titers found in a mixture of plasma samples obtained from 1000 or more random human subjects, of pathogen-specific antibody titers to two or more respiratory pathogens described herein. In still another embodiment, the pooled plasma comprises elevated levels, compared to the pathogen-specific antibody titers found in a mixture of plasma samples obtained from 1000 or more random human subjects, of pathogen-specific antibody titers to three or more respiratory pathogens described herein. In one embodiment, the pooled plasma comprises a respiratory syncytial virus-specific antibody titer that is at least 2 fold greater (e.g. 2 fold, 3 fold, 4 fold, 5 fold 6 fold, 7 fold, 8 fold, 9 fold, 10 fold or more) than the respiratory syncytial virus-specific antibody titer found in a mixture of plasma samples obtained from 1000 or more random human subjects. In another embodiment, the pooled plasma comprises pathogen-specific antibody titers to at least two or more respiratory pathogens selected from respiratory syncytial virus, influenza A virus, influenza B virus, parainfluenza virus type 1, parainfluenza virus type 2, metapneumovirus, coronavirus, S. pneumonia, H. influenza, L. pneumophila, and group A Streptococcus that are each significantly elevated (e.g., at least 1.5, 1.6, 1.7, 1.8, 1.9, 2.0, 2.1, 2.2, 2.3, 2.4, 2.5, 2.6, 2.7, 2.8, 2.9, 3.0, 4.0, 5.0, 6.0, 7.0, 8.0 or more fold) compared to the pathogen-specific antibody titers found in a mixture of plasma samples obtained from 1000 or more random human subjects. In another embodiment, the pooled plasma comprises pathogen-specific antibody titers to at least three or more respiratory pathogens selected from respiratory syncytial virus, influenza A virus, influenza B virus, parainfluenza virus type 1, parainfluenza virus type 2, metapneumovirus, coronavirus, S. pneumonia, H. influenza, L. pneumophila, and group A Streptococcus that are each elevated at least 1.5 fold compared to the pathogen-specific antibody titers found in a mixture of plasma samples obtained from 1000 or more random human subjects. In still another embodiment, the pooled plasma comprises pathogen-specific antibody titers to at least four or more respiratory pathogens selected from respiratory syncytial virus, influenza A virus, influenza B virus, parainfluenza virus type 1, parainfluenza virus type 2, metapneumovirus, coronavirus, S. pneumonia, H. influenza, L. pneumophila, and group A Streptococcus that are each elevated at least 1.5 fold compared to the pathogen-specific antibody titers found in a mixture of plasma samples obtained from 1000 or more random human subjects. In one embodiment, the pooled plasma comprises plasma samples obtained from 1000-3000 or more (e.g., more than 1000, 1250, 1500, 1750, 2000, 2500, 3000, 3500, 4000 or more) human subjects. In one preferred embodiment, the pooled plasma comprises plasma samples obtained from 1000-1100 human subjects. In one embodiment, the composition comprising pooled plasma samples further comprises a pharmaceutically acceptable carrier (e.g., natural and/or non-naturally occurring carriers). In one embodiment, the pooled plasma composition is utilized to prepare immunoglobulin (e.g., for intravenous administration to a subject). In one embodiment, the pooled plasma composition and/or immunoglobulin provides a therapeutic benefit to a subject administered the composition that is not achievable via administration of a mixture of plasma samples obtained from 1000 or more random human subjects and/or immunoglobulin prepared from same. The invention is not limited by the type of therapeutic benefit provided. Indeed, a variety of therapeutic benefits may be attained including those described herein. In one embodiment, the pooled plasma and/or immunoglobulin possesses enhanced viral neutralization properties compared to a mixture of plasma samples obtained from 1000 or more random human subjects or immunoglobulin prepared from same. For example, in one embodiment, the pooled plasma possesses enhanced viral neutralization properties against one or more (e.g., two, three, four, five or more) respiratory pathogens (e.g., described herein). In a further embodiment, the enhanced viral neutralization properties reduce and/or prevent infection in a subject administered the composition for a duration of time that is longer than, and not achievable in, a subject administered a mixture of plasma samples obtained from 1000 or more random human subjects. For example, in one embodiment, immunoglobulin prepared from pooled plasma according to the invention (e.g., characterized, selected and blended according to the invention) that is administered to a subject results in a significant, concentration dependent anti-RSV neutralization activity and/or other respiratory pathogen (e.g., influenza A virus, influenza B virus, parainfluenza virus type 1, parainfluenza virus type 2, metapneumovirus, coronavirus, S. pneumonia, H. influenza, L. pneumophila, and group A Streptococcus) specific neutralization activity that is not achieved or achievable using immunoglobulin prepared from randomly pooled plasma samples (e.g., over a period of hours, days, weeks or longer). In one embodiment, the therapeutic benefit of a pooled plasma and/or immunoglobulin of the invention is enhanced viral neutralization properties that reduce or prevent infection in a subject administered the pooled plasma and/or immunoglobulin for a duration of time that is longer than, and not achievable in, a subject administered a mixture of pooled plasma and/or immunoglobulin prepared from same obtained from 1000 or more random human subjects. In another embodiment, the therapeutic benefit of pooled plasma and/or immunoglobulin of the invention is a therapeutic and/or protective level of antibody titers for measles, polio and/or diphtheria. In one embodiment, the therapeutic benefit is a significant reduction in viral load in the lung and/or nose of an immunocompromised subject administered the pooled plasma and/or immunoglobulin compared to a control subject not receiving same. In a further embodiment, the pooled plasma and/or immunoglobulin significantly reduces lung histopathology in an immunocompromised subject administered the pooled plasma and/or immunoglobulin compared to a control subject not receiving same. In yet a further embodiment, the pooled plasma and/or immunoglobulin significantly reduces the level of pathogenic viral RNA in a tissue selected from lung, liver and kidney in an immunocompromised subject administered the pooled plasma and/or immunoglobulin compared to a control subject. In one embodiment, a subject administered immunoglobulin prepared from pooled plasma according to the invention displays a mean fold increase in anti-RSV neutralization titer that is at least 4 fold, at least 5 fold, at least 6 fold, at least 7 fold, at least 8 fold, at least 9 fold or more at a time point of at least 1-14 days (e.g., 14 day, 15 days, 16 days, 17 days, 18 days, 19 days or more) post administration of the immunoglobulin. The invention is not limited by the amount of immunoglobulin administered to a subject. In one embodiment, a subject is administered between 250-2500 mg/kg of the immunoglobulin one time, or daily for two or more days (e.g., 2, 3, 4, or more consecutive days). In one embodiment, a subject is administered 1500 mg/kg of immunoglobulin on day one and 750 mg/kg immunoglobulin on day 2. In another embodiment, a subject is administered 750 mg/kg of immunoglobulin on day one and 750 mg/kg immunoglobulin on day 2. In one embodiment, the pooled plasma and/or immunoglobulin prepared from same reduces the incidence of infection in a subject administered the composition. In another embodiment, a pooled plasma and/or immunoglobulin prepared from same reduces the number of days a subject administered the pooled plasma and/or immunoglobulin is required to be administered antibiotics (e.g., to treat infection). In yet another embodiment, a pooled plasma and/or immunoglobulin prepared from same increases the trough level of circulating anti-respiratory pathogen specific antibodies in a subject (e.g., increases the level of neutralizing titers specific for respiratory pathogens (e.g., thereby providing protective levels of anti-respiratory pathogen specific antibodies between scheduled dates of administration of the pooled plasma and/or immunoglobulin prepared from same that are not maintained in a subject administered a mixture of plasma samples obtained from 1000 or more random human subjects or immunoglobulin prepared from same)).

In another embodiment, the invention provides an immunotherapeutic composition comprising pooled plasma samples obtained from 1000 or more selected human subjects, wherein the pooled plasma comprises elevated levels, compared to the pathogen-specific antibody titers found in a mixture of plasma samples obtained from 1000 or more random human subjects, of pathogen-specific antibody titers to two or more respiratory pathogens selected from respiratory syncytial virus, influenza A virus, influenza B virus, parainfluenza virus type 1, parainfluenza virus type 2, metapneumovirus, coronavirus, *S. pneumonia, H. influenza, L. pneumophila*, and group A *Streptococcus*; and a pharmaceutically acceptable carrier. In one embodiment, an immunotherapeutic composition provided herein further comprises one or more biologically active agents. The invention is not limited to the type of biologically active agent/ material. Indeed, a variety of biologically active agents/ materials may be used including, but not limited to, antibodies, anti-toxin material, anti-inflammatory agent, anti-cancer agent, antimicrobial agent, therapeutic agent, antihistamine, cytokine, chemokine, vitamin, mineral, or the like. In one embodiment, the biologically active agent is an anti-toxin agent. In one embodiment, the anti-toxin agent is a mono-specific, bi-specific or multi-specific antibody with specificity toward a viral, bacterial or fungal toxin. In a further embodiment, the bacterial or fungal toxin is selected from Botulinum neurotoxin, Tetanus toxin, *E. coli* toxin, *Clostridium difficile* toxin, *Vibrio* RTX toxin, Staphylococcal toxins, Cyanobacteria toxin, and mycotoxins.

In another embodiment, the immunotherapeutic composition further comprises an aliquot of a single or multiple monoclonal antibodies with a single or multiple specificities (e.g., the immunogenic composition may be spiked with one or more antibodies or biologically active material (e.g., a monoclonal antibody of any specificity, an anti-toxin agent, etc.)). The invention is not limited by the type of one or more antibodies that are added to (e.g., spiked into) the immunogenic composition. Indeed, any one or more antibodies (e.g., specific for a pathogen or pathogen product) may be used including, but not limited to standard antibodies, bi-specific antibodies, multi-specific antibodies, or the like known in the art (e.g., specific for one or a multiplicity of antigens).

In another embodiment, the invention provides a method of providing immunotherapy to a subject (e.g., a subject in need thereof (e.g., a subject with disease or at risk for disease)) comprising administering to the subject a therapeutically effective amount of a composition comprising pooled plasma samples obtained from 1000 or more selected human subjects, wherein the pooled plasma comprises elevated levels, compared to the pathogen-specific antibody titers found in a mixture of plasma samples obtained from 1000 or more random human subjects, of pathogen-specific antibody titers to one or more (e.g., two, three, four, five or more) respiratory pathogens selected from respiratory syncytial virus, influenza A virus, influenza B virus, parainfluenza virus type 1, parainfluenza virus type 2, metapneumovirus, coronavirus, *S. pneumonia, H. influenza, L. pneumophila*, and group A *Streptococcus*. In one embodiment, the immunotherapy is used to prophylactically treat infection associated with a microbial pathogen. In another embodiment, the immunotherapy is used to therapeutically treat infection associated with a microbial pathogen. In one embodiment, the subject has an immunodeficiency. The invention is not limited by the type of immunodeficiency. Indeed, the invention may be used to provide immunotherapy compositions and methods to an immunocompromised patient, a subject at elevated risk of infection (e.g., experiencing an extended hospital stay, and/or anticipating direct exposure to multiple specific pathogens), and/or an individual whose immune response has been rendered deficient (e.g., from a disease of the immune system, from a disease that depresses immune functions (e.g., AIDS, idiopathic thrombocytopenic purpura (ITP), etc.) from a therapy (e.g., chemotherapy) that results in a suppressed immune system). In one embodiment, immunotherapy methods provided herein arrest the progression of the immune deficiency and enable at least a partial recovery from the immune deficiency. An advantage of the compositions and methods described herein is that many embodiments do not require the subject to be given additional drugs to treat their risk of infection, and therefore they are spared adverse side effects or interactions with other therapies. Another advantage of the compositions and methods described herein is that the compositions and methods may be used to treat or prevent disease wherein drugs or other conventional treatments do not exist to treat or prevent the disease (e.g., compositions and methods of the invention can be used to treat and/or prevent infection with respiratory syncytial virus). Yet another advantage of the compositions and methods of the invention is that the compositions and methods of the invention may be used to treat infection when the underlying infectious agent is unknown. Moreover, in one embodiment, compositions and methods of the invention are utilized for prophylactic and/or therapeutic treatment of infection for which there exists no known cure (e.g., various viral illnesses). In some embodiments, compositions and methods of the invention are utilized for prophylactic and/or therapeutic treatment of infections (e.g., that are resistant to existing treatment (e.g., antibiotic resistant disease/infection (e.g., vancomycin resistant staphylococci)). In some embodiments, compositions and methods of the invention are utilized for prophylactic and/or therapeutic treatment of a subject that harbors a non-competent immune system (e.g., in which treatment with antibiotic or other conventional antimicrobial therapy would have little to no value). In other embodiments, compositions and methods of the invention are utilized to reduce the risk of a subject developing a respiratory infection. The invention is not limited by the type of subject treated with the compositions and methods of the invention. Indeed, a variety of subjects may be so treated, including, but not limited to, a subject at risk of developing an infection (e.g., respiratory or other type of infection (e.g., thereby reducing the risk of developing infection in a subject having an elevated risk of infection)). In one embodiment, a subject treated with a composition of the invention has or is diagnosed as having a primary immunodeficiency disease (PIDD). In another embodiment, the subject is an end stage renal disease (ESRD) patient; cancer patient on immunosuppressive therapy, AIDS patient, diabetic patient, neonate, transplant patient, patient on immunosuppression therapy, patient with PIDD and other immune deficiencies, patient with malfunctioning immune system, autoimmune disease patient, an elderly person in an extended care facility, patient with autoimmune disease on immunosuppressive therapy, transplant patient, patient with invasive surgical procedure, burn patient, or other patient in acute care setting. In one embodiment, the immunotherapy provides the subject with prophylactic immunity against two or more pathogens selected from *Clostridium botulinum*, cytomegalovirus (CMV), *Corynebacterium diphtheriae*, hepatitis A virus, measles virus, hepatitis B virus, Hepatitis C virus, human immunodeficiency virus (HIV), rabies virus, tetanus, vaccinia virus, *Pseudomonas aeruginosa*, varicella-zoster virus, influenza A virus, influenza B virus, parainfluenza virus type 1, parainfluenza virus type 2, metapneumovirus, coronavirus and respiratory syncytial virus (RSV). However, the invention is not so limited. Indeed, immunotherapy with the compositions and methods of the invention may provide the subject with prophylactic immunity to any of the microbial pathogens described herein. In another embodiment, the immunotherapy is used to treat infection in the subject caused by *Clostridium botulinum*, cytomegalovirus (CMV), *Corynebacterium diphtheriae*, hepatitis A virus, measles virus, hepatitis B virus, Hepatitis C virus, human immunodeficiency virus (HIV), rabies virus, tetanus, vaccinia virus, *Pseudomonas aeruginosa*, varicella-zoster virus, influenza A virus, influenza B virus, parainfluenza virus type 1, parainfluenza virus type 2, metapneumovirus, coronavirus and/or respiratory syncytial virus (RSV), or any microbial pathogen described herein.

In another embodiment, the invention provides a method of producing a pooled plasma composition, comprising obtaining plasma samples from human subjects; characterizing the pathogen-specific antibody titer, within a subset of the plasma samples, for one or more respiratory pathogens selected from respiratory syncytial virus, influenza A virus, influenza B virus, parainfluenza virus type 1, parainfluenza virus type 2, metapneumovirus and coronavirus; selecting, based upon the antibody titers characterized, plasma samples that have elevated levels, compared to a control value (e.g., the pathogen-specific antibody titers found in a mixture of plasma samples obtained from 1000 or more random human subjects), of pathogen-specific antibody titers to one or more respiratory pathogens selected from respiratory syncytial virus, influenza A virus, influenza B virus, parainfluenza virus type 1, parainfluenza virus type 2, metapneumovirus and coronavirus; pooling the selected plasma samples with other plasma samples to generate the pooled plasma composition, wherein the pooled plasma composition comprises pathogen-specific antibody titers to one or more respiratory pathogens selected from respiratory syncytial virus, influenza A virus, influenza B virus, parainfluenza virus type 1, parainfluenza virus type 2, metapneumovirus and coronavirus, the one or more titers being elevated at least 1.5 fold compared to a control value (e.g., the pathogen-specific antibody titers in a mixture of plasma samples obtained from 1000 or more random human subjects). In one embodiment, the method comprises selecting, based upon the antibody titers characterized, plasma samples that have elevated levels, compared to the pathogen-specific antibody titers found in a mixture of plasma samples obtained from 1000 or more random human subjects, of pathogen-specific antibody titers to two or more respiratory pathogens selected from respiratory syncytial virus, influenza A virus, influenza B virus, parainfluenza virus type 1, parainfluenza virus type 2, metapneumovirus and coronavirus. In a further embodiment, the method comprises selecting, based upon the antibody titers characterized, plasma samples that have elevated levels, compared to the pathogen-specific antibody titers found in a mixture of plasma samples obtained from 1000 or more random human subjects, of pathogen-specific antibody titers to three, four or more respiratory pathogens selected from respiratory syncytial virus, influenza A virus, influenza B virus, parainfluenza virus type 1, parainfluenza virus type 2, metapneumovirus and coronavirus. In one embodiment, the pooled plasma composition comprises pathogen-specific antibody titers to at least two or more respiratory pathogens selected from respiratory syncytial virus, influenza A virus, influenza B virus, parainfluenza virus type 1, parainfluenza virus type 2, metapneumovirus and coronavirus that are each elevated at least 1.5 fold compared to the pathogen-specific antibody titers found in a mixture of plasma samples obtained from 1000 or more random human subjects. In one embodiment, the pooled plasma composition comprises pathogen-specific antibody titers to at least three or more respiratory pathogens selected from respiratory syncytial virus, influenza A virus, influenza B virus, parainfluenza virus type 1, parainfluenza virus type 2, metapneumovirus and coronavirus that are each elevated at least 1.5 fold compared to the pathogen-specific antibody titers found in a mixture of plasma samples obtained from 1000 or more random human subjects. In another embodiment, the pooled plasma composition comprises a respiratory syncytial virus-specific antibody titer that is at least 2 fold greater (e.g., 2, 2.5, 3, 3.5, 4.5, 5, 6, 7, 8, 9, 10 fold or more) than the respiratory syncytial virus-specific antibody titer found in a mixture of plasma samples obtained from 1000 or more random human subjects. For example, in one embodiment, the invention provides a method of producing a pooled plasma composition containing a specific, elevated antibody titer for respiratory syncytial virus (RSV) and a specific, elevated antibody titer for one or more other respiratory pathogens, from at least 1000 human plasma donors, comprising obtaining plasma samples from selected human plasma donors and non-selected human plasma donors, wherein the selected human plasma donors comprise high titer selected human donors and non-high titer selected human donors, wherein the selected human donors are identified via characterizing the specific titer of antibodies to respiratory syncytial virus in a plasma sample from a human donor, wherein characterizing the specific titer of antibodies to respiratory syncytial virus comprises a first, plasma screening assay utilized to assess neutralizing activity in the plasma sample; and a second screening assay characterizing the specific antibody titer of the purified immunoglobulin fraction of each plasma sample identified as displaying the top 20% of neutralizing activity using the first, plasma screening assay, wherein a purified immunoglobulin fraction possessing an RSV neutralization titer of 1800 or above is used to identify a plasma sample containing an elevated antibody titer for the one or more respiratory pathogens selected from parainfluenza virus 1, parainfluenza virus 2, coronavirus OC43, coronavirus 229E, influenza A virus, influenza B virus, and metapneumovirus, and used to categorize a human donor as a high titer selected human donor; and pooling 1000 or more plasma samples from high titer selected human donors, non-high titer selected human donors, and non-selected human donors in order to generate the pooled plasma composition, wherein 10-65%, 20-55%, 30-50%, 40-50% (e.g., in a preferred embodiment, less than 50% (e.g., about 30-45%, 35-45%, 40-45%)) of the 1000 or more plasma samples are from high titer selected human donors; and wherein the pooled plasma composition comprises an RSV specific antibody titer that is at least 3 times greater than the RSV specific antibody titer in a control sample, and an antibody titer for one or more respiratory pathogens selected from parainfluenza virus 1, parainfluenza virus 2, coronavirus OC43 and coronavirus 229E that is at least about 1.5 times greater (e.g., about 1.25, 1.3, 1.4, 1.5, 1.6, 1.7, 1.8, 1.9, 2.0, 2.5, 3.0 times or more) than the antibody titer in the control sample, wherein the control sample is a mixture of plasma samples obtained from 1000 or more random human subjects. Pooled plasma compositions produced according to the methods described herein are also provided. In one embodiment, less than 50% of the total volume of the pooled plasma composition (e.g., in preferred embodiments, about 30-45%, 35-45%, 35-40%)) comprises plasma obtained from high titer selected human donors; about 55-70% (e.g., in preferred embodiment, about 55-75%, 55-65%) of the total volume of the pooled plasma composition comprises plasma obtained from non-high titer selected human donors, and about 3-20% of the total volume of the pooled plasma composition comprises plasma from non-selected human donors. In one embodiment, the pooled plasma composition provides a therapeutic benefit to a subject administered the composition that is not achievable via administration of a mixture of plasma samples obtained from 1000 or more random human subjects. The invention is not limited by the type of therapeutic benefit provided. Indeed, a variety of therapeutic benefits may be attained including those described herein. In one embodiment, the pooled plasma composition possesses enhanced viral neutralization properties compared to a mixture of plasma samples obtained from 1000 or more random human subjects. In a further embodiment, the enhanced viral neutralization properties reduce and/or prevent infection in a subject administered the composition for a duration of time that is longer than, and not achievable in, a subject administered a mixture of plasma samples obtained from 1000 or more random human subjects.

In one embodiment, the invention provides the use of neutralizing antibody titer to RSV (or other respiratory pathogen) as a biomarker to identify plasma donors that are high/strong responders in general to other respiratory pathogens (e.g., influenza A virus, influenza B virus, parainfluenza virus type 1, parainfluenza virus type 2, metapneumovirus, coronavirus, *S. pneumonia, H. influenza, L. pneumophila*, and group A *Streptococcus*). In a further embodiment, the invention provides a method of using the level of a respiratory pathogen specific neutralizing antibody titer (e.g., RSV neutralizing antibody titer) detected in a plasma donor sample as a biomarker that indicates and/or provides information regarding the level of respiratory pathogen specific neutralizing antibody titers within the sample to one or more of influenza A virus, influenza B virus, parainfluenza virus type 1, parainfluenza virus type 2, metapneumovirus and coronavirus. The use of such a biomarker makes possible the ability to identify donors and plasma (e.g., high titer selected donor and/or donor sample) that can be blended with non-high titer selected donor plasma or non-selected donor plasma to provide a pooled plasma composition of the invention. In one embodiment, a plasma sample identified as having a specific antibody titer to respiratory syncytial virus (e.g., via a first, plasma screening assay utilized to assess neutralizing activity in the plasma sample; and a second screening assay characterizing the specific antibody titer of the purified immunoglobulin fraction of each plasma sample identified as displaying the top 20% of neutralizing activity using the first, plasma screening assay) of about 1800 or above (e.g., about 1800, 1850, 1900, 1950, 2000, 2050, 2100 or more) is used to identify a plasma sample containing an elevated antibody titer (e.g., wherein the elevated titer is a titer that is at least about 1.5 times greater (e.g., about 1.3, 1.4, 1.5, 1.6, 1.7, 1.8, 1.9, 2.0, 2.5, 3.0 times or more) than the antibody titer in a control sample, wherein the control sample is a mixture of plasma samples obtained from 1000 or more random human subjects) for one or more respiratory pathogens selected from parainfluenza virus 1, parainfluenza virus 2, coronavirus OC43, coronavirus 229E, influenza A virus, influenza B virus, and metapneumovirus.

In another embodiment, the invention provides hyperimmune globulin compositions (e.g., adenoviral hyperimmune globulin compositions, RSV hyperimmune globulin compositions pneumococcal hyperimmune globulin compositions, etc.) and methods of generating and using the same (e.g., for passive immunization of patients susceptible to, or suffering from, infection (e.g., bacterial infection (e.g., associated with *Streptococcus pneumonia, Haemophilus* influenza, etc.), viral infection (e.g., associated with adenovirus, herpes virus, influenza virus, rhinovirus, etc.), fungal infection (e.g., associated with *Aspergillus fumigatus, Cladosporium* or other fungi) and/or exposure to microbial toxins and/or harmful agents (e.g., animal venom))). In one embodiment, pooled human plasma samples (e.g., with elevated titer of desired antibodies (e.g., targeted to specific pathogens and/or that are identified as containing a specific desired property (e.g., enhanced anti-inflammatory property))) are combined to produce tailored immunoglobulin pools (e.g., that possess a desired characteristic that is not achievable in the absence of combining the pools (e.g., greater level of protection against infection, inflammation or toxins)) with elevated titer of antibodies against multiple specific pathogens or pathogen products (e.g., toxins).

In one embodiment, the invention provides compositions and methods for obtaining a composition comprising pooled plasma samples (e.g., plasma from a plurality of donors (e.g., that contain elevated microbial-specific antibody titers (e.g., high titer of viral-, bacterial-, and/or fungal-pathogen specific immunoglobulin))). As described herein, the plasma pool may be utilized as or in a therapeutic composition (e.g., to treat and/or prevent viral, bacterial and/or fungal infection). In one embodiment, the invention provides a composition comprising pooled plasma samples (e.g., a therapeutic composition) comprising plasma from a plurality of donors (e.g., 1000 or more human donors), wherein all or a subset of the plurality of donors possess a high titer of microbial pathogen-specific antibodies to one or a plurality of microbial pathogens as a result of administration of one or a plurality of immunogenic compositions comprising microbial antigens to the plurality of donors. The invention is not limited by the method of obtaining an antibody pool. Indeed, a variety of methods may be utilized, including, but not limited to, administering one or more microbial (e.g., viral, bacterial and/or fungal) antigens to a host subject to generate enhanced expression of microbial (e.g., viral, bacterial and/or fungal) specific antibodies and obtaining serum or plasma containing microbial (e.g., viral, bacterial and/or fungal) specific, enhanced high titer antibody pools from the donor or plurality of donors. In some embodiments, the plasma/serum is purified and/or concentrated (e.g., in order to concentrate microbial (e.g., viral, bacterial and/or fungal) specific immunoglobulin present therein (e.g., prior to providing (e.g., administration) to a subject). The invention is not limited by the one or more microbial (e.g., viral, bacterial and/or fungal) antigens utilized to generate enhanced expression of microbial (e.g., viral, bacterial and/or fungal) specific antibodies. Indeed, a variety of microbial (e.g., viral, bacterial and/or fungal) antigens may be utilized, including, but not limited to, conjugated and unconjugated microbial antigenic proteins or peptides, sugars (polysaccharides), cell wall components, viral antigens etc. In some embodiments, the viral, bacterial and/or fungal antigens utilized are, or are in the form of, a commercially available vaccine. Commercially available vaccines are well known to those in the field. By way of example, non-limiting examples of commercially available vaccines that find use in the invention include, but are not limited to, Adenovirus Type 4 and Type 7 vaccine, Anthrax vaccine, BCG vaccine, Diphtheria and Tetanus Toxoids, Diphtheria and Tetanus Toxoids, Diphtheria and Tetanus Toxoids and Acellular Pertussis vaccine, Diphtheria and Tetanus Toxoids and Acellular Pertussis vaccine, Diphtheria and Tetanus Toxoids and Acellular Pertussis vaccine, Diphtheria and Tetanus Toxoids and Acellular Pertussis vaccine, Hepatitis B (recombinant) and Inactivated Poliovirus vaccine, Diphtheria and Tetanus Toxoids and Acellular Pertussis, Inactivated Poliovirus and *Haemophilus* b Conjugate (Tetanus Toxoid Conjugate) vaccine, *Haemophilus* b Conjugate vaccine (e.g., Meningococcal Protein Conjugate, Tetanus Toxoid Conjugate), recombinant Hepatitis B vaccine, Hepatitis A vaccine, Hepatitis A Inactivated and Hepatitis B (Recombinant (e.g., RECOMBIVAX HB, ENGERIX-B) vaccine, Human Papillomavirus vaccine (e.g., multivalent, bivalent, quadrivalent (Types 6, 11, 16, 18) vaccine), Influenza Virus vaccine (e.g., influenza A (H1N1) vaccine, monovalent vaccine, trivalent (e.g., Types A and B) vaccine, H5N1 vaccine, FLUMIST, FLUARIX, FLUVIRIN, AGRIFLU, FLUZONE, FLUXELVAX, FLUMIST quadrivalent,), Japanese Encephalitis Virus vaccine, Measles Virus vaccine, Measles and Mumps Virus vaccine, Measles, Mumps, and Rubella Virus vaccine, Measles, Mumps, Rubella and Varicella Virus vaccine, Meningococcal vaccine (e.g., Groups A, C, Y, and W-135 Oligosaccharide Diphtheria CRM197 Conjugate vaccine), Meningococcal Groups C and Y and *Haemophilus* b Tetanus Toxoid Conjugate vaccine, Meningococcal Polysaccharide (Serogroups A, C, Y and W-135) Diphtheria Toxoid Conjugate vaccine, Meningococcal Polysaccharide vaccine (e.g., Groups A, C, Y and W-135 Combined vaccine), Mumps Virus vaccine, Plague vaccine, Pneumococcal vaccine (e.g., PNEUMOVAX23, Pneumococcal 7-valent Conjugate vaccine, PREVNAR, Pneumococcal 13-valent Conjugate vaccine), Poliovirus vaccine, Rabies vaccine, Rotavirus vaccine, Rubella Virus vaccine, Smallpox (Vaccinia) vaccine, Tetanus and Diphtheria Toxoids (e.g., DECAVAC, TENIVAC), Tetanus Toxoid, Reduced Diphtheria Toxoid and Acellular Pertussis vaccine, Typhoid vaccine, Typhoid Vi Polysaccharide vaccine, Varicella Virus vaccine, Yellow Fever vaccine, and/or Zoster vaccine. In some embodiments, the microbial antigen is a viral antigen (e.g., respiratory syncytial virus antigen), bacterial antigen (e.g., *S. pneumoniae* antigen) and/or a fungal antigen. In some embodiments, a *S. pneumoniae* antigen is a *S. pneumoniae* cell membrane sugar (e.g., a polysaccharide). In some embodiments, a *S. pneumoniae* antigen is a conjugate vaccine (e.g., conjugated to a carrier and/or adjuvant (e.g., a protein or other carrier molecule). In some embodiments, a *S. pneumoniae* antigen is an unconjugated vaccine. In some embodiments, the conjugate vaccine or unconjugated vaccine contains 1, 2, 3, 4, 5, 6, 7, 8, 9, 10, 11, 12, 13, 14, 15, 16, 17, 18, 19, 20, 21, 22, 23 or more different antigens (e.g., from an equal number of different serotypes of *S. pneumonia*). In some embodiments, the one or more different serotypes of *S. pneumoniae* include, but are not limited to, serotypes 1, 2, 3, 4, 5, 6A, 6B, 7A, 7B, 7C, 7D, 7E, 7F, 8, 9A-9V, 12, 14, 18C, 19A-19F, 23A-23F, and 25. In some embodiments, the one or more different serotypes of *S. pneumoniae* are selected from any one of the more the 90 different *S. pneumoniae* serotypes identified. In some embodiments, the one or more different serotypes of *S. pneumoniae* is newly identified.

In one embodiment, compositions are provided that comprise a plurality of different types of antibodies (e.g., directed to different pathogens (e.g., viral pathogens, bacterial pathogens, eukaryotic pathogens, etc.), recognize different antigens, recognize different epitopes, etc.) and are enriched (e.g., elevated titer) for at least two different antibodies or sets of antibodies (e.g., directed to different pathogens, recognize different antigens, recognize different epitopes, etc.). In particular embodiments, compositions comprise tailored antibody pools. In some embodiments, at least from about 0.01% to about 70% of the total immunoglobulin present in the composition is directed to one or more targeted pathogens, although the invention is no so limited (e.g., the composition may comprise less than 0.01% or more than 70% of immunoglobulin directed to targeted pathogens). Immunoglobulin directed to targeted pathogens may comprise >0.1%>2%, >5%, >10%, >20%, >30%, >40%, >50%, >60%, >70%, >80%, or >90% of the total immunoglobulin present in the composition. In certain embodiments, a composition comprises two or more immunoglobulins to targeted pathogens, each present at greater than 1% of total immunoglobulin present in the composition (e.g., two or more immunoglobulins to targeted pathogens present at greater than 1.5%, 2.0%, 3.0%, 4.0%, 5.0% or more of total immunoglobulin, two or more immunoglobulins to targeted pathogens present at greater than 10% of total immunoglobulin, two or more immunoglobulins to targeted pathogens present at greater than 15% of total immunoglobulin, two or more immunoglobulins to targeted pathogens present at greater than 20% of total immunoglobulin, two or more immunoglobulins to targeted pathogens present at greater than 25% of total immunoglobulin, etc.).

Any suitable method for obtaining plasma, antibody samples, pooled plasma compositions and/or immunoglobulin from same are within the scope of the present invention. Further, any suitable method for producing, manufacturing, purifying, fractionating, enriching, etc. antibody samples and/or plasma pools is within the bounds of the present invention. Exemplary techniques and procedures for collecting antibody samples and producing plasma pools are provide, for example, in: U.S. Pat. Nos. 4,174,388; 4,346,073; 4,482,483; 4,587,121; 4,617,379; 4,659,563; 4,665,159; 4,717,564; 4,717,766; 4,801,450; 4,863,730; 5,505,945; 5,582,827; 6,692,739; 6,962,700; 6,984,492; 7,045,131; 7,488,486; 7,597,891; 6,372,216; U.S. Patent App. No. 2003/0118591; U.S. Patent App. No. 2003/0133929 U.S. Patent App. No. 2005/0053605; U.S. Patent App. No. 2005/0287146; U.S. Patent App. No. 2006/0110407; U.S. Patent App. No. 2006/0198848; U.S. Patent App. No. 2006/0222651; U.S. Patent App. No. 2007/0037170; U.S. Patent App. No. 2007/0249550; U.S. Patent App. No. 2009/0232798; U.S. Patent App. No. 2009/0269359; U.S. Patent App. No. 2010/0040601; U.S. Patent App. No. 2011/0059085; and U.S. Patent App. No. 2012/0121578; herein incorporated by reference in their entireties. Embodiments of the present invention may utilize any suitable combination of techniques, methods, or compositions from the above listed references.

In some embodiments, plasma and/or antibody samples are obtained from donor subjects in the form of donated or purchased biological material (e.g., blood or plasma). In some embodiments, plasma and/or antibody samples (e.g., blood, plasma, isolated antibodies, etc.) are obtained from a commercial source. In some embodiments, a plasma and/or antibody sample, blood donation, or plasma donation is screened for pathogens, and either cleaned or discarded if particular pathogens are present. In one embodiments, screening occurs prior to pooling a donor sample with other donor samples. In other embodiments, screening occurs after pooling of samples. Antibodies, blood, and/or plasma may be obtained from any suitable subjects. In some embodiments, antibodies, blood, and/or plasma are obtained from a subject who has recently (e.g., within 1 year, within 6 months, within 2 months, within 1 month, within 2 weeks, within 1 week, within 3 days, within 2 days, within 1 day) been vaccinated against or been exposed to one or more specific pathogens. In certain embodiments, a subject positive for antibodies to the pathogen of interest is administered antigens to that pathogen to increase titer of the desired antibodies. In some embodiments, a subject has produced antibodies and/or has elevated titer of antibodies against one or more specific pathogens. In certain embodiments, a subject, whether negative or positive for antibodies to a specific microbial pathogen is administered one or more different viral, bacterial and/or fungal antigens/vaccines in order to increase titer of specific, desired antibodies (e.g., viral-, bacterial- and/or fungal-specific antibodies). Pathogens to which a donor may have elevated titer of antibodies include, but are not limited to: *Clostridium botulinum*, cytomegalovirus (CMV), *Corynebacterium diphtheriae*, hepatitis A virus, measles virus, hepatitis B virus, Hepatitis C virus, human immunodeficiency virus (HIV), rabies virus, tetanus virus, vaccinia virus, *Pseudomonas aeruginosa*, varicella-zoster virus, and respiratory syncytial virus (RSV), human immunodeficiency virus, hepatitis C virus, human papilloma virus, hepatitis B virus, or other human viral or bacterial pathogens.

In some embodiments, plasma samples known, identified, and/or selected (e.g., according to methods described herein) to contain elevated titer of a particular antibody (e.g., antibodies directed to RSV) or a set of plasma samples are combined (e.g., pooled) to produce a composition comprising pooled plasma samples (e.g., with elevated titer of antibodies directed to a particular pathogen or to a set of pathogens (e.g., RSV, and one or more other respiratory pathogens)). For example, a composition comprising pooled plasma samples is produced by pooling plasma samples obtained from selected human subjects and non-selected human subjects, wherein the pooled plasma comprises elevated levels (e.g., elevated by about 20%, 30%, 40%, 50%, 60%, 70%, 85%, 90%, 100%, 125%, 150%, 160%, 170%, 175%, 180%, 200%, 225%, 250%, 275%, 300%, 350%, 400%, 450%, 500%, 550%, 600%, 650%, 700%, 750%, 800%, 850%, 900%, 950%, 1000% or more), compared to a control value (e.g., the pathogen-specific antibody titers found in a mixture of plasma samples obtained from 1000 or more random human subjects), of pathogen-specific (e.g., RSV specific, influenza A virus specific, influenza B virus specific, parainfluenza virus type 1 specific, parainfluenza virus type 2 specific, metapneumovirus specific and/or coronavirus specific) antibody titers. In a further embodiment, immune globulin is prepared from the pooled plasma (e.g., according to techniques and methods described herein). In some embodiments, a composition comprising pooled plasma samples is produced by pooling plasma samples obtained from selected human donors and non-selected human donors, wherein the pooled plasma comprises elevated levels, compared to the pathogen-specific antibody titers found in a mixture of plasma samples obtained from 1000 or more random human subjects, of RSV-specific antibody titers (e.g., individuals recently exposed to RSV, individuals recently vaccinated for RSV, etc) and other respiratory pathogen specific titers. In one embodiment, a composition comprising pooled plasma samples and/or immune globulin prepared therefrom of the invention is a sterile solution with a pH of about 6.0-7.8 (e.g., 5.0-6.0, 6.0, 6.1, 6.2, 6.3, 6.4, 6.5, 6.6, 6.7, 6.8, 6.9, 7.0, 7.1, 7.2, 7.3, 7.4, 7.5, 7.6. 7.7, 7.8, or higher). In another embodiment, a composition comprising pooled plasma samples and/or immune globulin prepared therefrom of the invention is prepared according US FDA standards for immune globulin preparation (e.g., 37 CFR §§ 640.100; 640.101; 640.102; 640.103; 640.104, Apr. 1, 2013). In one embodiment, a composition comprising pooled plasma samples and/or immune globulin prepared therefrom of the invention (e.g., RSV-IVIG described herein, in particular, in the Examples) possesses at least the minimum level of antibody titers to *Corynebacterium diphtheria*, measles virus, and polio virus recommended by the FDA (e.g., see 37 CFR § 640.104).

In one embodiment, a composition comprising pooled plasma samples and/or immune globulin prepared therefrom of the invention comprises elevated antibody titer levels, compared to a control antibody titer value (e.g., the pathogen-specific antibody titer found in a mixture of plasma samples obtained from 1000 or more random human subjects), of pathogen-specific antibodies to respiratory syncytial virus and one or more respiratory pathogens selected from, influenza A virus, influenza B virus, parainfluenza virus type 1, parainfluenza virus type 2, metapneumovirus and coronavirus, wherein the elevated levels of RSV specific, influenza A virus specific, influenza B virus specific, parainfluenza virus type 1 specific, parainfluenza virus type 2 specific, metapneumovirus specific and/or coronavirus specific antibodies are elevated at least 20%, 30%, 40%, 50%, 60%, 70%, 85%, 90%, 100%, 125%, 150%, 175%, 200%, 225%, 250%, 275%, 300%, 350%, 400%, 450%, 500%, 550%, 600%, 650%, 700%, 750%, 800%, 850%, 900%, 950%, 1000% or more), compared to a control value (e.g., the pathogen-specific antibody titer level found in a mixture of plasma samples obtained from 1000 or more random human subjects). The invention provides a method, in one embodiment, of generating the above described composition comprising obtaining plasma samples from selected human donors and non-selected human donors; pooling 1000 or more plasma samples from both selected donors and non-selected donors to generate the pooled plasma composition. In one embodiment, the plasma samples from selected human donors and non-selected human donors are screened in order to confirm the absence of bloodborne pathogens (e.g., before or after pooling). In a further embodiment, selected human donors are identified via identifying the specific titer of antibodies to one or more respiratory pathogens selected from respiratory syncytial virus, influenza A virus, influenza B virus, parainfluenza virus type 1, parainfluenza virus type 2, metapneumovirus and coronavirus. In a preferred embodiment, selected human donors are identified via identifying the specific titer of antibodies to respiratory syncytial virus. In a further embodiment, the selected human donors comprise high titer donors and medium titer donors, wherein high titer donors comprise a pathogen specific antibody titer that is 2-5 times, 5-8 times, 8-10 times, 10-14 times, 14 times or greater than a standard value (the titer of pathogen specific antibodies present in a pool of plasma samples from 1000 or more random human subjects), and wherein medium titer donors comprise a pathogen specific antibody titer that is the titer of pathogen specific antibodies present in a pool of plasma samples from 1000 or more random human subjects or that is only marginally higher (e.g., 5-20% higher) or marginally lower (e.g., 5-20% lower) than this value. In still a further embodiment, the selected human donors comprise high titer donors, medium titer donors and low titers donors, wherein high titer donors comprise a pathogen specific antibody titer that is 2-5 times, 5-8 times, 8-10 times, 10-14 times, 14 times or greater than a standard value (the titer of pathogen specific antibodies present in a pool of plasma samples from 1000 or more random human subjects), wherein medium titer donors comprise a pathogen specific antibody titer that is the titer of pathogen specific antibodies present in a pool of plasma samples from 1000 or more random human subjects or that is only marginally higher (e.g., 5-20% higher) or marginally lower (e.g., 5-20% lower) than this value, and wherein low titer donors comprise a pathogen specific antibody titer that is around 20-50 percent the titer of pathogen specific antibodies present in a pool of plasma samples from 1000 or more random human subjects.

In one embodiment, identifying antibody titer comprises a first, plasma screening assay assessing neutralizing activity in a plasma sample, and a second screening assay assessing antibody titer in a purified immunoglobulin fraction of the plasma sample. In one embodiment, neutralizing activity in plasma is measured via the absence of infection by RSV of hepatocytes. In a further embodiment, the first plasma screening assay assessing neutralization activity categorizes plasma samples as high titer, medium titer, or low titer for RSV specific antibodies, wherein a high titer RSV donor/donor sample is one having an RSV neutralizing titer of about 7800 or greater, a medium titer RSV donor/donor sample is one having an anti-RSV titer of about 3300-7799, and a low titer RSV donor/donor sample is one having an anti-RSV titer of about 1800-3299 (e.g., titer being calculated and assigned to a donor/donor sample as the dilution that give 50% inhibition of virus growth (that point which is 50% of the two extremes (saline plus virus is 100 growth and no virus added is 0 growth) according to methods described herein (See, e.g., Examples 1 and 2). In still a further embodiment, only plasma samples identified as displaying the top 20%-30% of neutralizing activity of all donors are processed to produce purified immunoglobulin and subsequently screened using the second screening assay. In a preferred embodiment, only plasma samples identified as displaying the top 20% of neutralizing activity of all donors are processed to produce purified immunoglobulin and subsequently screened using the second screening assay. In one embodiment, the second screening assay characterizes the RSV specific antibody titer of a purified immunoglobulin fraction of the plasma sample. In a preferred embodiment, a donor/donor sample that has an RSV neutralization titer of at least 1800 in a purified immunoglobulin fraction of the plasma sample is scored as a high titer donor. In a preferred embodiment, an RSV neutralization titer of at least 1800 is used to identify a donor/donor sample (e.g., plasma sample) comprising elevated levels of one or more respiratory pathogens selected from influenza A virus, influenza B virus, parainfluenza virus type 1, parainfluenza virus type 2, metapneumovirus and coronavirus. In another embodiment, the pooled plasma composition comprises an RSV neutralization antibody titer of 1800 or more. In one embodiment, less than half (e.g., about 10-20%, 20-30%, 30-40%, 40-50%) of the 1000 or more donors are high titer donors. In a preferred embodiment, about 30-45%, 35-45%, or 35-40% of the 1000 or more donors are high titer donors. In another embodiment, the invention provides a pooled plasma composition and/or immune globulin obtained from same prepared according to the above described methods. In one embodiment, the pooled plasma composition comprise about 1800-2500 liters (e.g., about 1800, about 1900, about 2000, about 2100, about 2200, about 2300, about 2400 or about 2500 liters) of plasma from 1000 donors with an RSV neutralization antibody titer of 1800 or more. In one embodiment, a pooled plasma composition of the invention comprises about 2200 liters of plasma from 1000 donors with an RSV neutralization antibody titer of 1800 or more, wherein less than 50% of the total volume of the pooled plasma composition (e.g., in preferred embodiments, about 30-45%, 35-45%, 35-40%)) comprises plasma obtained from high titer selected human donors; about 55-70% (e.g., in preferred embodiment, about 55-75%, 55-65%) of the total volume of the pooled plasma composition comprises plasma obtained from non-high titer selected human donors, and about 3-20% of the total volume of the pooled plasma composition comprises plasma from non-selected human donors. In a further embodiment, the pooled plasma composition comprises pathogen-specific antibody titers to at least two or more respiratory pathogens selected from influenza A virus, influenza B virus, parainfluenza virus type 1, parainfluenza virus type 2, metapneumovirus and coronavirus that are each elevated at least about 1.5 fold (e.g., about 1.3, 1.4, 1.5, 1.6, 1.7, 1.8, 1.9, 2.0, 2.5, 3.0 fold or more) compared to a control valued (e.g., the pathogen-specific antibody titers found in a mixture of plasma samples obtained from 1000 or more random human subjects, or the pathogen-specific titers found in a conventional hyperimmune immune globulin (e.g., hyperimmune immune globulin for rabies (HYPERRAB, Grifols, Clayton, N.C.), hyperimmune globulin for hepatitis (e.g., HYPERHEP B, Talecris Biotherapeutics, Research Triangle Park, N.C.), hyperimmune globulin for RSV (e.g., RESPIGAM, MEDIMMUNE, Inc.)). In one embodiment, the pooled plasma composition comprises at least the minimum titer of antibodies to *Corynebacterium diphtheria*, measles virus, and polio virus recommended by the FDA (e.g., see 37 CFR § 640.104). In one embodiment, the pooled plasma composition comprises a respiratory syncytial virus-specific antibody titer that is at least 3 fold greater (e.g., 3, 4, 5, 6, 7, 8, 9, 10 fold or more) than the respiratory syncytial virus-specific antibody titer found in a mixture of plasma samples obtained from 1000 or more random human subjects. In one embodiment, the pooled plasma composition provides a therapeutic benefit to a subject administered the composition that is not achievable via administration of a mixture of plasma samples obtained from 1000 or more random human subjects. Multiple types of therapeutic benefits are provided including, but not limited to, inhibition of infection caused by RSV, influenza A virus, influenza B virus, parainfluenza virus type 1, parainfluenza virus type 2, metapneumovirus and/or coronavirus in a subject administered the composition for a duration of time that is longer than and not achievable in a subject administered a mixture of plasma samples obtained from 1000 or more random human subjects; significant reduction in viral load in the lung and/or nose (e.g., in an immunocompromised subject administered the composition compared to a control subject not receiving the composition); significant reduction in lung histopathology (e.g., in an immunocompromised subject administered the composition compared to a control subject not receiving the composition); and/or significant reduction in the level of pathogenic viral RNA in lung, liver, kidney and/or other tissue (e.g., in an immunocompromised subject administered the composition compared to a control subject not receiving the composition). In one embodiment, the pooled plasma composition lacks detectable levels (e.g., detected using any method known in the art (e.g., recommended by the U.S. Food and Drug Administration)) of human immunodeficiency virus (HIV) 1 (HIV-1), HIV-2, *Treponema pallidum, Plasmodium falciparum, Plasmodium malariae, Plasmodium ovale, Plasmodium vivax, Plasmodium knowlesi*, hepatitis B virus (HBV), hepatitis C virus (HCV), prions, West Nile virus, parvovirus, Typanosoma cruzi, SARS coronavirus, and/or vaccinia virus. In one embodiment, each individual plasma sample used in a process or composition of the invention is collected only at an FDA approved blood establishments and is tested by serological tests (e.g., FDA approved serological tests) for human immunodeficiency virus (HIV) 1 (HIV-1), HIV-2, *Treponema pallidum, Plasmodium falciparum, Plasmodium malariae, Plasmodium ovale, Plasmodium vivax, Plasmodium knowlesi*, hepatitis B virus (HBV), hepatitis C virus (HCV), prions, West Nile virus, parvovirus, Typanosoma cruzi, SARS coronavirus, and/or vaccinia virus. In another embodiment, an individual plasma sample and/or a pooled plasma composition of the invention is tested for the presence of HIV-1, HIV-2, HBV, HCV, or other infectious agent (e.g., pathogen) using Nucleic Acid Testing (NAT) and used in a process or composition of the invention only when the absence of the pathogens is confirmed.

The invention is not limited by the type of subject (e.g., mammal, non-human primate, human, etc.) administered or treated with a composition of the invention (e.g., pooled plasma samples and/or immunotherapeutic composition comprising same). Indeed, the subject may be any subject in need of treatment with a composition of the invention (e.g., a subject infected with or susceptible to infection (e.g., due to an immune deficiency) with an infectious agent (e.g., any one or more infectious agents described herein (e.g., respiratory pathogens))). In some embodiments, the subject is at elevated risk for infection (e.g., by one or multiple specific pathogens (e.g., respiratory pathogens)). The subject may be a neonate. In some embodiments, the subject has an immunodeficiency (e.g., a subject receiving immunosuppressing drugs (e.g., a transplant patient), suffering from a disease of the immune system, suffering from a disease that depresses immune functions, undergoing a therapy (e.g., chemotherapy) that results in a suppressed immune system, experiencing an extended hospital stay, and/or a subject anticipating direct exposure to a pathogen or pathogens. For example, in certain embodiments, an immunocompromised subject is an end stage renal disease (ESRD) patient; cancer patient on immunosuppressive therapy (e.g., chemotherapy, radiation), AIDS patient, diabetic patient, neonate, transplant patient (e.g., HSCT, BMT, Cord Blood, Haploidentical, and/or solid organ transplant patient), patient on immunosuppression therapy (e.g., medical immunosuppression, steroids), patient with PIDD and other immune deficiencies, patient with malfunctioning immune system, autoimmune disease patient, elderly person in an extended care facility, patient with autoimmune disease on immunosuppressive therapy, transplant patient, patient with invasive surgical procedure, burn patient, or other patient in an acute care setting. In some embodiments, the subject treated with the compositions and/or methods of the invention include subjects with a healthy or normal immune system (e.g., that has a bacterial, viral and/or fungal infection). In some embodiments, the subject to be treated is one that has a greater than normal risk of being exposed to an agent or material (e.g., a toxin or toxins). In some embodiments, the subject is a soldier, an emergency responder or other subject that has a higher than normal risk of being exposed to a toxin (e.g., biological toxin), wherein treatment with the compositions and/or methods of the invention provide the subject one or more immune response benefits (e.g., administration of an immunotherapeutic composition to a soldier prevents the soldier from showing signs or symptoms of disease or morbidity normally associated with exposure to a toxin).

The invention thus provides methods and compositions for preventing and/or treating infections associated with bacterial, viral, fungal, and yeast microorganisms. In some embodiments, the invention provides compositions (e.g., kits) and methods for identifying subjects (e.g., subjects vaccinated with one or more bacterial, viral and/or fungal microbial antigens/vaccines) useful for providing donor plasma/serum (e.g., with high titers of bacterial, viral and/or fungal-specific antibodies). In some embodiments, the invention provides new therapeutic compositions for active and passive immunization against infections caused by and/or associated with a microbial (e.g., bacterial, viral, fungal, etc.) pathogens. In some embodiments, the invention provides new therapeutic compositions for active and passive immunization against infections caused by and/or associated with a specific virus (e.g., respiratory syncytial virus), bacteria (e.g., *S. pneumonia*) fungus or yeast. The invention is not limited by the type of infection caused by and/or associated with *S. pneumoniae*. Indeed, compositions and methods of the invention are useful for any and all infections associated with the presence of *S. pneumonia* (e.g., including, but not limited to, pneumoniae, bacteraemia, meningitis, otitis media, etc.). For example, in some embodiments, compositions and methods of the invention are utilized with (e.g., administered to) subjects with an immune deficiency. As described in detail herein, the invention is not limited to any particular immune deficiency. An immune deficiency may be congenital, acquired or the result of immunosuppressive treatment. In some embodiments, the invention provides a therapeutic composition that provides antibodies against microbial infection (e.g., caused by *S. pneumonia*), increases the rate of opsonization and phagocytosis of microbial pathogens (e.g., *S. pneumonia*), and/or induces enhanced intracellular killing of microbial pathogens (e.g., *S. pneumonia*) (e.g., thereby preventing or clearing microbial infection (e.g., *S. pneumoniae* infection)). In some embodiments, the invention provides an immunological serum against a bacteria, virus, yeast and/or fungi (e.g., *S. pneumonia*). In some embodiments, the invention provides plasma/serum that provides humoral and/or cellular immunity against a bacteria, virus, yeast and/or fungi (e.g., *S. pneumonia*). In some embodiments, the humoral and/or cellular immunity is short lived (e.g., 5 weeks, 4 weeks, 3 weeks, 2 weeks, or less). In some embodiments, the humoral and/or cellular immunity lasts 5, 6, 7, 8, 9, 10, 11, 12, 13 14, 15, 16 or more weeks.

In some embodiments, plasma (e.g., a plasma pool (e.g., obtained from a donor or plurality of donors (e.g., one or more donors vaccinated with the same or different microbial antigen (e.g., virus, bacterium and/or fungus)))) is prepared or selected that has a high titer of antibodies to a specific microorganism (e.g., a virus, bacterium and/or fungus). In some embodiments, plasma (e.g., a plasma pool (e.g., obtained from a donor or plurality of donors (e.g., one or more donors vaccinated with the same or different microbial antigen (e.g., virus, bacterium and/or fungus antigen)))) is prepared or selected that has a high titer of antibodies to two or more microorganisms (e.g., two or more specific viruses, bacteria and/or fungi). In some embodiments, plasma (e.g., a plasma pool (e.g., obtained from a donor or plurality of donors (e.g., one or more donors vaccinated with the same or different microbial antigen (e.g., virus, bacterium and/or fungus antigen)))) is prepared or selected that has a high titer of antibodies specific for 3, 4, 5, 6, 7, 8, 9, 10, 11, 12, 13, 14, 15, 16, 17, 18, 19, 20, 21, 22, 23 or more different microbial antigens (e.g., 3, 4, 5, 6, 7, 8, 9, 10, 11, 12, 13, 14, 15, 16, 17, 18, 19, 20, 21, 22, 23 or more different, specific viruses, bacteria and/or fungi (e.g., serotypes of *S. pneumonia*

DEFINITIONS

Figure 1:
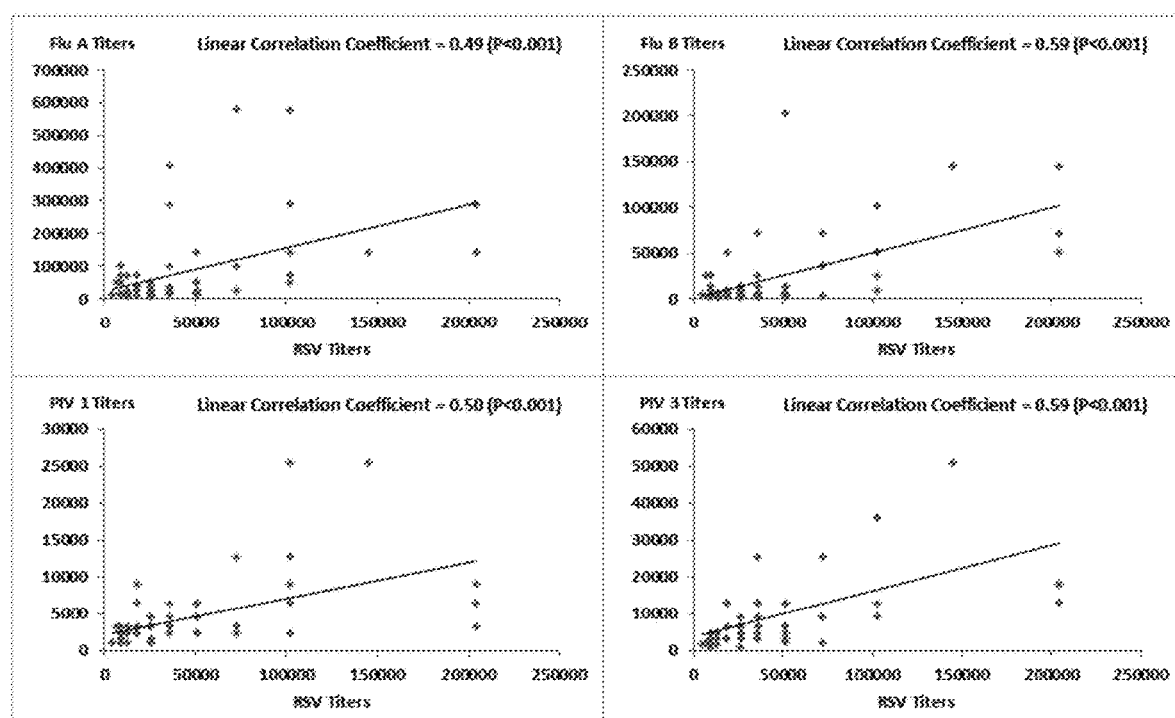
FIG. 1 shows scatter plots of titers to RSV and titers to Flu A, Flu B, PIV 1 and PIV 3 in Linear Scale

As used herein, the term "subject" refers to any human or animal (e.g., non-human primate, rodent, feline, canine, bovine, porcine, equine, etc.).

As used herein, the term "sample" is used in its broadest sense and encompass materials obtained from any source. As used herein, the term "sample" is used to refer to materials obtained from a biological source, for example, obtained from animals (including humans), and encompasses any fluids, solids and tissues. In particular embodiments of this invention, biological samples include blood and blood products such as plasma, serum and the like.

However, these examples are not to be construed as limiting the types of samples that find use with the present invention.

As used herein, the term "antibody" refers to an immunoglobulin molecule that is typically composed of two identical pairs of polypeptide chains, each pair having one "light" (L) chain and one "heavy" (H) chain. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 3 or more amino acids. Each heavy chain is comprised of a heavy chain variable region (abbreviated herein as HCVR or $V_H$) and a heavy chain constant region. The heavy chain constant region is comprised of three domains, $C_{H1}$, $C_{H2}$ and $C_{H3}$. Each light chain is comprised of a light chain variable region (abbreviated herein as LCVR or $V_L$) and a light chain constant region. The light chain constant region is comprised of one domain, CL. The constant regions of the antibodies may mediate the binding of the immunoglobulin to host tissues or factors, including various cells of the immune system (e.g., effector cells) and the first component (C1q) of the classical complement system. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of each heavy/light chain pair ($V_H$ and $V_L$), respectively, form the antibody binding site. The term "antibody" encompasses an antibody that is part of an antibody multimer (a multimeric form of antibodies), such as dimers, trimers, or higher-order multimers of monomeric antibodies. It also encompasses an antibody that is linked or attached to, or otherwise physically or functionally associated with, a non-antibody moiety. Further, the term "antibody" is not limited by any particular method of producing the antibody. For example, it includes, inter alia, recombinant antibodies, synthetic antibodies, monoclonal antibodies, polyclonal antibodies, bi-specific antibodies, and multi-specific antibodies.

As used herein, the term "antibody derivative" or "derivative" of an antibody refers to a molecule that is capable of binding to the same antigen that the antibody from which it is derived binds to and comprises an amino acid sequence that is the same or similar to the antibody linked to an additional molecular entity. The amino acid sequence of the antibody that is contained in the antibody derivative may be the full-length antibody, or may be any portion or portions of a full-length antibody. The additional molecular entity may be a chemical or biological molecule. Examples of additional molecular entities include chemical groups, amino acids, peptides, proteins (such as enzymes, antibodies), and chemical compounds. The additional molecular entity may have any utility, such as for use as a detection agent, label, marker, pharmaceutical or therapeutic agent. The amino acid sequence of an antibody may be attached or linked to the additional entity by chemical coupling, genetic fusion, noncovalent association or otherwise. The term "antibody derivative" also encompasses chimeric antibodies, humanized antibodies, and molecules that are derived from modifications of the amino acid sequences of an antibody, such as conservation amino acid substitutions, additions, and insertions.

As used herein, the term "antigen" refers to any substance that is capable of inducing an adaptive immune response. An antigen may be whole cell (e.g. bacterial cell), virus, fungus, or an antigenic portion or component thereof. Examples of antigens include, but are not limited to, microbial pathogens, bacteria, viruses, proteins, glycoproteins, lipoproteins, peptides, glycopeptides, lipopeptides, toxoids, carbohydrates, tumor-specific antigens, and antigenic portions or components thereof.

As used herein, the term "antigen-binding fragment" of an antibody refers to one or more portions of a full-length antibody that retain the ability to bind to the same antigen that the antibody binds to.

As used herein, the terms "immunoglobulin," "immunoglobulin molecule" and "IG" encompass (1) antibodies, (2) antigen-binding fragments of an antibody, and (3) derivatives of an antibody, each as defined herein. As described herein, immunoglobulin may be prepared from (e.g., fractionated from, isolated from, purified from, concentrated from, etc.) pooled plasma compositions (e.g., for administration to a subject). As used herein, the term "Intravenous immunoglobulin (IVIG)" refers to conventional immunoglobulin prepared from the plasma of over one thousand random human donors, whereas the term "IVIG of the invention," for example RSV-IVIG described herein, and in particular, in the Examples, refers to immune globulin prepared from one thousand or more human donors, according to methods of the invention, that contains an elevated RSV specific antibody titer and an elevated antibody titer for one or more other respiratory pathogens (e.g., parainfluenza virus 1, parainfluenza virus 2, coronavirus OC43 and/or coronavirus 229E) compared to a control sample (e.g., conventional IVIG prepared from a mixture of plasma samples obtained from 1000 or more random human plasma donors). As used herein, the terms "hyperimmune globulin," "hyperimmune serum globulin" and "hyperimmune immune globulin" refer to immune serum globulin having a high titer of antibodies specific for a single organism or antigen (e.g., specific for hepatitis, specific for tetanus, specific for rabies, or specific for varicella zoster) produced from plasma or serum obtained from a donor(s) that has an elevated antibody titer for the single, specific organism or antigen. For example, Varicella Zoster Immune Globulin (VZIG, Massachusetts Public Health Biologic Laboratories, Boston, Mass.; or VARIZIG, Cangene Corporation, Winnipeg, Canada)) is a purified human immune globulin that has a high antibody titer specific for varicella zoster prepared from several hundred plasma donors and lacks significant antibody titers, or has decreased antibody titers, for other organisms or antigens (e.g., measles). Other hyperimmune globulin products are generally produced from donors that have been immunized to the specific pathogen or antigen (e.g., Rabies Immune Globulin, HYPERRAB, Grifols, Clayton, N.C., produced from a few hundred or less donors immunized with rabies vaccine). Commercially available hyperimmune globulin products do not meet FDA specifications for infusion into certain patient populations (e.g., immune deficient patients).

As used herein, the term "antibody sample" refers to an antibody-containing composition (e.g., fluid (e.g., plasma, blood, purified antibodies, blood or plasma fractions, blood or plasma components etc.)) taken from or provided by a donor (e.g., natural source) or obtained from a synthetic, recombinant, other in vitro source, or from a commercial source. The antibody sample may exhibit elevated titer of a particular antibody or set of antibodies based on the pathogenic/antigenic exposures (e.g., natural exposure or through vaccination) of the donor or the antibodies engineered to be produced in the synthetic, recombinant, or in vitro context. Herein, an antibody sample with elevated titer of antibody X is referred to as an "X-elevated antibody sample." For example, an antibody sample with elevated titer of antibodies against cytomegalovirus is referred to as a "cytomegalovirus-elevated antibody sample."

As used herein, the term "isolated antibody" or "isolated binding molecule" refers to an antibody or binding molecule that is identified and separated from at least one contaminant with which it is ordinarily associated in its source. Examples of an isolated antibody include: an antibody that: (1) is not associated with one or more naturally associated components that accompany it in its natural state; (2) is substantially free of other proteins from its origin source; or (3) is expressed recombinantly, in vitro, or cell-free, or is produced synthetically and the is removed the environment in which it was produced.

As used herein, the terms "pooled plasma," "pooled plasma samples" and "pooled plasma composition" refer to a mixture of two or more plasma samples and/or a composition prepared from same (e.g., immunoglobulin). Elevated titer of a particular antibody or set of antibodies in pooled plasma reflects the elevated titers of the antibody samples that make up the pooled plasma. For example, plasma samples may be obtained from subjects that have been vaccinated (e.g., with a vaccine) or that have naturally high titers of antibodies to one or more pathogens as compared to the antibody level(s) found in the population as a whole. Upon pooling of the plasma samples, a pooled plasma composition is produced (e.g., that has elevated titer of antibodies specific to a particular pathogen). Herein, a pooled plasma with elevated titer of antibody X (e.g., wherein "X" is a microbial pathogen) is referred to as "X-elevated antibody pool." For example, a pooled plasma with elevated titer of antibodies against cytomegalovirus is referred to as "cytomegalovirus-elevated antibody pool." Also used herein is the term "primary antibody pool" which refers to a mixture of two or more plasma samples. Elevated titer of a particular antibody or set of antibodies in a primary antibody pool reflects the elevated titers of the antibody samples that make up the primary antibody pool. For example, many plasma donations may be obtained from subjects that have been vaccinated (e.g., with a polyvalent *Pseudomonas aeruginosa* vaccine). Upon pooling of the plasma samples, a primary antibody pool is produced that has elevated titer of antibodies to *Pseudomonas aeruginosa*. Herein, a primary antibody pool with elevated titer of antibody X (e.g., wherein "X" is a microbial pathogen) is referred to as "X-elevated antibody pool." For example, a primary antibody pool with elevated titer of antibodies against cytomegalovirus is referred to as "cytomegalovirus-elevated antibody pool." Pooled plasma compositions can be used to prepare immunoglobulin (e.g., that is subsequently administered to a subject) via methods known in the art (e.g., fractionation, purification, isolation, etc.). The invention provides that both pooled plasma compositions and immunoglobulin prepared from same may be administered to a subject to provide prophylactic and/or therapeutic benefits to the subject. Accordingly, the term pooled plasma composition may refer to immunoglobulin prepared from pooled plasma/pooled plasma samples.

As used herein, the term "secondary antibody pool" or "tailored antibody pool" refer to a mixture of two or more primary antibody pools. Such a pool for example, may be tailored to exhibit elevated titer of specific antibodies or sets of antibodies by combining primary pools that exhibit such elevated titers. For example, a primary pool with elevated titer of *Pseudomonas aeruginosa* antibodies could be combined with a primary pool with elevated titer of Varicella-zoster virus antibodies to produce a tailored antibody pool with elevated titer of antibodies against *Pseudomonas aeruginosa* and Varicella-zoster virus.

As used herein, the term, "spiked antibody pool" refers to a pooled plasma sample (e.g., primary or tailored antibody pool) that contains antibodies from at least one natural source spiked or combined with antibodies or other immunoglobulin produced synthetically, recombinantly, or through other in vitro means.

As used herein, the term "isolated antibody" or "isolated binding molecule" refers to an antibody or binding molecule that is identified and separated from at least one contaminant with which it is ordinarily associated in its source. Examples of an isolated antibody include: an antibody that: (1) is not associated with one or more naturally associated components that accompany it in its natural state; (2) is substantially free of other proteins from its origin source; or (3) is expressed recombinantly, in vitro, or cell-free, or is produced synthetically and the is removed the environment in which it was produced.

As used herein, the term "purified" or "to purify" means the result of any process that removes some of a contaminant from the component of interest, such as a protein (e.g., antibody) or nucleic acid. The percent of a purified component is thereby increased in the sample.

As used herein, the term "immunotherapeutic agents" refers to a chemical or biological substance that can enhance an immune response (e.g., specific or general) of a mammal.

Examples of immunotherapeutic agents include: passively administered primary antibody pools; tailored antibody pools (e.g., passively administered tailored antibody pools); vaccines, chemokines, antibodies, antibody fragments, bacillus Calmette-Guerin (BCG); cytokines such as interferons; vaccines such as MyVax personalized immunotherapy, Onyvax-P, Oncophage, GRNVAC1, FavId, Provenge, GVAX, Lovaxin C, BiovaxID, GMXX, and NeuVax; and antibodies such as alemtuzumab (CAMPATH), bevacizumab (AVASTIN), cetuximab (ERBITUX), gemtuzumab ozogamicin (MYLOTARG), ibritumomab tiuxetan (ZEVALIN), panitumumab (VECTIBIX), rituximab (RITUXAN, MABTHERA), trastuzumab (HERCEPTIN), tositumomab (BEXXAR), tremelimumab, CAT-3888, agonist antibodies to CD40 receptor that are disclosed in WO2003/040170, and any immunomodulating substance.

As used herein, the term "donor" refers to a subject that provides a biological sample (e.g., blood, plasma, etc.). A donor/donor sample may be screened for the presence or absence of specific pathogens (e.g., using U.S. Food and Drug Administration (FDA) guidelines for assessing safety standards for blood products (e.g., issued by the FDA Blood Products Advisory Committee). For example, a donor/donor sample may be screened according to FDA guidelines to verify the absence of one or more bloodborne pathogens (e.g., human immunodeficiency virus (HIV) 1 (HIV-1), HIV-2; *Treponema pallidum* (syphilis); *Plasmodium falciparum, P. malariae, P. ovale, P. vivax* or *P. knowlesi* (malaria); hepatitis B virus (HBV), hepatitis C virus HCV); prions (Creutzfeldt Jakob disease); West Nile virus; parvovirus; *Typanosoma cruzi*; SARS coronavirus (SARS); vaccinia virus or other pathogen routinely screened or that is recommended to be screed for by a regulatory body such as the FDA). As used herein, the terms "selected donor," "selected human subject" and the like refer to a subject that is chosen and/or identified to provide a biological sample (e.g., blood, plasma, etc.) based on the presence of a desired characteristic of that biological sample (e.g., a specific titer (e.g., high, average or low titer) of antibodies (e.g., determined using one or more screening methods (e.g., neutralization assay or other assay described herein) specific for one or more pathogens (e.g., one or more respiratory pathogens (e.g., respiratory syncytial virus))). For example, in one embodiment described herein, a high titer selected donor (e.g., identified by characterizing the specific titer of antibodies to respiratory syncytial virus via a first, plasma screening assay utilized to assess RSV neutralizing activity in a donor plasma sample; and a second screening assay characterizing the specific antibody titer of the purified immunoglobulin fraction of each donor plasma sample identified as displaying the top 20% of neutralizing activity using the first, plasma screening assay, wherein a purified immunoglobulin fraction possessing an RSV neutralization titer of 1800 or above is used to categorize a plasma sample as a high titer selected donor) comprises a pathogen specific antibody titer that is about 1.5-2.0 times, 2-5 times, 5-8 times, 8-10 times, 10-14 times, 14 times or greater than a standard value (the titer of pathogen specific antibodies present in a pool of plasma samples from 1000 or more random human subjects), wherein medium titer donors comprise a pathogen specific antibody titer that is the titer of pathogen specific antibodies present in a pool of plasma samples from 1000 or more random human subjects or that is only marginally higher (e.g., 5-20% higher) or marginally lower (e.g., 5-20% lower) than this value, and wherein low titer donors comprise a pathogen specific antibody titer that is around 20-50 percent the titer of pathogen specific antibodies present in a pool of plasma samples from 1000 or more random human subjects. As used herein, a "non-selected donor," "random donor," "random human subject" and the like, when used in reference to a donor sample (e.g., blood, plasma, etc.) used for generating a pool of donor samples), refer to a subject that provides a biological sample (e.g., blood, plasma, etc.) without specific knowledge of characteristics (e.g., antibody titer to one or more pathogens) of that sample. Thus, a random donor/random donor sample may be a subject/sample that passes FDA bloodborne pathogen screening requirements and is not selected on the basis of antibody titers (e.g., respiratory pathogen specific antibody titers). In one embodiment described herein, the titer for non-tested/non-selected source donor/donor sample is set at zero. If biological samples from a group of selected donors selected for the same characteristic are pooled, the pool so generated (e.g., a primary pool) will be enhanced for the selected characteristic. On the other hand, if biological samples from a group of non-selected, random donors are pooled, random differences between the biological samples will be averaged out, and the pool so generated (e.g., the primary pool) will not be enhanced for any specific characteristic. It is preferred that both random donors/random donor samples and selected donors/selected donor samples are screened (e.g., using FDA screening requirements) to verify the absence of bloodborne pathogens (e.g., prior to and/or after pooling). Furthermore, according to one embodiment of the invention, and as described in detail herein, biological samples (e.g., plasma samples) from one or more selected donors can be mixed with biological samples (e.g., plasma samples) from one or more other selected donors (e.g., selected for the same or different characteristic (e.g., the same or different titer (e.g., high, medium or low titer) of antibodies to a specific pathogen) and/or mixed with biological samples (e.g., plasma samples) from one or more non-selected donors in order to generate a pooled plasma composition (e.g., that contains a desired, standardized level of antibodies for one or more specific pathogens (e.g., one or more respiratory pathogens)).

As used herein, an "immunostimulatory amount" refers to that amount of a vaccine (e.g., viral, bacterial and/or fungal vaccine) that is able to stimulate the immune response. An immune response includes the set of biological effects leading to the body's production of immunoglobulins, or antibodies, in response to a foreign entity. Accordingly, immune response refers to the activation of B cells, in vivo or in culture, through stimulation of B cell surface Ig receptor molecules. The measurement of the immune response is within the ordinary skill of those in this art and includes the determination of antibody levels using methods described in the series by P. Tijssen, Laboratory Techniques in Biochemistry and Molecular Biology: Practice and Theory of Enzyme Immunoassays, (Burdon & van Knippenberg eds., 3rd ed., 1985) Elsevier, New York; and Antibodies: A Laboratory Manual, (Harlow & Lane eds., 1988), Cold Spring Harbor Laboratory Press; as well as procedures such as countercurrent immuno-electrophoresis (GIEP), radioimmunoassay, radio-immunoprecipitation, enzyme-linked immuno-sorbent assays (ELISA), dot blot assays, and sandwich assays, see U.S. Pat. Nos. 4,376,110 and 4,486,530, all of which are incorporated by reference. Measurement of the immune response also includes detection or determination of B cell activation events that may precede antibody production, or signal an increase in antibody production. Such measurements include, B cell proliferation assays, phosphorylation assays, assays of intracytoplasmic free calcium concentration, and other methods of determining B cell activation known in the art. Representative assays are provided in Mongini et al., J. Immunol. 159:3782-91 (1997); Frade, et al., BBRC 188:833-842 (1992); Tsokos et al., J. Immunol. 144:1640-1645 (1990); Delcayre et al., BBRC 159:1213-1220 (1989); and Nemerow et al., J. Immunol. 135:3068-73 (1985) each of which is incorporated by reference. In preferred embodiments, the practice of the invention includes promoting, enhancing or stimulating an immune response. These actions refer to establishing an immune response that did not previously exist; to optimizing or increasing a desired immune response; to establishing or increasing a secondary response characterized by increased isotype switching, memory response, or both; to providing a statistically increased immunoprotective effect against a pathogen; to generating an equivalent or greater humoral immune response, or other measure of B cell activation, from a reduced or limiting dose of antigen; to generating an increased humoral immune response, or other measure of B cell activation, in response to an equivalent dose of antigen; or to lowering the affinity threshold for B cell activation in vivo or in vitro. Preferably, an immunostimulatory amount refers to that amount of vaccine that is able to stimulate an immune response in a subject (e.g., a donor), and from which subject plasma, serum or other blood component is harvested for use in the compositions and methods of the invention (e.g., for the therapeutic and/or prophylactic treatment of microbial (e.g., viral, bacterial and/or fungal) infection in a subject treated with compositions and methods described herein)).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "adjuvant" refers to any substance that can stimulate an immune response (e.g., a mucosal immune response). Some adjuvants can cause activation of a cell of the immune system (e.g., an adjuvant can cause an immune cell to produce and secrete a cytokine). Examples of adjuvants that can cause activation of a cell of the immune system include, but are not limited to, the nanoemulsion formulations described herein, saponins purified from the bark of the *Q. saponaria* tree, such as QS21 (a glycolipid that elutes in the 21st peak with HPLC fractionation; Aquila Biopharmaceuticals, Inc., Worcester, Mass.); poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); cholera toxin (CT), and Leishmania elongation factor (a purified Leishmania protein; Corixa Corporation, Seattle, Wash.). Traditional adjuvants are well known in the art and include, for example, aluminum phosphate or hydroxide salts ("alum"). In some embodiments, compositions of the present invention are administered with one or more adjuvants (e.g., to skew the immune response towards a Th1 and/or Th2 type response). In some embodiments, an adjuvants described in US2005158329; US2009010964; US2004047882; or U.S. Pat. No. 6,262,029 (each of which is hereby incorporated by reference in its entirety) is utilized.

As used herein, the term "an amount effective to induce an immune response" (e.g., of a composition for inducing an immune response), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route.

As used herein, the term "under conditions such that said subject generates an immune response" refers to any qualitative or quantitative induction, generation, and/or stimulation of an immune response (e.g., innate or acquired).

A used herein, the term "immune response" refers to a response by the immune system of a subject. For example, immune responses include, but are not limited to, a detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the terms "immunogen" and "antigen" refer to an agent (e.g., a microorganism (e.g., bacterium, virus or fungus) and/or portion or component thereof (e.g., a protein antigen or a polysaccharide)) that is capable of eliciting an immune response in a subject.

As used herein, the term Streptococcus (e.g., S. pneumoniae) antigen refers to a component or product of a bacteria of the genus Streptococcus that elicits an immune response when administered to a subject.

As used herein, the term "pathogen product" refers to any component or product derived from a pathogen including, but not limited to, polypeptides, peptides, proteins, nucleic acids, membrane fractions, and polysaccharides.

The terms "pharmaceutically acceptable" or "pharmacologically acceptable," as used herein, refer to compositions that do not substantially produce adverse reactions (e.g., toxic, allergic or immunological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintrigrants (e.g., potato starch or sodium starch glycolate), polyethyl glycol, other natural and non-naturally occurring carries, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts. Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as Nat, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the terms "at risk for infection" and "at risk for disease" refer to a subject that is predisposed to experiencing a particular infection or disease (e.g., respiratory infection or disease). This predisposition may be genetic (e.g., a particular genetic tendency to experience the disease, such as heritable disorders), or due to other factors (e.g., immunosuppression, compromised immune system, immunodeficiency, environmental conditions, exposures to detrimental compounds present in the environment, etc.). Thus, it is not intended that the present invention be limited to any particular risk (e.g., a subject may be "at risk for disease" simply by being exposed to and interacting with other people), nor is it intended that the present invention be limited to any particular disease.

DETAILED DESCRIPTION OF THE INVENTION

The present invention relates to compositions and methods for the treatment of immunodeficiency (e.g., primary immunodeficiency disease). In particular, the invention provides pooled human plasma compositions and/or immunoglobulin prepared from same, methods of identifying human plasma for use in the compositions, methods of manufacturing (e.g., utilizing pooling and blending methods described herein) the compositions, and methods of utilizing the compositions (e.g., for prophylactic administration and/or therapeutic treatment (e.g., passive immunization (e.g., immune-prophylaxis))).

Immunoglobulin obtained from the plasma of thousands of different donors contains antibodies to many of the pathogens that these individuals have encountered in their lifetime. However, a significant limitation exists. Since immunoglobulin is pooled from thousands of donors the antibody titers to the many infectious organisms (e.g., microbial pathogens) for which protection is sought varies greatly and is very often not sufficient to meet the immune needs in case of an infection (e.g., with a pathogen) in an immune suppressed individual.

Hyperimmune serum globulins (immune serum globulin having high titers of a particular antibody), in distinction to normal immunoglobulin, have been therapeutically useful in treating patients who require immediate infusion of high titer antibodies. For example, tetanus hyperimmune globulin is useful in treating patients who may have suspected tetanus and rabies hyperimmune globulin for treating patients with suspected rabies. Hyperimmune serum globulins can be produced from plasma or serum obtained from a selected donor(s) who have elevated titers for a specific antibody than is normally found in the average population (that is not found at a high titer in the average population). These donors have either been recently immunized with a particular vaccine (See, e.g., U.S. Pat. No. 4,174,388) or else they have recently recovered from an infection or disease (See, e.g., Stiehm, Pediatrics, Vol. 63, No. 1, 301-319 (1979); herein incorporated by reference in its entirety). These high titer sera or plasmas are pooled and subjected to fractionation procedures (Cohn et al, J. Am. Chem. Soc., 68, 459 (1946); Oncley, et al, J. Am. Chem. Soc., 71, 541 (1949); herein incorporated by reference in their entireties). Such procedures have required specific selection of a donor or limited numbers of donors in order to produce hyperimmune globulin with elevated concentrations of the desired antibodies.

Many different microorganisms are commonly found in the human upper respiratory system. *S. pneumoniae* is one such example, While *S. pneumoniae* is part of the normal upper respiratory tract flora, as with many natural flora, it can become pathogenic under certain conditions (e.g., if the immune system of the host is suppressed). This is the case with other infections as well that become virulent in immune suppressed hosts.

Cytomegalovirus (CMV) is a genus of viruses, some of which have the potential to infect humans and cause disease. While infection is not common among the general population, it is encountered very frequently in certain susceptible groups of patients. Immunosuppressed organ transplant and cancer patients have been identified as having an unusually high risk of acquiring severe, and sometimes fatal, CMV infection.

Respiratory syncytial virus (RSV) is considered the most important cause of severe respiratory disease in infants and young children. It can also be an important cause of lower respiratory tract disease in the elderly, hematopoietic stem cell transplant patients and organ transplant patients. In the United States alone it has been reported that this virus causes pneumonia, bronchitis and croup in approximately 4 million children each year, resulting in about 4500 deaths. In the western world it is the major cause for hospitalization of children (National Research Council News Report, 35, 9 (1985); Stott, E. J. et al, Archives of Virology, 84:1-52 (1985); and W. H. O. Scientific Group, World Health Organization Technical Report Series 642 (1980); herein incorporated by reference in their entireties).

Varicella-zoster virus (VZV) is the cause of clinical disease that, although not common among the general population, is encountered frequently in certain susceptible groups of patients. Immunosuppressed organ transplant and cancer patients have been identified as having an unusually high risk of acquiring severe, and frequently fatal, VZV infection. Zaia et al in The Journal of Infectious Diseases, Vol. 137, No. 5, 601-604 (1978) disclosed a practical method for preparation of VZV immune globulin for intramuscular administration. Outdated blood was screened for complement-fixing antibody to VZV. About 15% of the plasma units had a complement-fixation titer equal to or greater than 1:16, with about 7.5% greater than or equal to 1:32.

*Pseudomonas aeruginosa* (*P. aeruginosa*) is a common bacterium that can cause disease in animals, including humans. Although infection with *P. aeruginosa* is not common among the general population, *P. aeruginosa* infection is encountered very frequently in certain susceptible groups of patients. Burn victims, immunosuppressed cancer patients, and individuals with extended hospital stays have been identified as having an unusually high risk of acquiring severe, and sometimes fatal disease caused by *P. aeruginosa*. James et al, in The Lancet, 13 Dec. 1980, 1263-1265 (herein incorporated by reference in its entirety), described passive immunization of burn patients at risk of septicaemia. The immunization was accomplished with an immunoglobulin prepared from plasma from healthy human volunteers vaccinated with a polyvalent *Pseudomonas* vaccine.

The present invention relates to compositions and methods for the treatment of immunodeficiency (e.g., primary immunodeficiency disease). In particular, the invention provides pooled human plasma immunoglobulin compositions, methods of identifying human plasma for use in the compositions, methods of manufacturing the compositions, and methods of utilizing the compositions (e.g., for prophylactic administration and/or therapeutic treatment (e.g., passive immunization (e.g., immune-prophylaxis))). In one embodiment, the invention provides a composition comprising pooled plasma samples obtained from 1000 or more human subjects, wherein the pooled plasma comprises elevated levels, compared to the pathogen-specific antibody titers found in a mixture of plasma samples obtained from 1000 or more random human subjects, of pathogen-specific antibody titers to one or more respiratory pathogens. The invention is not limited by the type of respiratory pathogens for which the pooled plasma comprises elevated levels of pathogen-specific antibody titers. The pooled plasma composition may comprise elevated levels of pathogen-specific antibody titers to one or more of respiratory syncytial virus, influenza A virus, influenza B virus, parainfluenza virus type 1, parainfluenza virus type 2, metapneumovirus, coronavirus, *S. pneumonia, H. influenza, L. pneumophila*, group A *Streptococcus*, or any other respiratory pathogen known by those of ordinary skill in the art or described herein. In certain embodiments, the invention provides a composition comprising pooled plasma samples for passive immunization of patients susceptible to, or suffering from, infection (e.g., bacterial infection (e.g., associated with *Streptococcus pneumonia, Haemophilus* influenza, etc.), viral infection (e.g., associated with adenovirus, herpes virus, influenza virus, rhinovirus, etc.), fungal infection (e.g., associated with *Aspergillus fumigatus, Cladosporium* or other fungi) and/or exposure to microbial toxins and/or harmful agents (e.g., animal venom))).

Accordingly, disclosed herein are methods and compositions for the passive immunization of subjects infected with or who are susceptible to infection, disease or harm from various pathogens (e.g., pathogenic bacteria (e.g., *S. aureus, P. aeruginosa*, etc.), pathogenic viruses (e.g., RSV, CMV, etc.), pathogenic eukaryotes, toxins (e.g., bacterial toxins (e.g., Botulinum neurotoxin, Tetanus toxin, *Clostridium difficile* toxin, *E. coli* toxin, *Vibrio* RTX toxin, Staphylococcal toxins, Cyanobacteria toxin), fungal toxins, e.g. mycotoxins)), etc. Methods include, for example, the blending and/or pooling of plasma samples to generate a composition comprising pooled plasma samples (e.g., from 1000 or more donor subjects) comprising specific, elevated levels of pathogen-specific antibody titers and/or immunoglobulin prepared from same (e.g., for the treatment of infection wherein administration (e.g., infusion) of conventional IVIG would not provide sufficient antibody levels required to treat a specific infection). The pooled plasma composition may comprise elevated levels, compared to a control value (e.g., the levels of pathogen-specific antibody titers in 1000 or more random donor plasma samples), of pathogen-specific antibody titers to one or more of respiratory syncytial virus, influenza A virus, influenza B virus, parainfluenza virus type 1, parainfluenza virus type 2, metapneumovirus, coronavirus, *S. pneumonia, H. influenza, L. pneumophila*, group A *Streptococcus*, or any other respiratory or other type of pathogen known by those of ordinary skill in the art or described herein. In one embodiment, donor plasma samples that contain high antibody titers to a specific respiratory pathogen (e.g., RSV) are identified, selected and blended with other donor plasma samples that do not contain high antibody titers to a specific respiratory pathogen (e.g., RSV) in order to generate a pool of at least 1000 donor plasma samples, wherein the pool contains a desired (e.g., standardized, elevated) antibody titer to one or more specific respiratory pathogens (e.g., RSV), in the absence of having to utilize 1000 high titer donors. For example, in some embodiments, the identification, selection and blending processes of the invention allow generation of pooled plasma samples from at least 1000 donors, wherein the pooled plasma contains a desired (e.g., standardized, elevated) antibody titer to one or more specific respiratory pathogens (e.g., RSV), wherein less than about 50% (e.g., 50-45%, 45-40%, 40-35%, 35-30%, 30-25%, 25-20% or fewer) of the donors are identified as high titer for RSV and/or other respiratory pathogen specific antibodies. In one embodiment, a pooled plasma composition (e.g., pooled plasma samples or immunoglobulin prepared from same) is provided wherein the pooled plasma composition contains plasma from 1000 or more donors, wherein about 40-50% of the donor plasma samples have high titer for RSV and/or other respiratory pathogen specific antibodies, 20-30% of the donor plasma samples contain a medium titer for RSV and/or other respiratory pathogen specific antibodies, and 20-40% of the donor plasma samples have low titer for RSV and/or other respiratory pathogen specific antibodies. In another embodiment, plasma samples from 1000 or more (e.g., 1000, 1000-1500, 1500-2000, 2000-3000, 3000-4000, 4000-6000, 6000-8000 or more) human subjects are characterized for antibody titers (e.g., using one or more assays described herein (e.g., using a first neutralization or other type of assay described herein and/or a second neutralization or other type of assay described herein)) to one or more respiratory viruses selected from respiratory syncytial virus, influenza A virus, influenza B virus, parainfluenza virus type 1, parainfluenza virus type 2, metapneumovirus, coronavirus, *S. pneumonia, H. influenza, L. pneumophila*, and group A *Streptococcus*; the subjects are categorized as high, medium or low titer for the one or more respiratory viruses; plasma samples are obtained from a subset of the subjects identified as high, medium or low titer; and plasma samples from at least 500 (e.g., at least 500, 550, 600, 650, 700, 750, 800, 850, 900, 950, 1000, 1050, 1100, 1150, 1200 or more) subjects so identified are blended together in order to generate a pooled plasma composition (e.g., comprising a desired, elevated antibody titer to one or more of respiratory viruses selected from respiratory syncytial virus, influenza A virus, influenza B virus, parainfluenza virus type 1, parainfluenza virus type 2, metapneumovirus, coronavirus, *S. pneumonia, H. influenza, L. pneumophila*, and group A *Streptococcus*).

In one embodiment, identifying antibody titer comprises a first, plasma screening assay assessing neutralizing activity/titer (e.g., RSV neutralizing activity) in a plasma sample, and a second screening assay assessing antibody titer in a purified immunoglobulin fraction of the plasma sample (e.g., specific RSV antibody titer in the purified immunoglobulin fraction). In one embodiment, neutralizing activity in plasma is measured via the absence of infection of hepatocytes. In a further embodiment, the first plasma screening assay assessing neutralization activity categorizes plasma samples as high titer, medium titer, or low titer for RSV specific antibodies, wherein a high titer RSV donor/donor sample is one having an anti-RSV titer of about 7800 or greater, a medium titer RSV donor/donor sample is one having an anti-RSV titer of about 3300-7799, and a low titer RSV donor/donor sample is one having an anti-RSV titer of about 1800-3299 (e.g., titer being calculated and assigned to a donor/donor sample as the dilution that give 50% inhibition of virus growth/infection of hepatocytes (that point which is 50% of the two extremes (saline plus virus is 100 growth and no virus added is 0 growth) according to methods described herein). In still a further embodiment, only plasma samples identified as displaying the top 20% of neutralizing activity are processed to produce purified immunoglobulin and subsequently screened using the second screening assay. In one embodiment, the second screening assay characterizes the RSV specific antibody titer of a purified immunoglobulin fraction of the plasma sample. In a preferred embodiment, a donor/donor sample that has an RSV neutralization titer of 1800 in a purified immunoglobulin fraction of the plasma sample is scored as a high titer donor. In a preferred embodiment, an RSV neutralization titer of 1800 is used to identify a donor/donor sample (e.g., plasma sample) comprising elevated antibody titers for one or more respiratory pathogens selected from influenza A virus, influenza B virus, parainfluenza virus type 1, parainfluenza virus type 2, metapneumovirus and coronavirus compared to the antibody titer in a control (e.g., the respiratory pathogen specific antibody titer present in a pool of plasma samples from 1000 or more random human subjects). In another embodiment, the pooled plasma composition comprises an RSV neutralization antibody titer of 1800 or more.

In one embodiment, when plasma samples are blended from 1000 or more subjects, less than half (e.g., about 10-20%, 20-30%, 30-40%, 40-50%) of the 1000 or more donors are from subjects categorized as high titer (e.g., using the above described first and second screening assays) for the one or more respiratory viruses (e.g., RSV). For example, in a preferred embodiment, when plasma samples are blended from 1000 or more subjects, only about 40-50% (e.g., 400-500) of the plasma samples are from subjects categorized as high titer (e.g., using the above described first and second screening assays) for the one or more respiratory viruses (e.g., RSV) and the remainder are characterized as not being high titer (e.g., for the one or more respiratory viruses (e.g., RSV). In another preferred embodiment, when plasma samples are blended from 1000 or more subjects, only about 40-45% (e.g., 400-450) of the plasma samples are from subjects categorized as high titer for the one or more respiratory viruses. In preferred embodiments, 30-45%, 35-45%, 40-45% of the 1000 or more plasma samples are from high titer selected human donors.

In one embodiment, when plasma samples are blended from 1000 or more subjects, only about 30-45%, 35-45%, or 30-40% of the plasma samples are from subjects categorized as high titer (e.g., using the sequential first and second screening assays described herein) for RSV antibodies, about 55-75% or about 55-65% are from non-high titer selected donors, and about 3-30% or about 3-20% are from non-selected donors.

In one embodiment, less than 50% of the total volume of the pooled plasma composition (e.g., in preferred embodiments, about 30-45%, 35-45%, 35-40%)) comprises plasma obtained from high titer selected human donors; about 55-70% (e.g., in preferred embodiment, about 55-75%, 55-65%) of the total volume of the pooled plasma composition comprises plasma obtained from non-high titer selected human donors, and about 3-20% of the total volume of the pooled plasma composition comprises plasma from non-selected human donors.

In one embodiment, when plasma samples are blended from 1000 or more subjects, the blended plasma or immunoglobulin obtained (e.g., fractionated) from same contains seroprotective antibody titers to measles, diphtheria and polio (e.g., contain antibody titers to measles, diphtheria and polio that provide a subject administered the blended plasma composition or immunoglobulin obtained from same serum levels of antibodies specific for measles, diphtheria and polio to prevent, or protect from, infection with same). In another embodiment, when plasma samples are blended from 1000 or more subjects, the blended plasma or immunoglobulin obtained (e.g., fractionated) from same contains seroprotective antibody titers to measles, diphtheria, polio, tetanus and/or varicella (e.g., contain antibody titers to measles, diphtheria, polio, tetanus and/or varicella that provide a subject administered the blended plasma composition or immunoglobulin obtained from same serum levels of antibodies specific for measles, diphtheria, polio, tetanus and/or varicella to prevent, or protect from, infection with same (e.g., meets the antibody titer levels recommended by U.S. Food and Drug Administration (e.g., for the treatment of immune deficiency disease and/or treatment of or prevention of infection in an immune deficient subject))). In another embodiment, the pooled plasma comprises elevated levels, compared to the pathogen-specific antibody titers found in a mixture of plasma samples obtained from 1000 or more random human subjects, of pathogen-specific antibody titers to two, three, four or more respiratory pathogens described herein. In one embodiment, the pooled plasma comprises a respiratory syncytial virus-specific antibody titer that is at least 2 fold greater (e.g. 2 fold, 3 fold, 4 fold, 5 fold 6 fold, 7 fold, 8 fold, 9 fold, 10 fold, 12 fold, 15 fold or more) than the respiratory syncytial virus-specific antibody titer found in a mixture of plasma samples obtained from 1000 or more random human subjects. In another embodiment, the pooled plasma comprises pathogen-specific antibody titers to at least two or more respiratory pathogens selected from respiratory syncytial virus, influenza A virus, influenza B virus, parainfluenza virus type 1, parainfluenza virus type 2, metapneumovirus, coronavirus, *S. pneumonia, H. influenza, L. pneumophila*, and group A *Streptococcus* that are each elevated at least 1.5 fold compared to the pathogen-specific antibody titers found in a mixture of plasma samples obtained from 1000 or more random human subjects. In another embodiment, the pooled plasma comprises pathogen-specific antibody titers to at least three or more respiratory pathogens selected from respiratory syncytial virus, influenza A virus, influenza B virus, parainfluenza virus type 1, parainfluenza virus type 2, metapneumovirus, coronavirus, *S. pneumonia, H. influenza, L. pneumophila*, and group A *Streptococcus* that are each elevated at least 1.5 fold compared to the pathogen-specific antibody titers found in a mixture of plasma samples obtained from 1000 or more random human subjects. In still another embodiment, the pooled plasma comprises pathogen-specific antibody titers to at least four or more respiratory pathogens selected from respiratory syncytial virus, influenza A virus, influenza B virus, parainfluenza virus type 1, parainfluenza virus type 2, metapneumovirus, coronavirus, *S. pneumonia, H. influenza, L. pneumophila*, and group A *Streptococcus* that are each elevated at least 1.5 fold compared to the pathogen-specific antibody titers found in a mixture of plasma samples obtained from 1000 or more random human subjects. In one embodiment, the pooled plasma comprises plasma samples obtained from 1000-3000 or more (e.g., more than 1000, 1250, 1500, 1750, 2000, 2500, 3000, 3500, 4000 or more human subjects). In one embodiment, the pooled plasma is utilized to prepare immunoglobulin (e.g., for intravenous administration to a subject). In one embodiment, the pooled plasma and/or immunoglobulin provides a therapeutic benefit to a subject administered the pooled plasma and/or immunoglobulin that is not achievable via administration of a mixture of plasma samples (or immunoglobulin prepared from same) obtained from 1000 or more random human subjects. The invention is not limited by the type of therapeutic benefit provided. Indeed, a variety of therapeutic benefits may be attained including those described herein. In one embodiment, the pooled plasma and/or immunoglobulin possesses enhanced viral neutralization properties compared to a mixture of plasma samples obtained from 1000 or more random human subjects or immunoglobulin prepared from same. For example, in one embodiment, the pooled plasma possesses enhanced viral neutralization properties against one or more (e.g., two, three, four, five or more) respiratory pathogens (e.g., described herein). In a further embodiment, the enhanced viral neutralization properties reduce and/or prevent infection in a subject administered the composition for a duration of time that is longer than, and not achievable in, a subject administered a mixture of plasma samples obtained from 1000 or more random human subjects. In one embodiment, the pooled plasma and/or immunoglobulin prepared from same reduces the incidence of infection in a subject administered the composition. In another embodiment, a pooled plasma and/or immunoglobulin prepared from same reduces the number of days a subject administered the pooled plasma and/or immunoglobulin is required to be administered antibiotics (e.g., to treat infection). In yet another embodiment, a pooled plasma and/or immunoglobulin prepared from same increases the trough level of circulating anti-respiratory pathogen specific antibodies in a subject (e.g., increases the level of neutralizing titers specific for respiratory pathogens (e.g., thereby providing protective levels of anti-respiratory pathogen specific antibodies between scheduled dates of administration of the pooled plasma and/or immunoglobulin prepared from same that are not maintained in a subject administered a mixture of plasma samples obtained from 1000 or more random human subjects or immunoglobulin prepared from same)). In one embodiment, the composition comprising pooled plasma samples further comprises a pharmaceutically acceptable carrier (e.g., any natural or non-naturally occurring carrier(s) known in the art). In one embodiment, a subject administered immunoglobulin prepared from pooled plasma according to the invention displays a mean fold increase in anti-RSV neutralization titer that is at least 4 fold, at least 5 fold, at least 6 fold, at least 7 fold, at least 8 fold, at least 9 fold or more at a time point of at least 1 to 14 days post administration (e.g., 14 day, 15 days, 16 days, 17 days, 18 days, 19 days or more) of the immunoglobulin. The invention is not limited by the amount of immunoglobulin administered to a subject. In one embodiment, a subject is administered between 100-5000 mg/kg of the immunoglobulin one time, or daily for two or more days (e.g., 2, 3, 4, or more consecutive days). In another embodiment, such doses are administered intermittently, e.g. every week, every two weeks, every three weeks, every four weeks, etc. In one embodiment, a subject is administered between 750-1500 mg/kg of immunoglobulin on day one and between 750-1500 mg/kg immunoglobulin on day 2. In one embodiment, a subject is administered 1500 mg/kg of immunoglobulin on day one and 750 mg/kg immunoglobulin on day 2. In another embodiment, a subject is administered 750 mg/kg of immunoglobulin on day one and 750 mg/kg immunoglobulin on day 2. In one embodiments, a subject is administered immunoglobulin on day one, optionally administered immunoglobulin on day 2, and then re-administered immunoglobulin every 21 days. In one embodiments, a subject is administered immunoglobulin on day one, optionally administered immunoglobulin on day 2, and then re-administered immunoglobulin every 28 days. In one embodiment, the pooled plasma and/or immunoglobulin prepared from same reduces the incidence of infection in a subject administered the composition. In another embodiment, a pooled plasma and/or immunoglobulin prepared from same reduces the number of days a subject administered the pooled plasma and/or immunoglobulin is required to be administered antibiotics (e.g., to treat infection). In yet another embodiment, a pooled plasma and/or immunoglobulin prepared from same increases the trough level of circulating anti-respiratory pathogen specific antibodies and increases the trough level of circulating anti-measles, anti-diphtheria, anti-polio, anti-tetanus and/or anti-varicella specific antibodies in a subject (e.g., increases the level of neutralizing titers specific for respiratory pathogens and measles, diphtheria, polio, tetanus, and/or varicella (e.g., thereby providing protective levels of anti-respiratory pathogen specific antibodies and anti-measles, anti-diphtheria, anti-polio, anti-tetanus and/or anti-varicella specific antibodies between scheduled dates of administration of the pooled plasma and/or immunoglobulin prepared from same that are not maintained in a subject administered a mixture of plasma samples obtained from 1000 or more random human subjects or immunoglobulin prepared from same)).

In one embodiment, the invention provides that the detection of high antibody titer within a donor plasma sample to one or more respiratory pathogens (e.g., RSV) can be used to identify (e.g., as a biomarker) a plasma donor as a high/strong responder to antigen challenge (e.g., that possesses high antibody titers (e.g., to a plurality of respiratory pathogens)) via generation of elevated levels of antibodies, versus donors that are not strong responders/do not generate elevated levels of antibodies (e.g., that possess medium to low antibody titers) (e.g., See Example 1). Thus, in one embodiment, the invention provides a method of identifying a plasma donor as a high/strong responder to antigen challenge comprising obtaining a plasma sample from the subject, characterizing the pathogen-specific antibody titer within the plasma for one or more respiratory pathogens selected from respiratory syncytial virus, influenza A virus, influenza B virus, parainfluenza virus type 1, parainfluenza virus type 2, metapneumovirus and coronavirus; and identifying the subject as a high/strong responder to antigen challenge if the plasma contains elevated levels (e.g., at least 1.5 fold (e.g., 2, 3, 4, 5, 6, 7, 8, 9, 10, 11, 12, 13, 14, 15, 16, 17, 18, 19, 20 fold or more), compared to the pathogen-specific antibody titers found in a mixture of plasma samples obtained from 1000 or more random human subjects, of pathogen-specific antibody titers to the one or more respiratory pathogens. In one embodiment, the plasma comprises elevated levels of pathogen-specific neutralizing antibody titers to at least two or more respiratory pathogens selected from respiratory syncytial virus, influenza A virus, influenza B virus, parainfluenza virus type 1, parainfluenza virus type 2, metapneumovirus and coronavirus, that are each elevated at least 1.5 fold (e.g., 2, 3, 4, 5, 6, 7, 8, 9, 10, 11, 12, 13, 14, 15, 16, 17, 18, 19, 20 fold or more) compared to the pathogen-specific antibody titers found in a mixture of plasma samples obtained from 1000 or more random human subjects. In a further embodiment, the invention provides a method of using the level of a respiratory pathogen specific neutralizing antibody titer (e.g., RSV neutralizing antibody titer) detected in a plasma donor sample as a biomarker as an indication of the level of respiratory pathogen specific neutralizing antibody titers within the sample to one or more of influenza A virus, influenza B virus, parainfluenza virus type 1, parainfluenza virus type 2, metapneumovirus and coronavirus (e.g., for the identification, selection and blending/mixing of plasma samples).

Plasma obtained from one or a plurality of donors identified as a high/strong responder (e.g., containing high neutralizing antibody titers) can be used, together with plasma from one or a plurality of donors identified as not being high/strong responder (e.g., do not have high neutralizing antibody titers) in order to generate a mixture of plasma samples possessing a desired characteristic. For example, in one embodiment, the invention provides a method of producing a pooled plasma composition comprising obtaining plasma samples from human subjects; characterizing the pathogen-specific antibody titer, within a subset of the plasma samples, for one or more respiratory pathogens selected from respiratory syncytial virus, influenza A virus, influenza B virus, parainfluenza virus type 1, parainfluenza virus type 2, metapneumovirus and coronavirus; selecting, based upon the antibody titers characterized, plasma samples that have elevated levels, compared to the pathogen-specific antibody titers found in a mixture of plasma samples obtained from 1000 or more random human subjects, of pathogen-specific antibody titers to one or more respiratory pathogens selected from respiratory syncytial virus, influenza A virus, influenza B virus, parainfluenza virus type 1, parainfluenza virus type 2, metapneumovirus and coronavirus; pooling the selected plasma samples with other plasma samples to generate the pooled plasma composition, wherein the pooled plasma composition comprises pathogen-specific antibody titers to at least two or more respiratory pathogens selected from respiratory syncytial virus, influenza A virus, influenza B virus, parainfluenza virus type 1, parainfluenza virus type 2, metapneumovirus and coronavirus, that are each elevated at least 1.5 fold compared to the pathogen-specific antibody titers found in a mixture of plasma samples obtained from 1000 or more random human subjects. In a preferred embodiment, 1000 or more plasma samples categorized according to the methods described herein are pooled in order to generate the pooled plasma composition (See, e.g., Example 2).

As described in Examples 3 and 4, use of a composition of the invention (e.g., immunoglobulin prepared from plasma pooled using selection processes of the invention) provide clinical efficacy and improved outcomes in subjects.

Immunotherapeutic compositions of the invention were tested in a cotton rat model of human immunodeficiency. Therapeutic as well as prophylactic potential was assessed. For analysis of therapeutic potential, immunoglobulin prepared as described in Example 2 was administered therapeutically to immunosuppressed (cyclophosphamide treated) and normal cotton rats challenged with RSV/A/Long (See Example 3).

Immunosuppression in cyclophosphamide-treated groups (A, B, C, and G) was verified by significant decrease in whole blood cell and lymphocyte counts compared to normal cotton rats (groups D, E, and F). Immunosuppressed animals treated with IVIG of the invention, groups B and C, showed significant reduction in lung and nose viral load at day 4 post infections (p.i). and day 10 post infection. compared to RSV-infected immunosuppressed animals treated with saline (group A) (See Example 3). This reduction was accompanied by reduction in lung histopathology and a decrease in the detection of viral RNA in lung, liver, and kidney samples of group B and C animals on day 10 post infection. Treatment of normal cotton rats with IVIG of the invention also resulted in significant reduction of RSV load in the lungs and nose of IGIV-treated animals (groups E and F) compared to saline-treated (group D) animals on day 4 p.i. (See Example 3).

Immunotherapeutic compositions of the invention were also tested in a cotton rat model of human immunodeficiency for prophylactic potential (See Example 4). Immunosuppression was verified by significant decrease in whole blood cell and lymphocyte counts, and reduction in serum total IgG. Immunosuppressed animals treated with IVIG of the invention showed undetectable lung viral replication at day 4 p.i., and almost complete reduction in the prolonged viral replication caused by immunosuppression measured on day 10 (only two out of 5 animals in a group showed minimal viral replication (See Example 4)). This reduction was accompanied by reduction in lung histopathology and decrease in the detection of viral RNA in lung, kidney, and liver samples of selected immunosuppressed animals.

While an understanding of a mechanism is not necessary to practice the present invention, and while the invention is not limited to any particular mechanism, in one embodiment, methods of identifying and selecting high titer respiratory pathogen antibody titers (e.g., specific for RSV) in a subject's plasma of the invention identify and/or select subject's that in general have an immune response system that generates high levels of respiratory pathogen specific antibodies compared to other subjects that do not display high titer respiratory pathogen antibody titers (e.g., towards RSV) and do not generate high levels of respiratory pathogen specific antibodies. The immune response gene that encodes for the magnitude of humoral antibody responses to microbial antigens is under the control of the major histocompatibility complex (HLA). In this context the donors who were selected based on their high responses to RSV are, in some embodiments, high responders to other respiratory viruses. While an understanding of a mechanism is not necessary to practice the present invention, and while the invention is not limited to any particular mechanism, in one embodiment, a high response to respiratory pathogens is due to donors being exposed by virtue of their occupation or other demographic considerations (e.g., such that not only is a subject repeatedly exposed to RSV infection but also to exposure or infection with other common respiratory viruses). Thus, in some embodiments, a subject's immunological history accounts for the fact that the subject has elevated titers to multiple common respiratory viruses.

In certain embodiments, plasma and/or antibody samples comprise donated and/or purchased body fluid samples, for example individual blood or blood component samples (e.g., plasma). These samples may be purified and/or screened for the presence of pathogens or other impurities (e.g., before or after pooling). Multiple donor antibody samples (e.g., donor plasma samples or other antibody-containing samples) can pooled together to create a pooled plasma sample/primary antibody pool (e.g., after identifying or screening for desired antibody titer in the antibody samples). By combining individual antibody samples (e.g., blood or blood component (e.g., plasma) samples) which have higher than normal titers of antibodies to one or more selected antigens, epitopes, extracellular proteins, viral surface proteins, together with plasma taken from donors not selected for high titers, a pooled plasma sample/primary antibody pool is created that exhibits elevated titer for such antibodies. In some embodiments, selected antigens, epitopes, extracellular proteins, viral surface proteins, etc. are administered to subjects to induce the expression of desired antibodies (e.g., from which antibody samples can be harvested). The resulting enhanced high titer antibody sample (e.g., blood, serum, plasma, purified antibodies (e.g., containing higher antibody titer as compared to a control level (e.g., the antibody titer in pooled plasma samples from 1000 or more random human subjects)) is recovered and pooled with antibody samples from other subjects exhibiting or anticipated to exhibit elevated titer for the same antibodies (or antibodies directed to the same antigens, extracellular proteins, viral surface proteins, etc.), or with antibody samples from subject that have not been screened for antibody titer or that possess a low or absent antibody titer to a specific pathogen. In some embodiments, the pooled antibody samples are purified, screened, and/or concentrated. In one embodiment, pooling of samples (e.g., 1000 or more samples) occurs in a manner that uses the fewest possible number of samples from high titer donors (e.g., identified by the compositions and methods described herein) but that still maintains a desired, standardized and elevated antibody titer to one or more (e.g., two, three, four or more) respiratory pathogens described herein.

Certain embodiments of the invention utilize plasma from subjects that have been administered immunogenic substances (e.g., vaccines, antigens, epitopes, extracellular proteins, viral surface proteins, etc) in order to generate elevated levels of specific neutralizing antibodies within the subject. The invention is not limited by the type of antigen (e.g., *S. pneumoniae* antigen) used for administration to a subject (e.g., donor) to induce the expression of specific antibodies. In some embodiments, the antigen is a *S. pneumoniae* antigen or fragment or component thereof. In some embodiments, the antigen is a polysaccharide (e.g., unconjugated or conjugated to a carrier or protein) or a plurality of the same. In some embodiments, the antigen (e.g., *S. pneumoniae* antigen) is a S vaccine comprising components capable of inducing specific antibodies (e.g., antibodies that are specific to multiple different serotypes of *S. pneumonia*). In some embodiments, a vaccine is a commercially available vaccine. The invention is not limited by the vaccine. Indeed, a variety of vaccines (e.g., *S. pneumoniae* vaccines) may be utilized including, but not limited to, PREVNAR, SYNFLORIX, PNEUMOVAX as well as others known in the art. Similarly, the invention is not limited by the type or route of administration/immunization. Indeed, any route/type of immunization may be utilized including, but not limited to, the methods described in U.S. Patent Publication Nos. US2008026002; US2007009542; US2002094338; US2005070876; US2002010428; US2009047353; US2008066739; and US2002038111), each of which is hereby incorporated by reference in its entirety. In like manner, the invention is not limited by the vaccine formulation (e.g., of a S. pneumoniae vaccine). Indeed, any formulation may be utilized including, but not limited to, those described in US2002107265, hereby incorporated by reference in its entirety. In some embodiments, the vaccine is a multivalent vaccine in which additional antigens are added (See, e.g. US2007161088; US2006121059, each of which is hereby incorporated by reference in its entirety.). In some embodiments, mirobial antigens are purified prior to use in a vaccine (e.g., a conjugate vaccine) (See, e.g., US2008286838 hereby incorporated by reference in its entirety). Methods of culture of microorganisms useful in a process of manufacturing a pneumococcal conjugate vaccines are described in US2010290996, hereby incorporated by reference in its entirety. Alternatively, in some embodiments, antigens (e.g., S. pneumonia antigens) are utilized that are not conjugated to a carrier protein (See, e.g., US2009136547, hereby incorporated by reference in its entirety). In some embodiments, immunomodulators are utilized (See, e.g., US2004156857; U.S. Pat. No. 5,985,264; and WO11041691, each of which is hereby incorporated by reference in its entirety). In some embodiments, therapeutic antibodies are produced in a donor administered an antigen (e.g., an S. pneumoniae antigen) and/or vaccine according to the methods described in WO05070458; US2009191217; and WO10094720, each of which is hereby incorporated by reference in its entirety. In some embodiments, antigens (e.g., vaccines (e.g., conjugate or unconjugated vaccines)) are used to generate antibodies (e.g., present in serum and/or plasma) that are useful against infectious disease organisms (e.g., as described in, for example, US2003099672; WO0062802, each of which is hereby incorporated by reference in its entirety).

In some embodiments, a polysaccharide vaccine is used (e.g., containing multiple S. pneumoniae serotypes (e.g., containing purified polysaccharides from 1, 2, 3, 4, or more or all 23 of the following S. pneumoniae serotypes: 1, 2, 3, 4, 5, 6b, 7F, 8, 9N, 9V, 10A, 11A, 12F, 14, 15B, 17F, 18C, 19F, 19A, 20, 22F, 23F and 33F). Although an understanding of a mechanism is not needed to practice the present invention, and while the present invention is not limited to any particular mechanism of action, in some embodiments, an antigen (e.g., a S. pneumoniae antigen) or vaccine that stimulates B-cells (e.g., plasma cells) to generate and secrete specific (e.g., S. pneumonia-specific) immunoglobulin (e.g., S. pneumonia-specific IgM) without the assistance of T cells finds use in the invention.

In some embodiments, a conjugated vaccine is utilized that contains capsular polysaccharides (e.g., from a plurality of S. pneumoniae serotypes) that is covalently bound to a carrier and/or adjuvant (e.g., the diphtheria toxoid CRM197). Although an understanding of a mechanism is not needed to practice the present invention, and while the present invention is not limited to any particular mechanism of action, in some embodiments, any antigen (e.g., S. pneumoniae antigen) or vaccine that stimulates B-cells (e.g., plasma cells) to generate and secrete specific (e.g., S. pneu-monia-specific) immunoglobulin (e.g., S. pneumonia-specific IgM and/or IgG) via interaction with specific type 2 helper T cells) and/or production of memory B cells (e.g., S. pneumonia-specific memory B cells) finds use in the invention.

Thus, in some embodiments, the invention provides methods of stimulating high antibody levels in a donor, which includes administering to an animal, for example a human, a pharmaceutically-acceptable composition comprising an immunologically effective amount of an antigen composition (e.g., an S. pneumoniae antigen composition). The composition can include partially or significantly purified antigens (e.g., S. pneumoniae antigens (e.g., polysaccharide, protein and/or peptide epitopes, obtained from natural or recombinant sources, which may be obtained naturally or either chemically synthesized, or alternatively produced in vitro from recombinant host cells expressing DNA segments encoding such epitopes)).

Methods to determine the efficacy of immunization (e.g., determining the level of S. pneumonia-specific antibody titers) are known in the art, and any known method may be utilized to assess the efficacy of immunization. In some embodiments, detection methods for the evaluation of the efficacy of a vaccine (e.g., a pneumococcal conjugate vaccine) is used as described in, for example, US2005260694; U.S. Pat. Nos. 4,308,026; 4,185,084; or US2005208608, each of which is hereby incorporated by reference in its entirety.

In some embodiments, kits and methods are provided that identify samples and/or pools with specific antibody titers (e.g., antibody titers that are elevated). In one embodiment, a suitable amount of a detection reagent (e.g., antibody specific for antibodies, an antigen, or other reagent known in the art) is immobilized on a solid support and labeled with a detectable agent. Antibodies can be immobilized to a variety of solid substrates by known methods. Suitable solid support substrates include materials having a membrane or coating supported by or attached to sticks, beads, cups, flat packs, or other solid support. Other solid substrates include cell culture plates, ELISA plates, tubes, and polymeric membranes. The antibodies can be labeled with a detectable agent such as a fluorochrome, a radioactive label, biotin, or another enzyme, such as horseradish peroxidase, alkaline phosphatase and 2-galactosidase. If the detection reagent is an enzyme, a means for detecting the detection reagent can be supplied with the kit. A suitable means for detecting a detectable agent employs an enzyme as a detectable agent and an enzyme substrate that changes color upon contact with the enzyme. The kit can also contain a means to evaluate the product of the assay, for example, a color chart, or numerical reference chart. Some suitable methods for characterizing samples and pools are provided in the references incorporated by reference herein. The present invention is not limited by the method used to characterize samples and pools as having elevated titer.

In certain embodiments, compositions are provided (e.g., antibody samples, pooled plasma samples, immunoglobulins, etc.) in which antibodies have been purified and/or isolated from one or more contaminants. Human immunoglobulins were first isolated on a large scale during the 1940's by F. J. Cohn. In some embodiments, the techniques provided by Cohn (Cohn et al., J. Am. Chem. Soc. 1946; 68:459-475; herein incorporated by reference in its entirety) or modified Cohn-techniques are utilized in preparation of immunoglobulins herein. In some embodiments, various purification and isolation methods are utilized to produce substantially unmodified, unaltered, non-denatured and/or native immunoglobulin molecules of high purity.

Exemplary techniques are provided, for example, in U.S. Pat. No. 4,482,483, herein incorporated by reference in its entirety. In some embodiments, compositions (e.g., antibody pools) comprise >50% immunoglobulin (e.g., >60%, >70%, >80%, >90%, >95%, >99%). Various methods may be utilized for producing such compositions, including, for example, standard protein purification and isolation techniques as well as fractionation of biological fluids (e.g., plasma). Descriptions of fractionation of antibodies for use in immunotherapeutics are found, for example in U.S. Pat. No. 4,346,073 and other references provided herein, each of which is incorporated by reference in their entireties. In certain embodiments, immunoglobulins are purified by a fractional precipitation method, ion-exchange chromatography, size exclusion chromatography, ultrafiltration, affinity chromatography, or any suitable combinations thereof (See, e.g., U.S. Pat. Nos. 7,597,891; 4,256,631; 4,305,870; Lullau et al., J. Biol. Chem. 1996; 271:16300-16309; Corthesy, Biochem. Soc. Trans. 1997; 25:471-475; and Crottet et al., Biochem. J. 1999; 341:299-306; herein incorporated by reference in their entireties).

In some embodiments, plasma samples are pooled to produce a large volume of antibodies/immunoglobulins (e.g., for commercial, clinical, therapeutic, and/or research use). In particular embodiments, antibody samples (e.g., plasma samples) exhibiting a certain desired characteristic or characteristics are pooled to result in a primary antibody pool (e.g., pooled plasma samples) enhanced for, exhibiting, and/or enriched in that desired characteristic. In certain embodiments, antibody samples (e.g., plasma) obtained from multiple subjects (e.g., >2 subjects, >5, >10 subjects, >20 subjects, >100 subjects, >200 subjects, >500 subjects, >1,000 subjects, >2,000 subjects, >5,000 subjects, >10,000 subjects, or more) are pooled. The subjects from which the antibody samples (e.g., blood, plasma, etc.) may be obtained may have had recent exposure to a pathogen, antigen, or epitope, been recently vaccinated with a pathogen, antigen, or epitope, or have been specifically exposed to a pathogen, antigen, or epitope for the purpose of producing specific antibodies.

In some embodiments, methods are provided for pooling/combining primary antibody pools (e.g., pooled plasma samples) to produce secondary antibody pools or tailored antibody pools. Two or more primary antibody pools, each exhibiting a desired characteristic (e.g., antibodies against RSV, antibodies against influenza, etc.), are combined at a desired ratio to produce a tailored antibody pool. In some embodiments, a tailored antibody pool exhibits the relative sum of the characteristics of the primary antibody pools from which it is derived (e.g., tailored pool confers immunity to specific pathogens to an extent that is consistent with the relative amount of the primary pools from which it is derived). In other embodiments, a tailored antibody pool exhibits distinct characteristics from the primary antibody pools from which it is derived (e.g., tailored pool confers immunity to a specific pathogen to a greater extent than the primary pools from which it is derived used individually, provides enhanced general immunity compared to use of individual primary pools, provides enhanced anti-inflammatory benefit compared to use of individual primary pools).

A composition of the invention (e.g., pooled plasma and/or immunoglobulin prepared from same) can be administered by any suitable means, including parenteral, subcutaneous, intraperitoneal, intrapulmonary, and, if desired for local treatment, intralesional administration. Parenteral infusions include intramuscular, intravenous, intraarterial, intraperitoneal, or subcutaneous administration. In addition, compositions of the invention may be administered by pulse infusion, particularly with declining doses. Dosing can be by any suitable route, e.g. by injections, such as intravenous or subcutaneous injections, depending in part on whether the administration is acute or chronic.

A composition of the invention may be formulated, dosed, and/or administered in a fashion consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners. Compositions of the invention need not be, but optionally are formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a composition of the invention (when used alone or in combination with one or more other additional therapeutic agents) may depend upon a number of factors including the type of disease to be treated, the type of antibody, the patient's size, body surface area, age, the particular compound to be administered, sex, time and route of administration, general health, interaction with other drugs being concurrently administered, the severity and course of the disease, whether the antibody is administered for preventive or therapeutic purposes, previous therapy, and the patient's clinical history.

An exact dosage may be determined by the individual physician in view of the patient to be treated. Dosage and administration are adjusted to provide sufficient levels of the active moiety (e.g., plasma pool) or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks, four weeks, six weeks, eight weeks or more, depending on half-life and clearance rate of the particular formulation.

A composition of the invention may be administered to the patient at one time or over a series of treatments. Depending on the type and severity of the disease, about 1 µg/kg to 5000 mg/kg (e.g. 0.5 mg/kg-1500 mg/kg) of a composition of the invention can be an initial candidate dosage for administration to the patient, whether, for example, by one or more separate administrations, or by continuous infusion. As described herein, additional drugs or agents (e.g., antibiotics, antivirals, anti-inflammatory and/or healing compounds) may be administered concurrently with a pooled plasma composition of the invention. An exemplary daily dosage of such agent may range from about 1 µg/kg to 100 mg/kg or more. For repeated administrations over several days or longer, depending on the condition, the treatment can generally be sustained until a desired suppression of disease symptoms occurs. One exemplary dosage of a composition of the invention would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to a patient. Such doses may be administered intermittently, e.g. every week or every two or three weeks. A medical practitioner is readily able to monitor the therapeutic administration of a composition of the invention and can in turn determine if higher or lower doses of the composition is to be administered.

Compositions of the invention may be administered (e.g., intravenously, orally, intramuscularly, subcutaneously, etc.) to a patient in a pharmaceutically acceptable carrier such as physiological saline. Such methods are well known to those of ordinary skill in the art.

Accordingly, in some embodiments of the present invention, a composition of the invention can be administered to a patient alone, or in combination with other drugs or in pharmaceutical compositions where it is mixed with excipient(s) or other pharmaceutically acceptable carriers. In one embodiment of the present invention, the pharmaceutically acceptable carrier is pharmaceutically inert. Depending on the condition being treated, pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, a composition of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the compositions of the present invention (e.g., pharmaceutical compositions) can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of a composition of the invention may be that amount that results in the inhibition of growth and/or killing of bacteria in a subject. Determination of effective amounts is well within the capability of those skilled in the art, especially in light of the disclosure provided herein.

In addition to the active ingredients pharmaceutical compositions may contain suitable pharmaceutically acceptable carriers comprising excipients and auxiliaries that facilitate processing of the compositions of the invention into preparations which can be used pharmaceutically.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the compositions in water-soluble form. Additionally, suspensions of the compositions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compositions to allow for the preparation of highly concentrated solutions.

Compositions of the invention formulated in a pharmaceutical acceptable carrier may be prepared, placed in an appropriate container, and labeled for treatment of an indicated condition. Conditions indicated on the label may include treatment or prevention of a viral or bacterial infection.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-% mannitol at a pH range of 4.5 to 5.5 that is combined with buffer prior to use.

Compositions of the present invention (e.g., pooled plasma samples) can be combined with additional agents (e.g., antibodies, antibody fragments, antibody-like molecules, monoclonal antibodies, or other proteins or small molecules) to enhance the immunotherapeutic and/or anti-inflammatory affect. Such additional agents may be produced recombinantly, synthetically, in vitro, etc. The present invention is not limited by the types of additional agents that a pooled antibody sample or other sample is combined with. In some embodiments, recombinant or synthetic antibodies (e.g., humanized monoclonals) or antibody fragments (e.g., directed to a specific pathogen or antigen) are added. In addition, antibodies (e.g., monoclonal, polyclonal, etc.) for specified bacteria and viruses can be added to the compositions. In some embodiments, various therapeutics (e.g., anti-inflammatory agents, chemotherapeutics), stabilizers, buffers, etc. are added to the antibody sample pools, for example, to further enhance the efficacy, stability, administerability, duration of action, range of uses, etc.

Compositions may optionally contain carriers such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the immunoglobulins can be brought about by the use of agents delaying absorption, for example, aluminum monostearate and gelatin.

In some embodiments, a composition of the invention is administered to a subject to provide therapeutic, preventative, prophylactic, and/or other benefits.

In some embodiments, an immunotherapeutic composition of the invention (e.g., with elevated of antibodies against two or more pathogens, antigens or epitopes, etc.)) is effective in treating (e.g., therapeutically, preventatively, prophylactically, etc.), bind antigens from, and/or are directed to pathogentic bacteria including, but not limited to: *Bacillus anthracis, Bordetella pertussis, Borrelia burgdorferi, Brucella abortus, Brucella canis, Brucella melitensis, Brucella suis, Campylobacter jejuni, Chlamydia pneumonia, Chlamydia trachomatis, Chlamydophila psittaci,*

*Clostridium botulinum, Clostridium difficile, Clostridium perfringens, Clostridium tetani, Corynebacterium diphtheria, Enterococcus faecalis, Enterococcus faecium, Escherichia coli, Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumonia, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumonia, Streptococcus pyogenes, Treponema pallidum, Vibrio cholera*, and *Yersinia pestis*.

In some embodiments, an immunotherapeutic composition of the invention (e.g., with elevated of antibodies against two or more pathogens, antigens or epitopes, etc.)) are effective in treating (e.g., therapeutically, preventatively, prophylactically, etc.), bind antigens from, and/or are directed to pathogentic viruses including, but not limited to: adenovirus, coxsackie virus, Epstein-barr virus, BK virus, hepatitis a virus, hepatitis b virus, hepatitis c virus, herpes simplex virus (type 1), herpes simplex virus (type 2), cytomegalovirus, human herpesvirus (type 8), human immunodeficiency virus (hiv), influenza virus, measles virus, mumps virus, human papillomavirus, parainfluenza virus, poliovirus, rabies virus, respiratory syncytial virus, rubella virus, and varicella-zoster virus.

Diseases and conditions for which administration of the compositions of the invention is to be used therapeutically or prophylactically include, but are not limited to: common variable immunodeficiency, IgA deficiency, human immunodeficiency virus (HIV) infection, bacterial and viral infections such as respiratory tract infection with influenza, respiratory tract infection with respiratory syncytial virus, respiratory tract infection with rhinovirus, respiratory tract infection with adenovirus: protozoan infections such as giadiasis, yeast infections; chronic lymphocytic leukemia; multiple myeloma; macroglobulinemia; chronic bronchitis; broncliectasis; asthma; immune suppression associated with bone marrow transplantation; immune suppression associated with cyclophosphamide administration; immune suppression associated with azathiaprine administration; immune suppression associated with methotrexate administration; immune suppression associated with chlorambucil administration; immune suppression associated with nitrogen mustard administration; immune suppression associated with 6-mercaptopurine administration; immune suppression associated with thioguanine administration; severe combined immunodeficiency; adenosine deaminase deficiency; major histocompatibility class I (Bare leukocyte syndrome) and class II deficiencies; purine nucleoside phosphorylase deficiency; DiGeorge Syndrome; transient hypogammaglobulinemia of infancy; X-linked agammaglobulinemia; X-linked agammaglobulinemia with growth hormone deficiency; transcobalamin II deficiency; immunodeficiency with thymoma; immunodeficiency with hereditary defective response to Epstein Barr virus; immunoglobulin deficiency with increased IgM; P chain deficiency; ataxia telangiectasia; immunodeficiency with partial albinism; sequelae of selective IgA deficiency such as those due to rheumatoid arthritis; juvenile rheumatoid arthritis; systemic lupus erythematosus; thyroiditis; pernicious anemia; dermatomyositis; Coomb's positive hemolytic anemia; idiopathic Addison's disease; cerebral vasculitis and idiopathic thrombocytopenic purpura.

The use of specific compositions and methods of the invention to treat pathogens or treat/prevent infection may vary depending on the site of infection. For example, immunotherapeutic compositions used for treating and/or preventing respiratory infections might include immunoglobulins with antibodies and/or monoclonal antibodies specific for at least two of the following pathogens: respiratory syncytial virus, influenza A virus, influenza B virus, influenza C virus, parainfluenza virus type 1, parainfluenza virus type 2, rhinovirus, metapneumovirus, coronavirus, *S. pneumonia, H. influenza, L. pneumophila*, group A *Streptococcus, Streptococcus mutans, B. gingivalis, S. pyogenes* (group A), *S. pneumoniae, K. pneumoniae, P. aeruginosa, S. aureus, M. pneumoniae*, or any other respiratory or other type of pathogen known by those of ordinary skill in the art or described herein.

Various diseases (e.g., cancer, AIDS, etc.), infections, and treatments (e.g., antivirals, antirejections medications, chemotherapies, etc.) can result in localized or general inflammation in a subject, which can lead to discomfort, downstream health problems, morbidity, and/or death. In some embodiments, compositions and methods of the present invention provide anti-inflammatory benefits when administered to a subject. Pooled immunoglobulins have been shown to provide an anti-inflammatory action when passively administered (See, e.g., Nimmerjahn and Ravetch, Annu. Rev. Immunol. 2008. 26:513-33.; Ramakrishna et al. Plos Pathogens. 2011. 7:6:e1002071.; herein incorporated by reference in their entireties). In some embodiments, a composition of the invention exerts enhanced anti-inflammatory effect (e.g., 10% enhancement, 20% enhancement, 50% enhancement, 2-fold enhancement 3-fold enhancement, 5-fold enhancement, 10-fold enhancement, or greater) compared to the anti-inflammatory effect of a mixture of plasma samples obtained from random human subjects (e.g., 1000 or more random human subjects). Although an understanding of a mechanism is not necessary to practice the present invention and while the present invention is not limited to any particular mechanism, in one embodiment, a pooled plasma composition of the invention displays significantly enhanced anti-inflammatory effect compared to a conventional IVIG because the pooled plasma composition of the invention comprises plasma from at least 1000 donors (e.g., compared to a conventional hyperimmune globulin prepared from a limited number of donors (e.g., in one embodiment, the larger the number of different plasma samples pooled, the more beneficial the anti-inflammatory effect (e.g., the greater the histopathological benefit (e.g., reduction of epithelial cell death)) observed)).

In certain embodiments, compositions of the invention provide treatment and prophylaxis of wounds, burns, nosocomial infections, and oral and respiratory infections. In some embodiments, immunotherapeutic compositions of the invention comprise specific antibody titers against specific pathogens. For example, the antibody titers for specific pathogens in the compositions of the invention may be between 1 and 1000 µg/ml (e.g., 1 µg/ml . . . 2 µg/ml . . . 5 µg/ml . . . 10 µg/ml . . . 20 µg/ml . . . 50 µg/ml . . . 100 µg/ml . . . 200 µg/ml . . . 500 µg/ml . . . 1000.mu.g/ml), although higher and lower titers are contemplated.

In some embodiments, the protective activity of an immunotherapeutic composition comprising a tailored antibody pool is enhanced by further comprising one or more additional agents, including, but not limited to: antibiotics, antivirals, anti-inflammatory and/or healing compounds. For example, biocides, surfactants, bacterial blocking receptor analogues, cytokines, growth factors, macrophage chemotactic agents, cephalosporins, aminoglycosides, fluoroquinolones, etc., can be provided at therapeutically acceptable levels in the compositions of the invention.

In some embodiments of the present invention, compositions of the invention are administered alone, while in other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier must be "acceptable" in the sense that it is compatible with the other ingredients of the formulation and not injurious to the subject.

Compositions of the invention can be administered via any suitable route of administration (e.g., enteral route, parenteral route, etc.). The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. In typical embodiments, compositions are administered to a subject such that they enter the bloodstream (e.g., intravenous administration). In some embodiments, compositions are administered to devices or instruments that will come into contact with a subject's body (e.g., medical devices, bandages, etc.). The antibodies and compositions of the disclosure can be administered using any suitable method, such as by oral ingestion (e.g., pill, tablet, syrup, liquid, elixir, etc.), nasogastric tube, gastrostomy tube, injection (e.g., intravenous), infusion, implantable infusion pump, and osmotic pump. The suitable route and method of administration may vary depending on a number of factors such as the specific antibody or antibodies being used, the rate of absorption desired, specific formulation or dosage form used, type or severity of the disorder being treated, the specific site of action, and conditions of the patient, and can be readily selected by a person skilled in the art The term "therapeutically effective amount" refers to an amount that is effective for an intended therapeutic purpose. For example, in the context of enhancing an immune response, a "therapeutically effective amount" is any amount that is effective in stimulating, evoking, increasing, improving, or augmenting any response of a mammal's immune system. In the context of providing anti-inflammatory action, a "therapeutically effective amount" is any amount that is sufficient to cause any desirable or beneficial reduction in inflammation or prevention of the occurrence of inflammation. The therapeutically effective amount of an antibody usually ranges from about 0.001 to about 5000 mg/kg, and more usually about 0.05 to about 100 mg/kg, of the body weight of the mammal. For example, the amount can be about 0.3 mg/kg, 1 mg/kg, 3 mg/kg, 5 mg/kg, 10 mg/kg, 50 mg/kg, or 100 mg/kg of body weight of the mammal. The precise dosage level to be administered can be readily determined by a person skilled in the art and will depend on a number of factors, such as the type, and severity of the disorder to be treated, the particular binding molecule employed, the route of administration, the time of administration, the duration of the treatment, the particular additional therapy employed, the age, sex, weight, condition, general health and prior medical history of the patient being treated, and like factors well known in the medical arts.

An immunotherapeutic composition, tailored antibody pool, or other composition of the invention is often administered on multiple occasions. Intervals between single doses can be, for example, on the order of hours, days, weeks, months, or years. An exemplary treatment regimen entails administration once per week, once every two weeks, once every three weeks, once every four weeks, once a month, once every 3 months or once every three to 6 months. Example dosage regimens for a immunotherapeutic composition comprising a tailored antibody pool include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks. Other dosages and regimens may be determined by clinicians, researchers, or other practitioners of the invention.

It should be understood that the immunotherapeutic compositions described herein have veterinary applications as well as human health care utility.

EXPERIMENTAL

The following examples are provided in order to demonstrate and further illustrate certain preferred embodiments and aspects of the present invention and are not to be construed as limiting the scope thereof.

Example 1

Studies have shown that the ability of humans to respond to foreign antigens (e.g., microbial pathogens (e.g., naturally occurring or in the form of a vaccine)) is controlled by the major histocompatibility complex (human leukocyte antigen "HLA" type in humans, the major histocompatibility complex of the mouse, H-2, is homologous to HLA in humans). Additional studies have shown that the histocompatibility complex controls the humoral antibody responses generated within a subject against microbial pathogens. Different HLA typing programs have existed for some time and have studied HLA type with regard to various immunological responses in humans (e.g., bone marrow transplant graft and/or rejection, organ transplant, autoimmunity, cancer, and strength of immune response (e.g., humoral immune response) generated by a subject). While HLA typing can be useful in these limited contexts, cost, medical record and other concerns make it unfeasible to HLA type individuals in other contexts.

Experiments were conducted during development of embodiments of the invention in order to determine if a subset of plasma donors could be identified as strong (e.g., high) humoral immune responders in the absence of HLA typing. For example, the identification of individual subjects, or a population of individuals, that are strong humoral immune responders may itself be useful in order to identify individuals as potential plasma donors (e.g., for the manufacture of immunoglobulin). In addition, experiments were conducted in order to determine if individuals could be identified that were strong responders not only to a single microbial pathogen but to a plurality of microbial pathogens (e.g., such an individual, or population of individuals, may contain high titers due to the strength of humoral immune response in the subject, not just to a single microbial pathogen/antigen but to a plurality of microbial pathogens/antigens (e.g., any or all of the microbial pathogens/antigens to which the individual, or population of individuals, had been exposed in the course of their lifetime(s)). Thus, experiments were conducted in an effort to identify plasma donors as generally high responders in the absence of having to tissue type (e.g., HLA type) the donors for a specific histocompatibility gene complex. To this end, plasma donor samples were studied and characterized for antibody titers for one or a plurality respiratory pathogens in order to characterize the donors (e.g., as a high/strong responder to antigen challenge via generation of elevated levels of antibodies versus donors that are not strong responders/do not generate elevated levels of antibodies (e.g., via determining antibody titers to one or more respiratory pathogens in the subjects)).

Respiratory pathogens were chosen because individuals are ubiquitously exposed to a plurality of respiratory pathogens. That is, almost all adult and pediatric human populations have been exposed to a plurality of respiratory pathogens and would have therefore generated at some point in their lifetime a humoral antibody response that is measurable. Experiments were conducted in order to determine if high/strong responders could be identified using antibody titers to one or a plurality of respiratory pathogens. In one non-limiting example described below, experiments were conducted in order to determine if antibody titer to respiratory syncytial virus (RSV) in a donor plasma sample could be used to predict the antibody titer to other respiratory pathogens in the donor plasma sample. For example, experiments were performed in order to determine if high antibody titer to a respiratory pathogen (e.g., RSV) could be used as a biomarker to identify a donor as an overall high/strong responder to antigen challenge (e.g., to a plurality of respiratory or other pathogens) via generation of elevated levels of antibodies, versus donors that are not strong responders/do not generate elevated levels of antibodies.

Twenty random plasma donor samples were obtained and the antibody titers to a plurality of respiratory viruses determined. Specifically, the plasma donor samples were studied and characterized for antibody titers for a variety of respiratory pathogens including respiratory syncytial virus (RSV), influenza A (Flu A), influenza B (Flu B), parainfluenza type 1 (PIV1), type 2 (PIV2) and type 3 (PIV3), metapneumovirus (HMPV) and/or coronavirus (strains OC43, and 229E). In order to determine antibody titers, each plasma sample was purified; the purified Ig fraction was analyzed either by neutralization assay (e.g., for RSV) or enzyme-linked immunosorbent assay (ELISA) assay (e.g., influenza A and B, parainfluenza, metapneumovirus, and coronavirus). As described below, titers to each respiratory virus were obtained from each of three separate runs/analysis (labelled as RUN 1, RUN 2, and RUN 3), and the RSV neutralization titer for each sample was compared to the non-RSV respiratory virus titers.

In order to quantitatively measure the titer level of neutralizing anti-RSV antibody present (e.g., in samples of human serum, plasma or products derived from these (also referred to as an analyte)), an RSV microneutralization assay was designed. Briefly, one or more dilutions of analyte (50 µL) were incubated with an infectious stock of RSV (RSV-A2, 50-100 pfus, 50 µL) in 96-well tissue culture plates for 30 minutes at room temperature. The assay diluent was the same as the growth media, Eagle's Minimum Essential Medium with glutamine, 2% FBS and penicillin-streptomycin (hereafter EMEM). Depending on the relative titer of the neutralizing antibody in the analyte sample, the antibody will neutralize some or all of the RSV. An equal volume (100 µL) of approximately $1.5 \times 10^5$ HEp-2 cells (ATCC CCL-23) in EMEM were added to the analyte/virus mixture and the samples incubated at 36-38° C., 4.5-5.5% $CO_2$ for 3 days, at which time only the non-neutralized virus will propagate in the HEp-2 cells. Therefore, the amount of virus that replicates was inversely proportional to the amount of neutralizing antibody present in the analyte. After the incubation the virus was fixed to the tissue culture wells with 80% acetone in PBS. The plates were then developed by an enzyme immune-type assay (EIA). The EIA utilized a mouse-monoclonal antibody to the RSV F-protein, followed by a horse-radish peroxidase enzyme-linked conjugate antibody that detected the mouse-monoclonal to the RSV F-protein. Finally, a chromogenic substrate was added and the EIA analyzed using standard spectrophotometric techniques. The relative absorbance values obtained were directly proportional to the amount of RSV virus in the wells, and thus inversely proportional to the amount of neutralizing antibody in the analyte.

For plasma and serum titers, samples and controls were diluted 2-fold, in duplicate from 1:100 to 1:25,600 across a 96-well tissue culture plate and incubated with virus and HEp-2 cells as described above. In addition, each plate contained wells with no virus (100% inhibition) and virus without antibody (0% inhibition). These absorbance values were used to calculate the 50% inhibition point.

Titers were defined as the minimal dilution of analyte that crossed the 50% inhibition point. All titers were corrected to a standard MQC titer value.

In order to identify and categorize samples as high, medium or low for RSV neutralization titer, assay controls were generated using three separate and distinct samples as well as a reference product control. The assay controls/standards were developed based on analysis of thousands of donors analyzed during experiments conducted during development of the invention. A low quantity control (LQC) was identified and used that contained RSV neutralization titers below the average range of titers observed, a medium QC was identified and used that contained RSV neutralization titers falling in a middle range observed, and a high QC was identified and used that contained RSV neutralization titers at the high end of the assays (accordingly, LQC, MQC and HQC controls were identified and used based upon observations of thousands of samples). For the assay to be considered valid, data obtained from the controls had to meet pre-determined titer and/or absorbance criteria. The relative RSV titer ranges for the low, medium and high assay controls were as follows: 1800-3299; 3300-7799; and 7800 or above, respectively.

For plasma and serum screening, samples and serum controls were heat inactivated and diluted 1:200 in EMEM. The 1:200 dilution was added to duplicate wells and RSV neutralization assay performed as described above. Absorbance ranges were determined for the LQC, MQC and HQC controls. The average of the duplicate absorbance values for each sample was recorded. Again, the absorbance was inversely proportional to the amount of neutralizing antibody in the sample. Therefore, the lower the absorbance the more neutralizing antibody present.

The LQC, MQC and HQC were run in a bracketed fashion for each plate. The titers were required to meet predefined criteria for the assay to be valid. In the instance that a plasma or serum titer was <100, it may be diluted as low as 12.5 fold and 2-fold dilutions tested from 12.5 to 3200. Thus, when a clinical sample was prescreened and the sample titer so low that a dilution of 1:100 would be too large a dilution to allow for any signal detection, dilution was begun at 1:12.5 proceeded by two fold dilutions from that point. This prescreening of clinical samples lead to the result that if the donor titer was so low as to require this type of dilution, they were categorized as low titer. All plates were run with control antibody bracketing the plates.

Enzyme immunoassay (EIA) was performed to detect virus-specific serum IgG for nine respiratory viruses: influenza A and B, RSV, parainfluenza (PIV) virus serotypes 1, 2 and 3, human metapneumovirus (hMPV), and coronavirus 229E (CoV 229E) and coronavirus OC43 per published methods (See, e.g., Falsey et al., J Am Geriatr Soc. 1992; 40:115-119; Falsey et al., J Am Geriatr Soc. 1995; 43:30-36; Falsey et al., J Am Geriatr Soc. 1997; 45:706-711; Falsey et al., J Infect Dis. 2003; 187:785-790). Briefly, antigens were produced from virally infected whole cell lysates for all viruses except RSV. Purified viral surface glycoproteins were used as antigen for RSV EIA according to published methods (See, e.g., Falsey et al., J Am Geriatr Soc. 1992; 40:115-119). Serial two-fold dilutions of each sample were tested in duplicate.

Data analysis was performed via a paired-data approach. Data pairs were created by matching the donor ID within each ELISA assay run.

Specifically, to evaluate the correction between the titers to RSV and the titers to non-RSV respiratory virus at the donor level, antibody data were paired by matching the donor ID within the same ELISA Assay Run (referenced as RUN No. 1, Run No. 2 and Run No. 3). Titers to RSV from a donor were paired with the titers to another non-RSV virus of the same donor. Hence, a total of 20 pairs were created within a Run and a total of 60 pairs were created within a comparison. Linear correlation was assessed between the Titers to RSV and the titers to another non-RSV virus using Pearson correlation coefficient on linear scale and on log 2 scale. All analysis was performed using SAS version 9.3.

Figure 2:
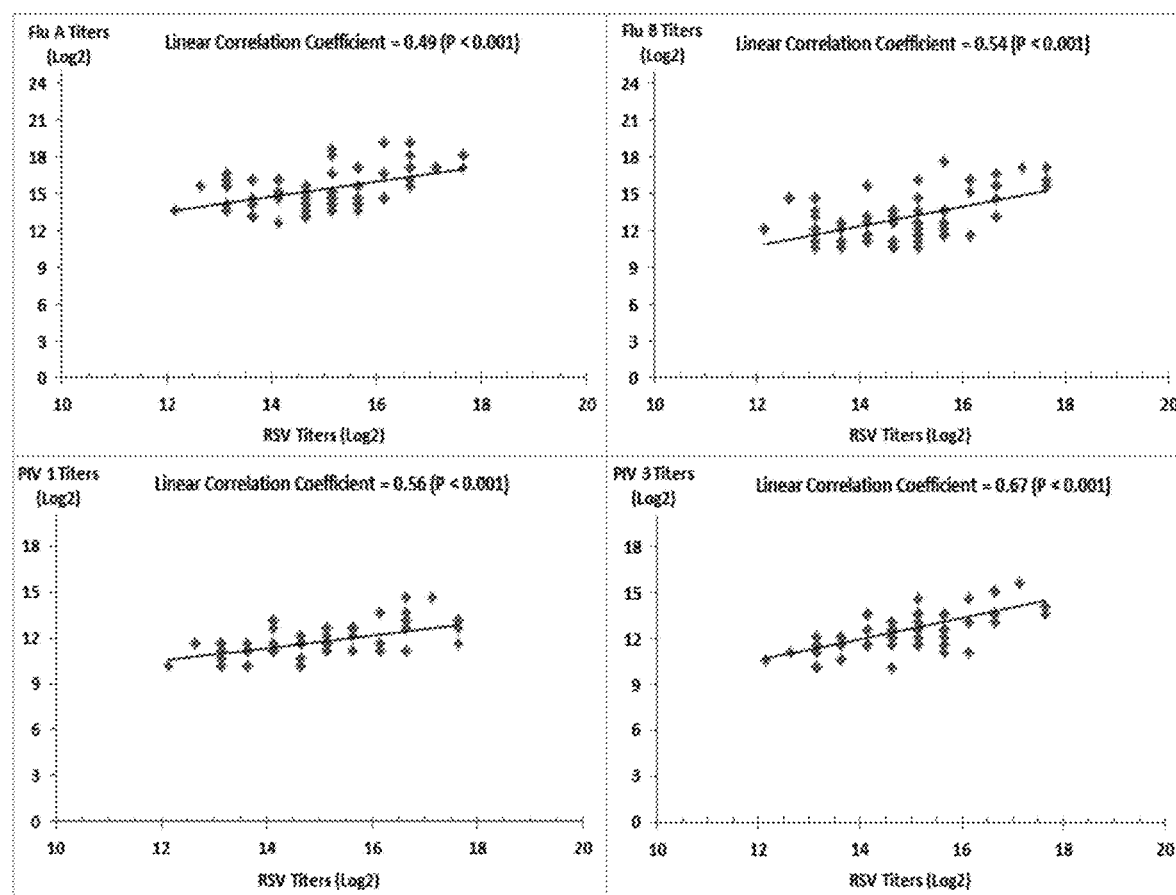
FIG. 2 shows scatter plots of titers to RSV and titers to Flu A, Flu B, PIV 1 and PIV 3 in Log 2 Scale

As shown in Table 1, a positive linear correlation was found between the observed RSV titers and the observed titers to other non-RSV respiratory pathogens. This observation indicated that plasma samples identified as having a high RSV titer value also possessed higher/greater titer to other non-RSV pathogens. All correlation coefficients were statistically significant (p<0.05) with the estimated correlation coefficients ranging from 0.29 (OC43) to 0.67 (PIV 3) on the log 2 scale. A scatter plot showing the RSV neutralization titer compared to the antibody titers for Flu A, Flu B, PIV 1 and PIV 3 in Linear Scale is shown in FIG. 1. A scatter plot showing the RSV neutralization titer compared to the antibody titers for Flu A, Flu B, PIV 1 and PIV 3 in Log 2 Scale is shown in FIG. 2.

TABLE 1

Linear Correlation Coefficient Between Titers to RSV and Titers to Non-RSV Virus

| | Pearson Linear Correlation Coefficients of Titers to RSV and Titers to | | | | | | | |
|---|---|---|---|---|---|---|---|---|
| Scale | Flu A | Flu B | HMPV | PIV1 | PIV2 | PIV3 | OC43 | 229E |
| Log2 | 0.49# | 0.54# | 0.35^ | 0.56# | 0.41^ | 0.67# | 0.29* | 0.41# |
| Linear | 0.49# | 0.59# | 0.28* | 0.50# | 0.24¯ | 0.59# | 0.34^ | 0.40^ |

P-value ≤ 0.001; ^P-value ≤ 0.01; *P-value ≤ 0.05; ¯P-value > 0.05

Additional experiments were performed, during development of embodiments of the invention, in order to determine if the positive linear correlation found between the observed RSV titers and titers to other non-RSV respiratory pathogens could be attributed to an overall increase in all titers.

For this experiment, measles neutralization titer was characterized and determined if it could be used to identify samples as possessing a desired characteristic (e.g., elevated levels antibody titers to other non-measles pathogen). Two separate samples were characterized. Batch 1 displayed a measles neutralization titer of 2.34 and an RSV neutralization titer of 17,275. Batch 2 displayed a significantly lower measles neutralization titer of 0.73, and an RSV neutralization titer of 20,375. Thus, even though the measles titer in one case was roughly only 30% the value of another batch, both batches correlated with/selected for high titer RSV. Accordingly, measles virus was determined not to be useful as a discriminatory marker for selecting plasma samples that are high titer for other, non-measles viruses.

Thus, for each of the 20 random samples analyzed, there was a significant correlation between the neutralizing antibody titer specific for RSV and the antibody titer specific for one or more other respiratory pathogens—a high antibody titer to RSV directly and significantly correlated with high antibody titer(s) specific for other respiratory pathogens.

Example 2

Further experiments were conducted in order to determine if plasma samples identified as high/strong responder (high titer) in Example 1 could be combined with other, non-high titer samples in order to generate a pool of 1000 or more samples, yet that contained a desired, elevated antibody titer to RSV and a desired, elevated antibody titer to one or more other respiratory pathogens.

Plasma donor samples were initially screened (pre-screened as described in Example 1) using optical density for RSV neutralization antibody titer. Briefly, donor plasma diluted 1:400 was mixed with RSV and then overlaid on Hep 2 cells. Neutralizing activity in the plasma was measured via the absence of infection of the hepatocytes. After incubation to allow for viral expression the plate was fixed and then stained with an anti-RSV monoclonal antibody followed by counter antibody conjugated to horse radish peroxidase. The lower the OD observed the higher the neutralizing power of the plasma (fewer viruses left to infect the cells).

The top 20% of the donor samples identified as having the lowest OD's in the prescreen were further characterized. That is, once clinical samples, prescreened by determining a single titration point via neutralization assay, were identified that fell within the top 20% of donor samples with regard to neutralization titer, additional plasma was collected from the donors so identified for further analysis. The additional donor plasma samples were purified, the immunoglobulin fraction purified/prepared, and the fraction analyzed by neutralization assay using a full titration curve in order to obtain RSV neutralization titer. The donor plasma subjected to further testing was serially diluted (e.g., 1:100 1:200 1;400 etc.) in a full titration assay and the titer assigned to the sample (that is, to the plasma donor) as that dilution that gave 50% inhibition of virus growth (50% inhibition is that point which is 50% of the two extremes (saline plus virus is 100 growth and no virus added is 0 growth)).

Immunoglobulin obtained from the additional plasma samples that registered an RSV neutralization titer of 1800 and above resulted in the donor being scored as a high/strong responder. The specific RSV neutralization titer for each plasma sample from each donor was recorded and used in a subsequent blending process. Through experiments conducted during development of embodiments of the invention, it was determined that only about 25-50% of those who fell into the top 20% via the initial/pre-screen were classified using the second RSV neutralization assay as high/strong donors based on the titer of 1800 or above (only 5-10% of the total starting population screened).

Plasma was collected on an ongoing basis from donors classified as high/strong responders and tested periodically (monthly). During this process, if a high/strong responder's RSV neutralizing titer was determined to have dropped below 1700, the donor was no longer classified as a high/strong responder. Donors identified as high/strong responders with a RSV neutralizing titer of 1800 or higher were categorized as high titer (high titer selected donors). Plasma from the remaining 50% of plasma donors identified as being in the top 20% of all donors but that did not have an RSV neutralization titer of 1800 or above were categorized as medium titer. A third group of plasma donors were categorized as non-tested/non-selected source donors.

Plasma from high titer selected donors, non-high titer selected donors and non-selected source donors were combined. The RSV neutralization titer of the mixed/blended plasma samples was calculated arithmetically as follows: Multiply titer of the plasma by its volume to get total titer and then divide by the total volume of all the plasma samples. For example, if one liter of plasma titer of 100 was added to one liter of plasma titer 200 the total titer is 100×1+200 xl which is equal 300 divided by 2 liter for a final titer of 150. It was tested whether it would be possible to generate a mixed plasma from 1000 different donors with a total volume of 2500 liters and an RSV neutralization titer of 1800 or greater (and/or a RSV titer of 1800 or greater and an elevated titer to one or more other respiratory viruses). Because the target RSV neutralization titer was 1800, if the mix arithmetically generated a higher value, then normal source plasma was mixed in. The titer for non-tested/non-selected source donor plasma was set at zero. Therefore, when normal source plasma was added there was no increase in titer value only an increase in the volume (denominator) which, as described above, resulted in a lower final RSV neutralization titer. Blending proceeded either adding high titer material or normal source plasma until the a target titer was reached. Attempts were made in order to generate a pooled plasma composition containing about 2500 liters (L) from at least 1000 human plasma donors with a final RSV titer of 1800, but utilizing significantly less than all high titer selected donors in the pool (e.g., due to the limited availability of high titer donors). Surprisingly, through experiments conducted during development of embodiments of the invention, it was determined that plasma samples could be categorized and blended in order to generate 2500 liters of pooled plasma from at least 1000 donors with a final RSV neutralization titer of 1800, wherein less than half of the donors used for pooling were high titer selected donors (e.g., identified by the two step screening processes described above (See Table 2, below) and where the pooled plasma composition contained significant levels of antibody titers specific for measles, diphtheria and/or polio.

TABLE 2

Characteristics of several pooled plasma compositions of the invention.

| Lot # | 1 | 2 | 3 | 4 |
|---|---|---|---|---|
| Total Volume (L) | 2196 | 2192 | 2195 | 2199 |
| No. plasma donors | 1022 | 1021 | 1035 | 1033 |
| % High-titer selected donors | 36 | 39 | 45 | 44 |
| % Non-high titer selected donors | 64 | 61 | 55 | 56 |
| RSV titer of pooled plasma composition | 1805 | 1805 | 1806 | 1804 |

Accordingly, the invention provides a blending/pooling process that provides a pooled plasma composition or immunoglobulin prepared from same that contains a standardized and reproducible level of respiratory pathogen (e.g., RSV) specific antibodies thereby providing a heretofore unavailable, consistent and reproducible immunoglobulin product (e.g., for use as IVIG). Experiments confirmed that a pooled plasma composition or immunoglobulin prepared from same of the invention (e.g., 2500 liters of pooled plasma from 1000 donors with a final RSV neutralization titer of 1800) could be consistently generated from different groups of 1000 donors. Further experiments confirmed that a pooled plasma composition of the invention (e.g., 2500 liters of pooled plasma from 1000 donors with a final RSV neutralization titer of 1800) contained antibody levels to tetanus, measles and polio that prevent, or protect from, infection with same, and also contained elevated antibody titer(s) specific for the respiratory pathogens described in Example 1.

Upon completion of mixing of the samples, the arithmetic calculation was repeated (with the separate volumes for each donor with their corresponding titers) in order to verify that the original blending equation was correct. Thus, although each lot prepared according to this method possesses a different ratio of high titer selected donors and non-high titer selected donors, the screening and blending methods identified and described herein provide a blended plasma product that possesses a standardized, elevated anti-RSV-neutralization titer as well as elevated levels of respiratory pathogen-specific antibody titers. Once generated, the various mixture of 1000 donor plasma samples were utilized to manufacture IVIG.

All IVIG manufacturing activities were conducted following Good Manufacturing Practices (GMP) so as to minimize contamination and ensure the purity, identity, and potency of the drug substance. The manufacturing process followed the modified Cohn-Oncley cold alcohol fractionation process which isolates the immunoglobulin fraction as a solution (See, e.g., Cohn e al., J Am Chem Soc, 62, 459-475 (1946); and Teschner et al., Vox Sang. 2007 January; 92(1):42-55, each of which is herein incorporated by reference in its entirety). The Cohn-Oncley method is a multi-step process of isolating immunoglobulins from plasma using different alcohol concentrations under specific conditions of temperature, pH, protein concentration and ionic strength at each step. Following fractionation, the intermediate drug substance is subject to virus inactivation/removal steps, further purification, and formulation into the bulk drug substance.

The modified Cohn-Oncley cold alcohol fractionation began with pooling of a sufficient number of plasma units to obtain 1800-2000 L of plasma (2500 units, representing at least 1000 separate donors). It was verified that the plasma units met all regulatory requirements and Plasma Protein Therapeutics Association standards for human source plasma.

Cryoprecipitate was removed by centrifugation at <5° C. before the fractionation began. The cryopoor plasma was brought to pH 7.3±0.1 and 8±3% SDA-3A Ethanol by weight and held at −2±1° C. while Fraction I precipitated. Fraction I was removed by centrifugation and the supernatant further processed.

Fraction I supernatant was brought to pH 7.9±0.1 and 25±3% SDA-3A Ethanol by weight and held at −5±1° C. while Fraction II+III precipitated. Fraction II+III were removed by centrifugation, resuspended in sodium phosphate buffer at pH 7.2±0.1. SDA-3A Ethanol was added to 20±3% and Fraction II+IIIw was formed while the mixture was held at −5±1° C.

Fraction II+IIIw was resuspended and Fraction III was removed at pH 5.2±0.05, 17±3% SDA-3A Ethanol and temperature of −5±1° C. Fraction III was separated by centrifugation and the supernatant further processed.

Acid washed Celite was added to the Fraction III supernatant and then removed by depth filtration. The filtered supernatant was brought to a concentration of <70 g protein/L, pH4.2±0.25 and conductivity ≤5 mS prior to viral inactivation with 0.3±0.1% TnBP and 1.0±0.2% Triton-X 100 at 28±2° C. The TnBP and Triton-X-100 were removed by C-18 chromotography. The C-18 eluate was further purified using a Q-Sepharose column.

Additional virus removal was achieved using 35 nm nanofiltration of the Q-Sepharose eluate. After nanofiltration the product was formulated using ultrafiltration/diafiltration.

Three separate, high titer RSV neutralizing antibody batches of IVIG (RSV-IVIG) were manufactured (from plasma samples pooled from 1000 or more subject and that contained a standardized, elevated antibody titer to RSV utilizing the prescreening and screening compositions and methods of the invention). The three RSV-IVIG were compared to 7 different lots of commercially available, conventional IVIG (4 different manufactures/brands). ELISA assays were performed in order to quantitate antibody titer to RSV, PIV1, PIV2, OC43, 229E, FluA, and Flu B. The ELISA assays were run on three separate dates.

ELISA testing of IVIG was performed blinded to the type of sample. All samples were diluted with sample dilution buffer (PBS with 0.3% Tween 20 and 0.1 M EDTA) to a standard concentration of 50 mg of IgG per ml. Each viral antigen was diluted at previously determined concentration in bicarbonate buffer and coated separately on enzyme immunoassay microtiter plates and stored overnight in humidified chambers at 4° C. The following day, plates were washed and eight serial 2-fold dilutions in duplicate of unknown product were incubated on the antigen plates at room temperature in humidified chambers for 3 hours. The initial dilution of IVIG solution placed on antigen plates was 1:1600. Plates were then washed and bound IgG was detected with alkaline phosphatase conjugated goat anti-human IgG followed by substrate. A standard serum was included on each plate and the IgG titer for a specific virus was defined as the highest dilution with an optical density (OD) of 0.20.

Statistical Analysis. Titer data was tabulated with descriptive statistics of N (sample size, mean, geometric mean, standard deviation, minimum, median, and maximum). Difference between the RSV-IVIG and commercial IVIG (that is, Group 1 vs Group 2) were presented as the ratio of geometric means (RGM) and 95% Confidence intervals for the RGM was also provided. P-value for testing of the null hypothesis that the RGM equaled to 1 was produced based on 2-sample t-test at significance level of 0.05.

Figure 3:
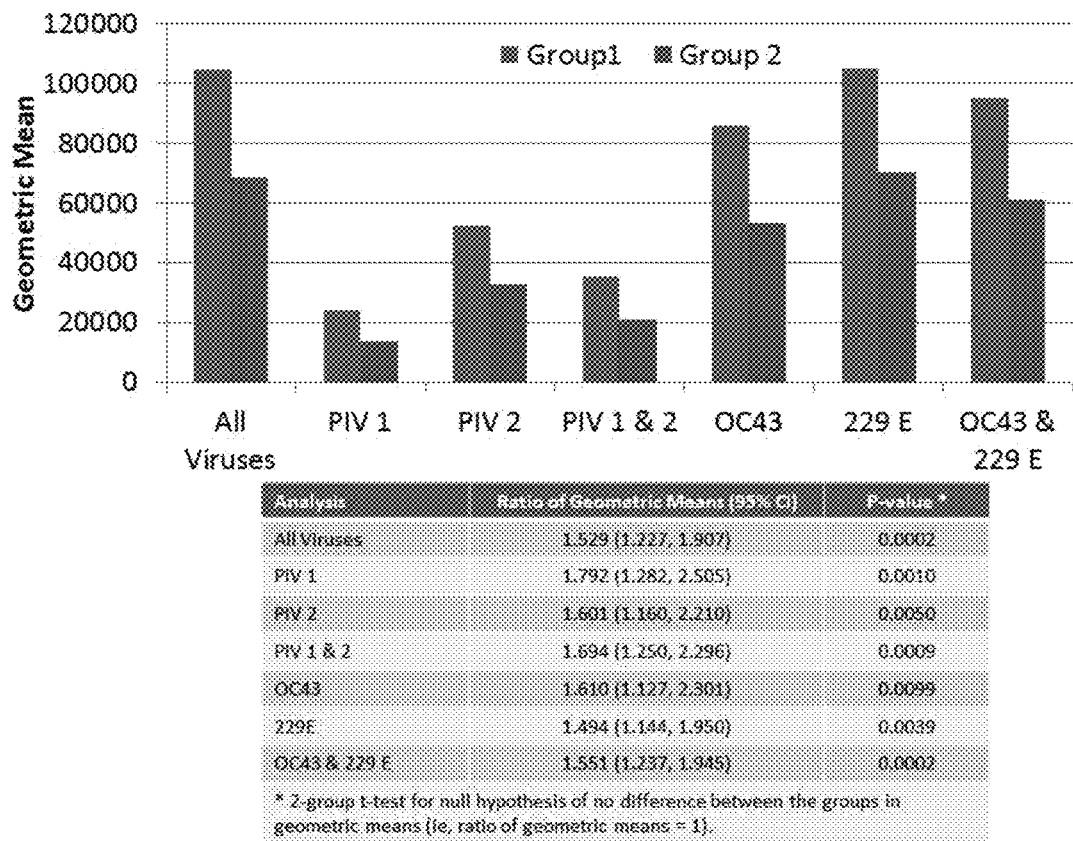
FIG. 3 depicts graphs indicating the level of neutralizing antibody titers for respiratory pathogens present in IVIG compositions generated using compositions and methods of the invention.

FIG. 3 demonstrates that the geometric mean antibody titer of the RSV-IVIG was significantly greater for other respiratory viruses as compared to the geometric mean antibody titer of the commercial lots of IVIG. In particular, there was a 1.5 to 1.8 fold greater antibody titer to the other respiratory viruses in the RSV-IVIG (group 1) as compared to the commercial IVIG (group 2).

The properties of the IVIG from 1000 or more samples containing elevated levels of neutralizing antibody titers to one or more respiratory pathogens generated using the compositions and methods of the invention is a significant advancement and improvement over other IVIG available in the art. In particular, the IVIG compositions of the invention do not display or possess a neutralizing antibody titer for only a single pathogen (e.g., dominance for only one type of respiratory pathogens), but rather, through the methods of identifying donors and the blending processes developed and described herein, IVIG is provided that contains significantly elevated neutralizing titers to a plurality of respiratory pathogens and other pathogens (e.g., polio, diphtheria, etc.), compared to the titers in 1000 randomly mixed plasma samples. The discovery of the use of neutralizing antibody titer to RSV (or other respiratory pathogen) as a biomarker to identify plasma donors that are high-titer selected donors (high/strong responders in general to respiratory pathogens (e.g., influenza A virus, influenza B virus, parainfluenza virus type 1, parainfluenza virus type 2, metapneumovirus, coronavirus, *S. pneumonia, H. influenza, L. pneumophila*, and group A *Streptococcus*)) makes possible the ability to identify donors and plasma that can be blended with non-high titer selected donors and non-selected donor plasma to provide a beneficial pooled plasma product. Thus, while an understanding of a mechanism is not needed to practice the present invention, and while the present invention is not limited to any particular mechanism of action, in some embodiments, the invention provides a heretofore unavailable pooled plasma composition (e.g., prepared according to the above described methods)) that contains a significant amount (e.g., greater than 50%) of non-high titer selected donor plasma (non-high titer RSV plasma) that provide therapeutic benefit not achievable with standard hyperimmune immune globulin (e.g., prepared from a limited number (e.g., 100-300) of plasma donors). In a further embodiment, due to the elevated levels of neutralizing antibody titers to one or a plurality of RSV, influenza A virus, influenza B virus, parainfluenza virus type 1, parainfluenza virus type 2, metapneumovirus, coronavirus, *S. pneumonia, H. influenza, L. pneumophila*, and group A *Streptococcus*, such pooled plasma compositions provide a significantly improved therapeutic benefit to a subject administered the composition. For example, a pooled composition of the invention, compared to pooled plasma samples obtained from 1000 or more random human subjects, provides viral neutralization properties against one or a plurality of respiratory pathogens or other pathogens that is not provided for by randomly pooled samples (e.g., provides a subject prophylactic and/or therapeutic levels of antibodies to polio, diphtheria and/or measles). In this way, a subject administered a composition of the invention is able to fight off, or be treated for, infections that are not treatable with a composition of pooled plasma samples obtained from 1000 or more random human subjects or that are not treatable with a conventional hyperimmune immune globulin. For example, a pooled plasma composition according to the invention (e.g., from 1000 or more samples wherein the pooled plasma composition comprises a neutralizing RSV antibody titer of 1800 or above and elevated levels of antibodies to one or more respiratory pathogens) when administered to a subject provides the subject the ability to fight off, or be treated for, infections that are not treatable with a composition of pooled plasma samples obtained from 1000 or more random human subjects and/or that are not treatable with a conventional hyperimmune immune globulin prepared from limited numbers of donors (e.g., such hyperimmune immune globulin requires a subject to be vaccinated against diphtheria, polio and/or measles in addition to receiving the hyperimmune immune globulin).

For example, IVIG prepared according to the methods described above was compared with a conventional RSV-specific immune globulin available in the art, RESPIGAM (MEDIMMUNE, Inc., hyperimmune immune globulin prepared from several hundred (100-300) healthy human plasma donors that have a higher than normal concentration of antibodies specific for RSV). While IVIG of the invention displayed a similar level of RSV neutralizing activity to that of RESPIGAM, neutralizing antibody titers to other respiratory viruses were significantly higher in the IVIG of the invention (Table 3, IVIG-1000 donors) compared to the levels found in RESPIGAM (See Table 3).

TABLE 3

Neutralization titers for respiratory pathogens.

| | RSV | PIV1(paraflu) | PIV2 | OC43(coronavirus) | 229E(coronavirus) |
|---|---|---|---|---|---|
| IVIG-1000 donors | 204,253 | 36,107 | 72,214 | 102,126 | 144,289 |
| RESPIGAM | 204,253 | 12,765 | 25,531 | 36,107 | 25,531 |

IVIG prepared according to the methods described above (RSV-IVIG) was administered in a randomized, double blind dose range study in immunocompromised patients infected with RSV (a phase II multicenter study carried out at centers in the U.S., Canada, Australia and New Zealand). Immunocompromised patients were either bone marrow transplant or solid organ transplant patients that were concurrently on immunosuppressive treatment between the ages of 2-65 (mean age of 38 years). Upper respiratory RSV infection was confirmed in each patient using RT-PCR at time of enrollment. Patients fell into one of three arms. The first arm received 1500 mg/kg RSV-IVIG on day one followed by 750 mg/kg RSV-IVIG on day two. The second arm received 750 mg/kg RSV-IVIG on day one followed by 750 mg/kg RSV-IVIG on day two. The third arm received saline placebo on both days. On day 18, patients in arm 1 displayed a mean fold increase from baseline of anti-RSV neutralization titers of 9.24 (p value relative to placebo=0.0043; with 85.7% of patients displaying a greater than 4 fold increase). On day 18, patients in arm 2 displayed a mean fold increase from baseline of anti-RSV neutralization titers of 4.85 (p value relative to placebo=0.0268; with 42.9.% of patients displaying a greater than 4 fold increase). Antibody titers to *Streptococcus pneumonia* before and after administration of IVIG to the patients was also assessed. In general, there was no significant increase or decrease in the *Streptococcus pneumonia* specific antibody titers in the patients post administration of IVIG.

Example 3

IVIG Therapeutic Potential

Immunotherapeutic compositions of the invention were tested in a cotton rat model of human immunodeficiency. Therapeutic as well as prophylactic potential was assessed. For analysis of therapeutic potential, RSV-IVIG prepared as described in Examples 1 and 2 above was administered therapeutically to immunosuppressed (cyclophosphamide treated) and normal cotton rats challenged with RSV/A/Long.

Animals: Fifty-three (53) inbred male and female *Sigmodon hispidus* cotton rats between 6 to 8 weeks of age (Source: Sigmovir Biosystems, Inc., Rockville Md.) were maintained and handled under veterinary supervision in accordance with the National Institutes of Health guidelines and Sigmovir Institutional Animal Care Utilization Committee's approved animal study protocol (IACUC Protocol #2). Cotton rats were housed in clear polycarbonate cages individually and provided with standard rodent chow (Harlan #7004) and tap water ad lib.

Challenge Virus: The prototype Long strain of RSV (ATCC, Manassas, Va.) was propagated in HEp-2 cells after serial plaque-purification to reduce defective-interfering particles. A pool of virus designated as hRSV/A/Long Lot #041513 containing approximately $5.0 \times 10^7$ pfu/mL in sucrose stabilizing media was used for in vivo experiments. This stock of virus was stored under $-80°$ C. conditions and has been characterized in vivo using the cotton rat model and validated for upper and lower respiratory tract replication.

Test Article(s): Immunoglobulin (at 100 mg/mL) for intravenous administration (IVIG) was obtained as described in Examples 1 and 2 above and stored at $4°$ C. until the start of the in vivo use. Briefly, plasma samples pooled from 1000 or more subjects with a total volume of 2500 liters was generated that contained a standardized, elevated antibody titer to RSV (neutralization titer of 1800) utilizing the prescreening and screening compositions and methods of the invention, from which immunoglobulin was prepared as described in Example 2.

Methods.

Identification of animals was performed using ear tags. Bleeding was performed using retro-orbital sinus bleed. Collection in EDTA tubes for whole blood analysis (day −3), collection of serum (prebleed, day 4 p.i., day 10 p.i.). Route of infection was intranasal (i.n.) inoculation. Route of IVIG treatment was intra-peritoneal injection (i.p.). Euthanasia was performed using $CO_2$ asphyxiation. Lung tissue, liver tissue, and kidney tissue were harvested post euthanasia for RSV plaque assays, quantitative PCR (qPCR) and histopathology.

Table 4 provides the Experimental Study Design for these experiments.

| Group | # of Animals | Treatment | Route | Treatment Type | Volume of i.p. treatment* | Sac |
|---|---|---|---|---|---|---|
| Immunosuppressed: | | | | | | |
| A | 10 | Saline | i.p. dl, 4, 7 | Therap. | 1.5 ml/1.5 ml/1.5 ml | d4, d10 |
| B | 10 | IGIV 1,500 mg/kg (High/High/High Dose) | i.p. dl, 4, 7 | Therap. | 1.5 ml/1.5 ml/1.5 ml | d4, d10 |
| C | 10 | IGIV 1,500; 750 mg/kg (High/Low/Low Dose) | i.p. dl, 4, 7 | Therap. | 1.5 ml/0.75 ml/0.75 ml | d4, d10 |
| Normal: | | | | | | |
| D | 10 | Saline | i.p dl | Therap. | 1.5 ml | d4, d10 |
| E | 5 | IGIV 1,500 mg/kg | i.p dl | Therap. | 1.5 ml | d4 |
| F | 5 | IGIV 750 mg/kg | i.p dl | Therap. | 0.75 ml | d4 |
| G** | 3 | TBD | | | | |

*Volume of saline or 10% IgG stock solution administered i.p. per 100 g weight
**Group G: extra 3 animals to undergo cyclophosphamide treatment. These animals are to be used for potential mortalities during the first three weeks of the study. Group assignment is to be determined (TBD) on the day of RSV infection (d0).

Figure 4:
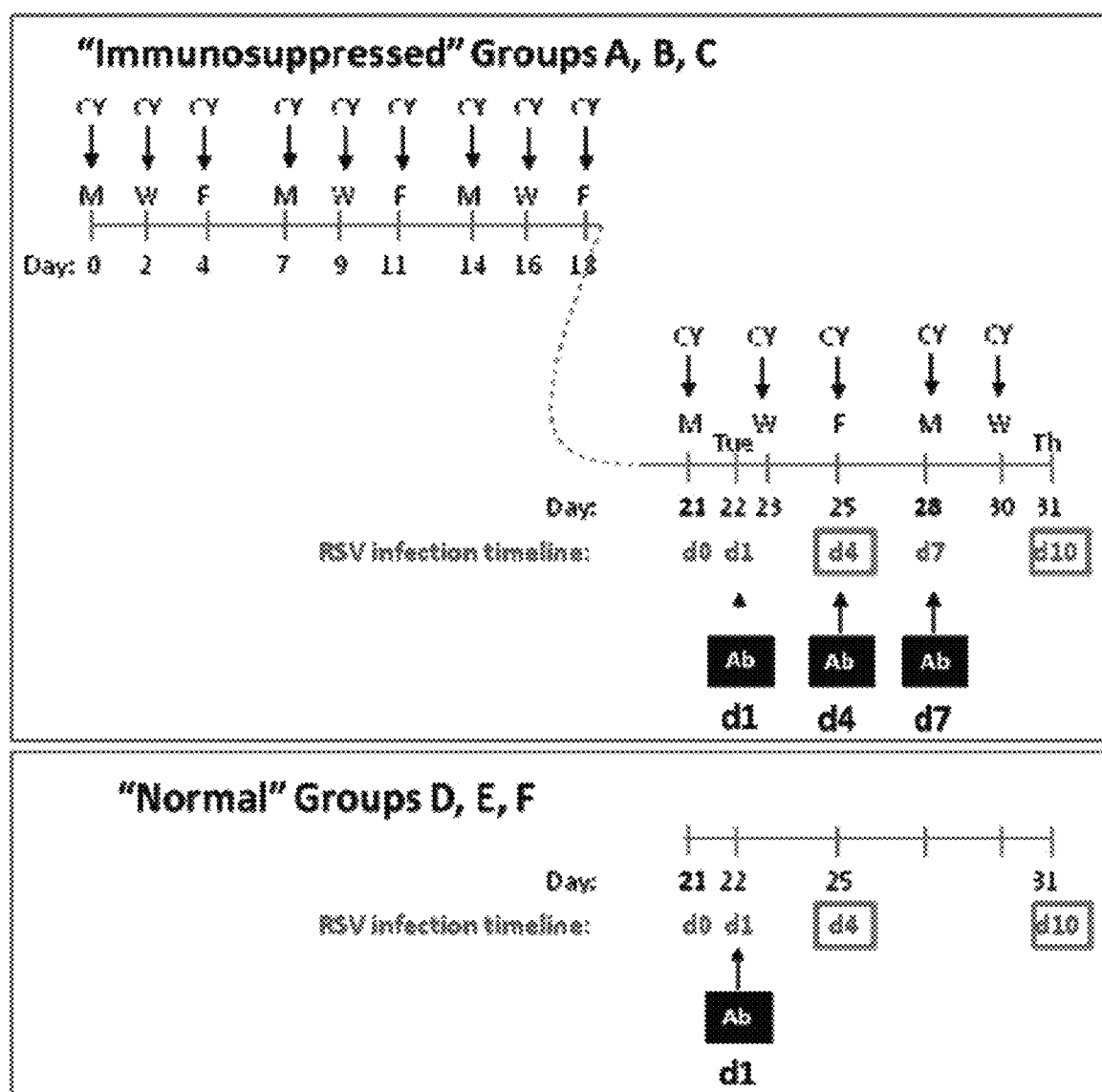
FIG. 4 shows a schematic of a cotton rat model utilized to study the therapeutic potential of an immunoglobulin prepared as described in Example 2.

A schematic of the cotton rat model utilized to study the therapeutic potential of RSV-IVIG prepared as described in Example 2 is shown in FIG. 4.

Whole Blood Assay. Automated whole blood analysis was carried out on blood samples collected in EDTA-containing tubes. Total number of white blood cells and lymphocytes was analyzed.

RSV plaque assay. Lung homogenates were clarified by centrifugation and diluted 1:10 and 1:100 in EMEM. Confluent HEp-2 monolayers in 24-well plates were infected in duplicates with 50 µl of sample per well starting with undiluted (neat) samples followed by diluted homogenates. After one hour incubation at 37° C. in a 5% $CO_2$ incubator, wells were overlayed with 0.75% methylcellulose medium and plates restored into the 37° C. incubator. After 4 days of incubation the overlay was removed and the cells were fixed with 0.1% crystal violet stain for one hour, then rinsed and air-dried. Plaques were counted and viral titers were expressed as plaque forming units per gram of tissue. Viral titer for a group was calculated as the geometric mean+ standard error for all animals in that group at a given time. Student-t test was applied to determine significance of change in viral replication between vehicle-treated and test groups, with $p<0.05$ indicating a statistically-significant difference.

Real-time PCR. Total RNA was extracted from homogenized lung, kidney or liver tissue using the RNeasy purification kit (QIAGEN). One µg of total RNA was used to prepare cDNA using QuantiTect Reverse Transcription Kit (Qiagen). For the real-time PCR reactions the QuantiFast SYBR Green PCR Kit (Qiagen) was used in a final volume of 25 µl, with final primer concentrations of 0.5 µM. Reactions were set up in 96-well trays. Amplifications were performed on a Bio-Rad iCycler for 1 cycle of 95° C. for 3 min, followed by 40 cycles of 95° C. for 10 sec, 60° C. for 10 sec, and 72° C. for 15 sec. The baseline cycles and cycle threshold (Ct) were calculated by the iQ5 software in the PCR Base Line Subtracted Curve Fit mode. Relative quantification of DNA was applied to all samples. The standard curves were developed using serially-diluted cDNA sample most enriched in the transcript of interest (e.g., lungs from day 4 post-primary RSV infection). The Ct values were plotted against $\log_{10}$ cDNA dilution factor. These curves were used to convert the Ct values obtained for different samples to relative expression units. These relative expression units were then normalized to the level of β-actin mRNA ("housekeeping gene") expressed in the corresponding sample. For animal studies, mRNA levels were expressed as the geometric mean±SEM for all animals in a group at a given time.

Results.

Figure 6:
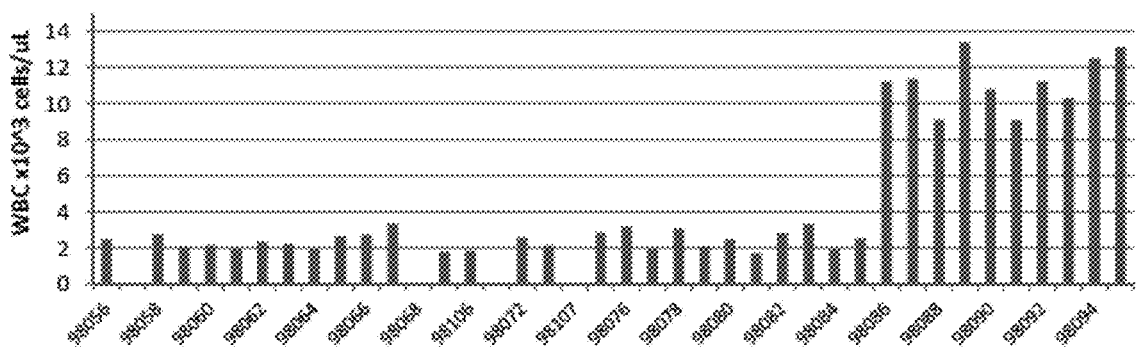
FIG. 6 shows Total White Blood Cell counts and total Lymphocyte counts were reduced in all cyclophosphamide treated animals (groups A, B, C, and G) compared to normal, unmanipulated cotton rats (groups D, E, and F).
Figure 6:
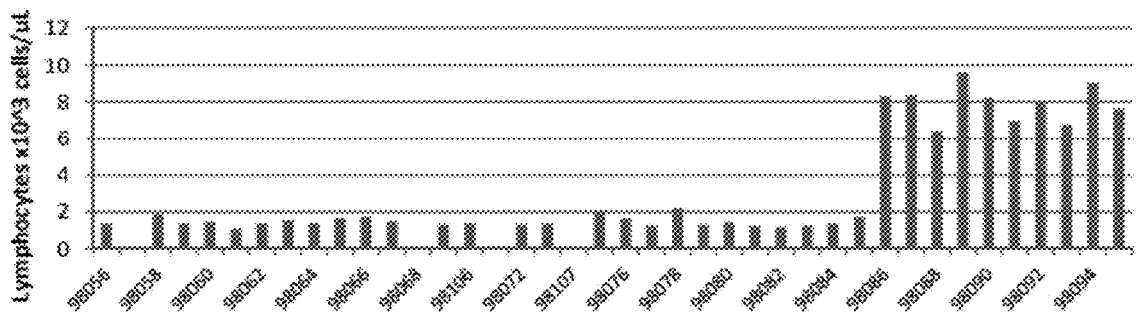

Whole Blood Assay. Total White Blood Cell counts and total Lymphocyte counts were reduced in all cyclophosphamide treated animals (groups A, B, C, and G) compared to normal, unmanipulated cotton rats (groups D, E, and F). This difference was seen in samples collected 18 days after the beginning of cyclophosphamide treatment (Day −3 with respect to RSV challenge (See FIG. 6).

Figure 7:
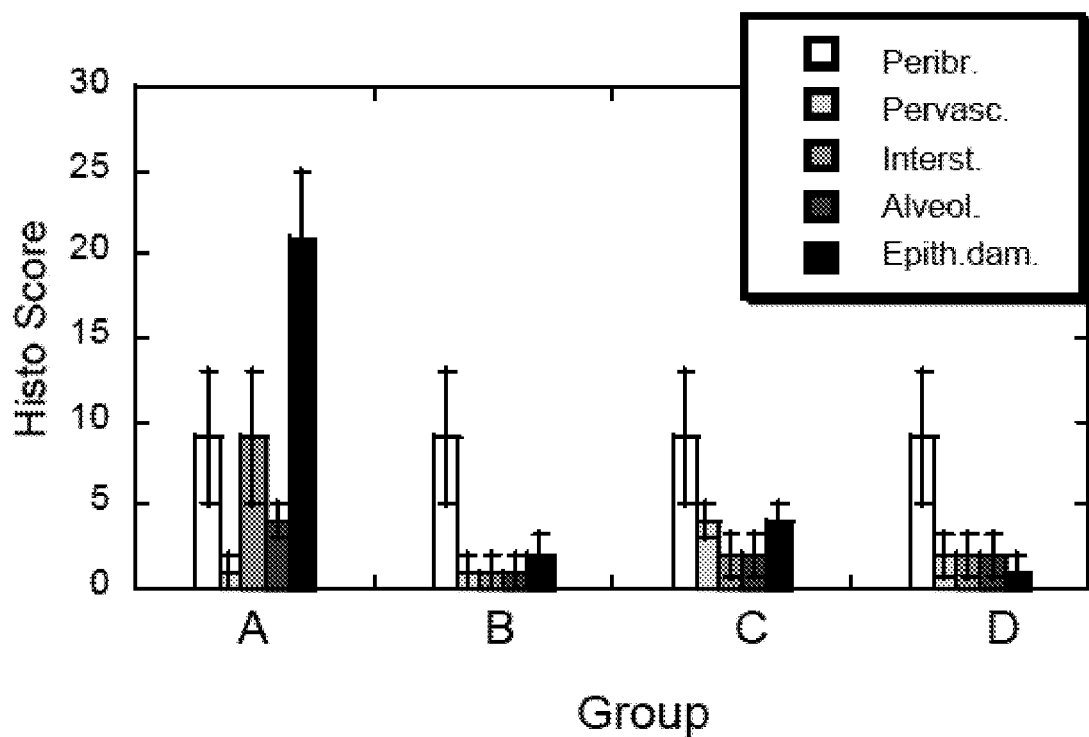
FIG. 7 shows lungs of RSV infected immunosuppressed animals displayed increased epithelial damage compared to the lungs of RSV-infected normal cotton rats (group A compared to group D) and that treatment of animals with IVIG of the invention (groups B and C) resulted in reduction of epithelial damage.

Pulmonary Histopathology. Pulmonary histopathology was evaluated in RSV-infected immunosuppressed animals from groups A, B, and C and in normal saline-treated and RSV-infected animals (group D) on day 10 p.i. Lungs of RSV infected immunosuppressed animals displayed increased epithelial damage compared to the lungs of RSV-infected normal cotton rats (group A compared to group D) (FIG. 7). Treatment of animals with IGIV (groups B and C) resulted in reduction of epithelial damage. No significant differences were noted for the two different regimes of IVIG treatment used in groups B and C.

Figure 8:
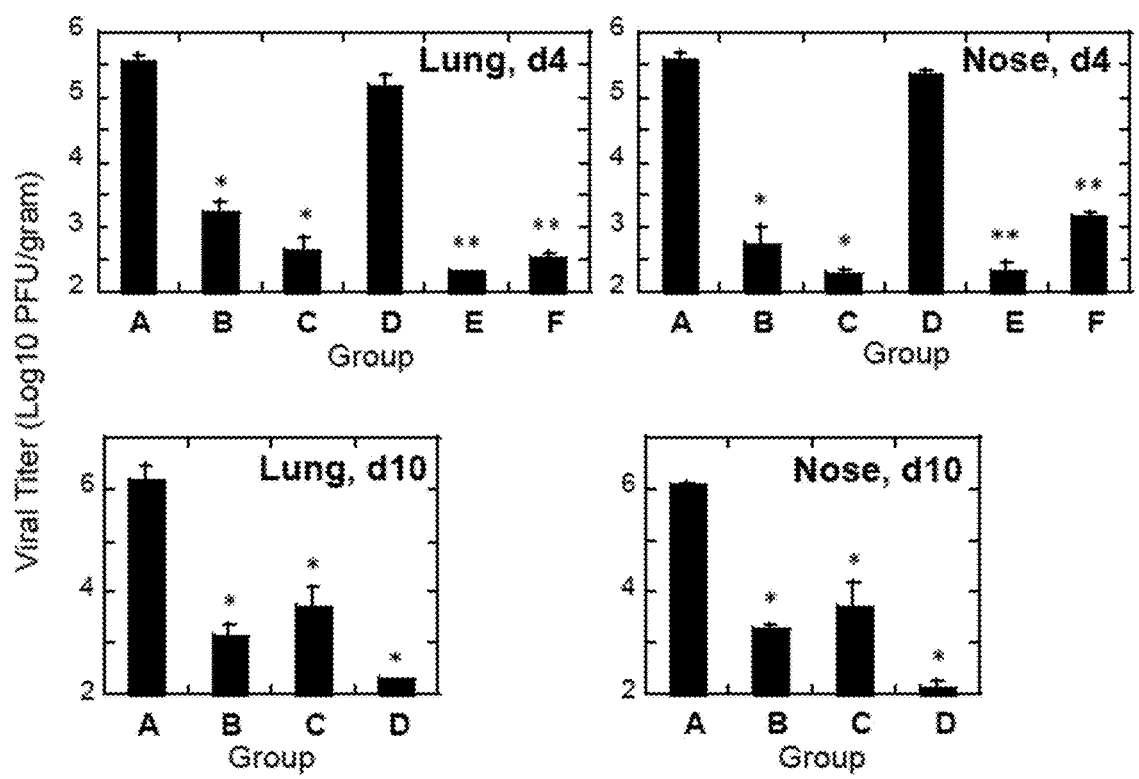
FIG. 8 shows viral titers from total lung and nose homogenates measured on days 4 and 10 post-intranasal challenge with approximately 5.0 $Log_{10}$ of RSV/A/Long in the immunosuppressed cotton rat with and without treatment using IVIG of the invention.

Lung RSV Titers. Viral titers from total lung and nose homogenates were measured on days 4 and 10 post-intranasal challenge with approximately 5.0 $\log_{10}$ of RSV/A/Long. On day 4 post-infection viral load in RSV infected normal and immunosuppressed cotton rats treated with saline (groups D and A, respectively) was comparable between the groups for both lungs and noses. Therapeutic treatment with IVIG of either normal (groups E and F) or immunosuppressed animals (groups B and C) resulted in a statistically significant ($p<0.05$) reduction of lung and nose viral titer. On day 10 post-infection, no RSV was detected in the lungs of saline-treated normal infected animals (group D), and virus was barely detectable in the nose of two out of the five group D animals. In contrast, over 6 $\log_{10}$ PFU/gram was recovered from the lungs and nose of saline-treated immunosuppressed animals infected with RSV (group A). IVIG treatment caused in a statistically-significant reduction of viral load in both the lungs and the nose of infected animals (groups B and C). A moderate dose-dependency was seen, with 0.5 $Log_{10}$ PFU/gram greater reduction seen in the lung samples collected from the group of animals treated with the higher dose of IVIG (group B compared to group C) (See FIG. 8).

Figure 9:
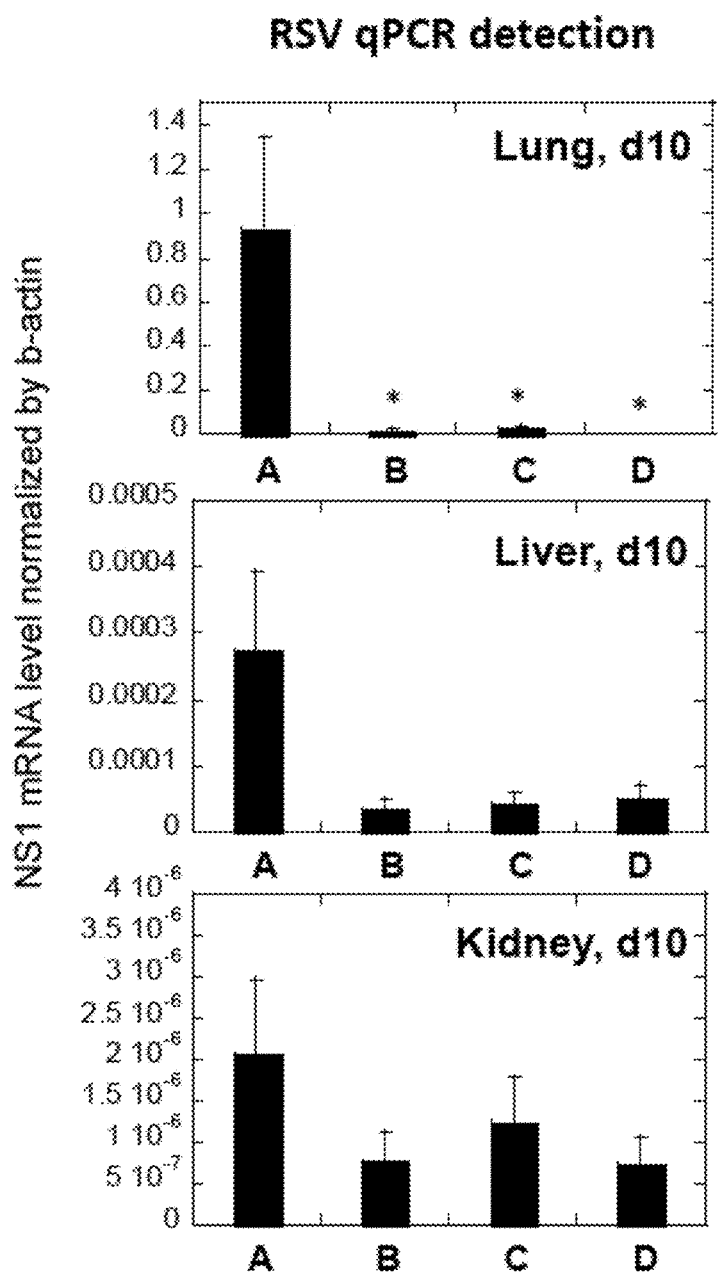
FIG. 9 shows RSV gene expression (NS1 mRNA) quantified by qPCR assay in the lung, liver, and kidney samples collected from group A, B, C, and D animals on day 10 p.i. The level of RSV transcript was lowest in group D and highest in group A samples. Treatment of immunosuppressed animals with IVIG of the invention resulted in statistically-significant reduction in the lung RSV NS1 mRNA level (groups B and C compared to group A).

RSV detection by qPCR. RSV gene expression (NS1 mRNA) was quantified by qPCR assay in the lung, liver, and kidney samples collected from group A, B, C, and D animals on day 10 p.i. The level of RSV transcript was lowest in group D and highest in group A samples. Treatment of immunosuppressed animals with IVIG resulted in statistically-significant reduction in the lung RSV NS1 mRNA level (groups B and C compared to group A) (FIG. 9). NS1 transcript was also reduced by IVIG treatment in the liver and kidney of immunosuppressed RSV-infected animals.

Immunosuppression in cyclophosphamide-treated groups A, B, C, and G was verified by significant decrease in whole blood cell and lymphocyte counts compared to normal cotton rats (groups D, E, and F). Immunosuppressed animals treated with IVIG of the invention, groups B and C, showed significant reduction in lung and nose viral load at day 4 p.i. and day 10 p.i. compared to RSV-infected immunosuppressed animals treated with saline (group A). This reduction was accompanied by reduction in lung histopathology and a decrease in the detection of viral RNA in lung, liver, and kidney samples of group B and C animals on day 10 p.i. Treatment of cotton rats with IVIG of the invention resulted in significant reduction of RSV load in the lungs and nose of IVIG-treated animals (groups E and F) compared to saline-treated (group D) animals on day 4 p.i.

Challenge Virus: The prototype Long strain of RSV (ATCC, Manassas, Va.) was propagated in HEp-2 cells after serial plaque-purification to reduce defective-interfering particles. A pool of virus designated as hRSV/A/Long Lot #041513 containing approximately $5.0 \times 10_7$ pfu/mL in sucrose stabilizing media was used for in vivo experiments. This stock of virus is stored under $-80°$ C. conditions and has been characterized in vivo using the cotton rat model and validated for upper and lower respiratory tract replication.

Methods.

Identification of animals was performed using ear tags. Bleeding was performed using retro-orbital sinus bleed. Collection in EDTA tubes for whole blood analysis (day −3), collection of serum (prebleed, day 4 p.i., day 10 p.i.). Route of infection was intranasal (i.n.) inoculation. Route of IVIG treatment was intra-peritoneal injection (i.p.). Euthanasia was performed using $CO_2$ asphyxiation. Lung tissue, liver tissue, and kidney tissue were harvested post euthanasia for RSV plaque assays, quantitative PCR (qPCR) and histopathology.

Table 5 provides experimental study design for these experiments.

TABLE 5

| Group | # of Animals | Treatment | Route | Dose | Volume of 10% IgG stock solution administered i.p. per 100 g weight: | Sac |
|---|---|---|---|---|---|---|
| CY-treated: | | | | | | |
| A | 10 | Normal Saline | i.p. | 1.5 ml | 1.5 ml | d4, d10 |
| B | 10 | Anti-RSV IgG 1 | i.p. | 1500 mg/kg | 1.5 ml | d4, d10 |
| C | 10 | Anti-RSV IgG 1 | i.p. | 750 mg/kg | 0.75 ml | d4, d10 |

Example 4

IVIG Prophylactic Potential

Immunotherapeutic compositions of the invention were tested in a cotton rat model of human immunodeficiency. Therapeutic as well as prophylactic potential was assessed. For analysis of prophylactic potential, immunoglobulin prepared as described in Example 2 above was used prophylactically in immunosuppressed (cyclophosphamide treated) cotton rats challenged with RSV/A/Long.

Animals: Thirty (30) inbred male and female *Sigmodon hispidus* cotton rats between 6 to 8 weeks of age (Source: Sigmovir Biosystems, Inc., Rockville Md.) were maintained and handled under veterinary supervision in accordance with the National Institutes of Health guidelines and Sigmovir Institutional Animal Care Utilization Committee's approved animal study protocol (IACUC Protocol #2). Cotton rats were housed in clear polycarbonate cages individually and provided with standard rodent chow (Harlan #7004) and tap water ad lib.

Figure 5:
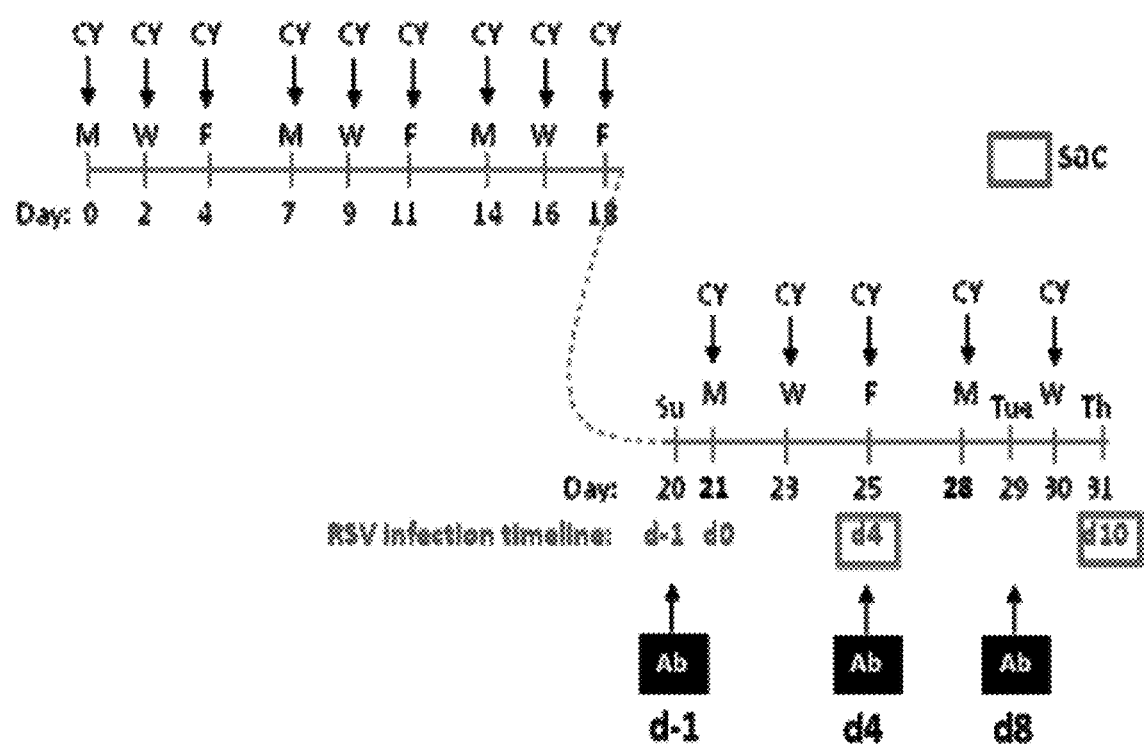
FIG. 5 shows a schematic of a cotton rat model utilized to study the prophylactic potential of an immunoglobulin prepared as described in Example 2.

FIG. 5 shows a schematic of a cotton rat model utilized to study the prophylactic potential of an immunoglobulin prepared as described in Example 2.

Whole Blood Assay. Automated whole blood analysis was carried out on blood samples collected in EDTA-containing tubes. Total number of white blood cells and lymphocytes was analyzed and presented in comparison to historical blood values of normal, unmanipulated, age-matched cotton rats.

Serum total IgG ELISA. Ninety-six well plates were coated with 1:1,000 rabbit anti-cotton rat IgG in coating solution (KPL 50-84-00). Wells were subsequently blocked (KPL 50-61-00) and serum samples diluted 1:50,000 were loaded. Bound cotton rat IgG was detected with chicken anti-cotton rat IgG (1:15,000; Immunology Consultants Laboratory CCOT-25A), followed by HRP-labeled goat anti-chicken IgG (1:10,000; KPL). The amount of IgG in each serum sample was quantified with respect to the standard curve constructed of 10-fold dilution of normal cotton rat serum, with 1:100 dilution of serum assumed to have 10,000 Units of IgG.

RSV plaque assay. Lung homogenates were clarified by centrifugation and diluted 1:10 and 1:100 in EMEM. Confluent HEp-2 monolayers in 24-well plates were infected in duplicates with 50 µl of sample per well starting with undiluted (neat) samples followed by diluted homogenates. After one hour incubation at 37° C. in a 5% $CO_2$ incubator, wells were overlayed with 0.75% methylcellulose medium and plates restored into the 37° C. incubator. After 4 days of incubation the overlay was removed and the cells were fixed with 0.1% crystal violet stain for one hour, then rinsed and air-dried. Plaques were counted and viral titers were expressed as plaque forming units per gram of tissue. Viral titer for a group was calculated as the geometric mean+ standard error for all animals in that group at a given time. Student-t test was applied to determine significance of change in viral replication between vehicle-treated and test groups, with p<0.05 indicating a statistically-significant difference.

Real-time PCR. Total RNA was extracted from homogenized lung, kidney or liver tissue using the RNeasy purification kit (QIAGEN). One μg of total RNA was used to prepare cDNA using QuantiTect Reverse Transcription Kit (Qiagen). For the real-time PCR reactions the QuantiFast SYBR Green PCR Kit (Qiagen) was used in a final volume of 25 μl, with final primer concentrations of 0.5 μM. Reactions were set up in 96-well trays. Amplifications were performed on a Bio-Rad iCycler for 1 cycle of 95° C. for 3 min, followed by 40 cycles of 95° C. for 10 sec, 60° C. for 10 sec, and 72° C. for 15 sec. The baseline cycles and cycle threshold (Ct) were calculated by the iQ5 software in the PCR Base Line Subtracted Curve Fit mode. Relative quantification of DNA was applied to all samples. The standard curves were developed using serially-diluted cDNA sample most enriched in the transcript of interest (e.g., lungs from day 4 post-primary RSV infection). The Ct values were plotted against $\log_{10}$ cDNA dilution factor. These curves were used to convert the Ct values obtained for different samples to relative expression units. These relative expression units were then normalized to the level of ®-actin mRNA ("housekeeping gene") expressed in the corresponding sample. For animal studies, mRNA levels were expressed as the geometric mean±SEM for all animals in a group at a given time.

Results.

Figure 10A:
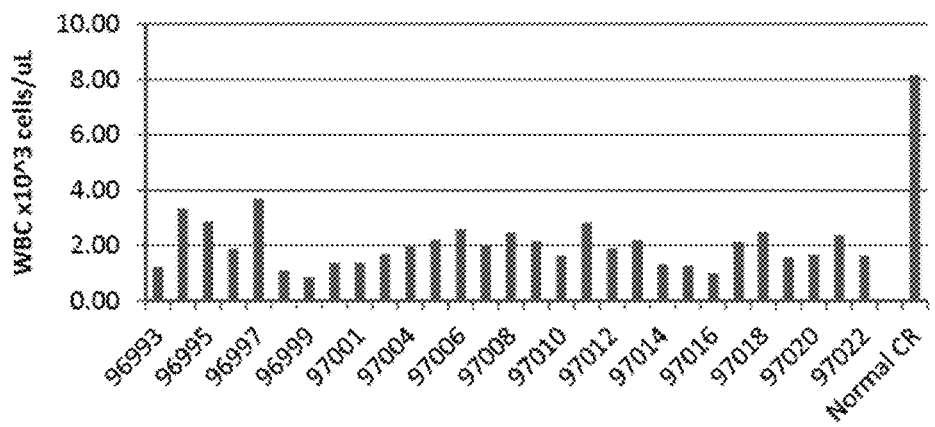
FIG. 10A through FIG. 10F show Total White Blood Cell counts and total Lymphocyte counts were reduced in all cyclophosphamide treated animals compared to normal, unmanipulated cotton rats.
Figure 10B:
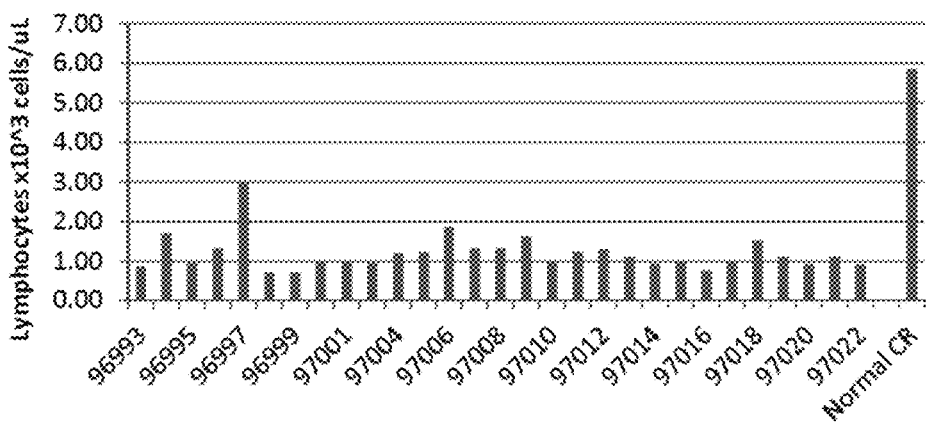
Figure 10C:
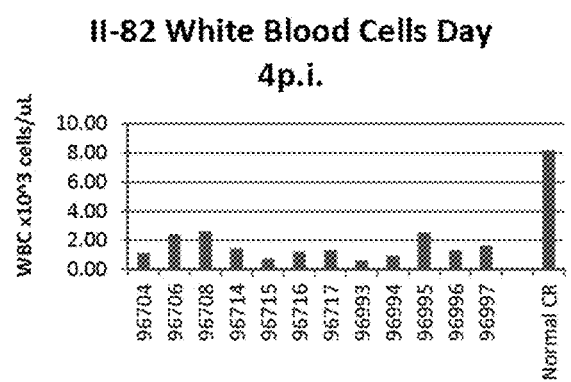
Figure 10D:
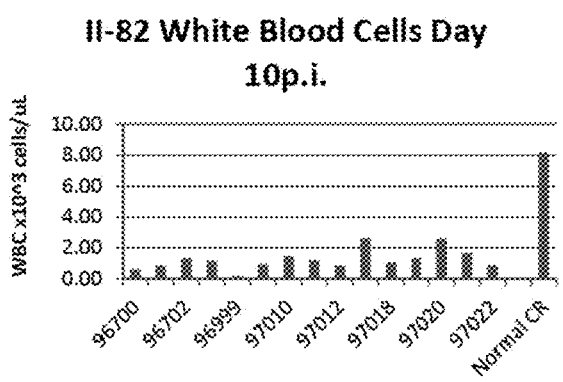
Figure 10E:
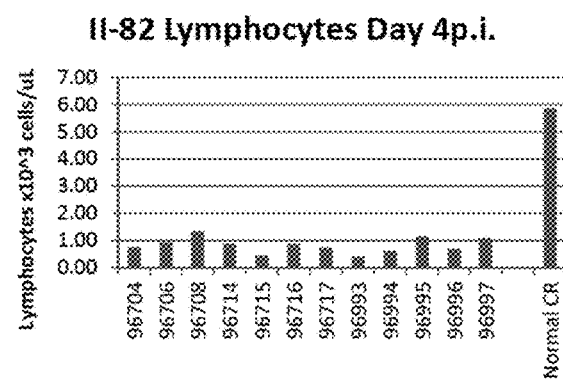
Figure 10F:
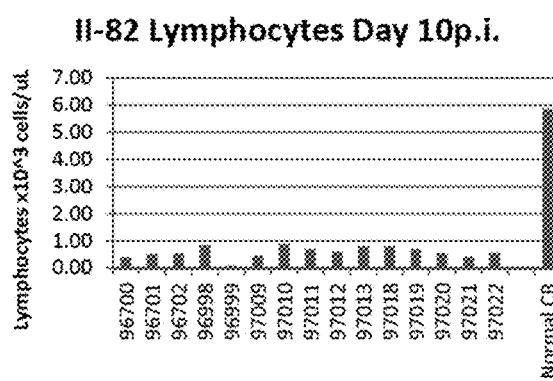

Whole Blood Assay. Total White Blood Cell counts and total Lymphocyte counts were reduced in all cyclophosphamide treated animals compared to normal, unmanipulated cotton rats (historical WBC and Lymphocyte count values for 6-8 week-old *S. hispidus* were used for comparison). This difference was seen in samples collected 18 days after the beginning of cyclophosphamide treatment (Day −3 with respect to RSV challenge, FIG. 10A), as well as in samples collected from animals sacrificed on Day 4 and Day 10 post-RSV-challenge (FIG. 10B).

Figure 11:
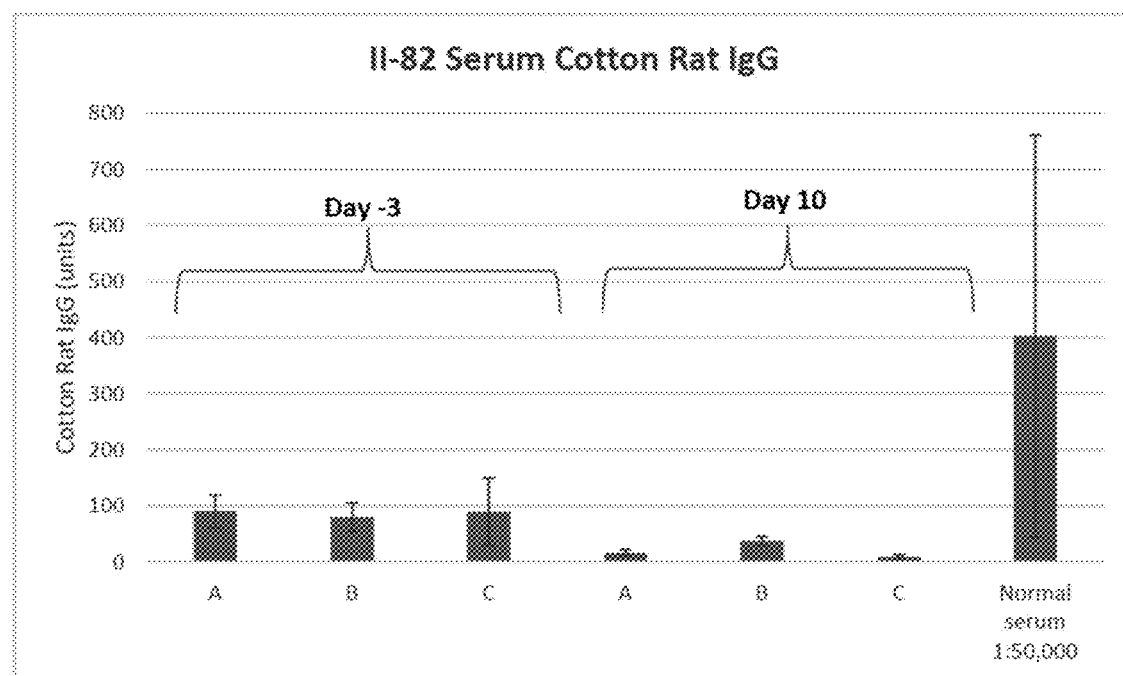
FIG. 11 shows the level of total IgG in the serum of cyclophosphamide-treated cotton rats was reduced compared to serum of control animals

Serum Total IgG ELISA. The level of total IgG in the serum of cyclophosphamide-treated cotton rats was reduced compared to serum of control animals (FIG. 11). The reduction was seen for serum collected on both days analyzed: 3 days prior to and 10 days after infection, which corresponds to days 18 and 31 after the beginning of cyclophosphamide treatments.

Figure 12:
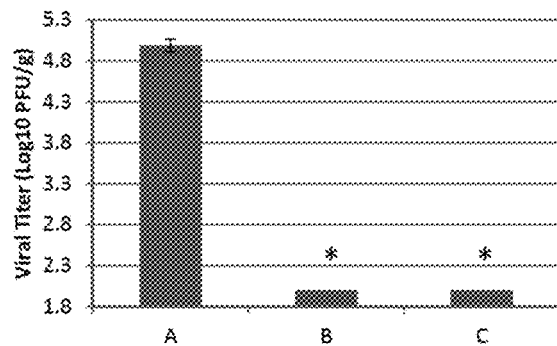
FIG. 12 shows viral titers from total lung homogenates measured on days 4 and 10 post-intranasal challenge with approximately 5.0 $Log_{10}$ of RSV/A/Long.
Figure 12:
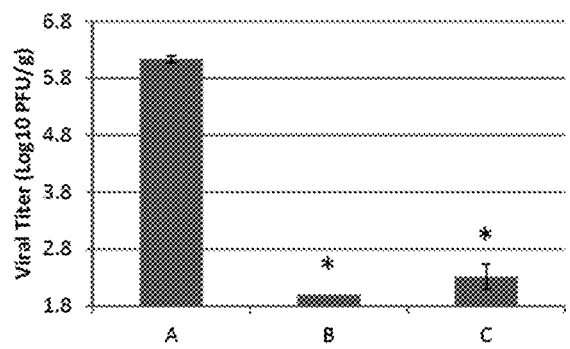

Lung RSV Titers. Viral titers from total lung homogenates were measured on days 4 and 10 post-intranasal challenge with approximately 5.0 $\text{Log}_{10}$ of RSV/A/Long. On day 4 post-infection 4.98 Log 10 PFU/g RSV was detected in the lungs of animals from Group A (FIG. 12). No virus was recovered from the lungs of animals in groups B and C. On day 10 post-infection, 6.14 Log 10 PFU/g RSV was detected in the lungs of animals from Group A. No virus was recovered from the lungs of animals in Group B, and in 3 out of 5 animals in group C.

Kidney and Liver RSV Titers. RSV infectious viral particles were quantified by plaque assay in the kidney and liver of one animal from Group A (animal #96998) and one animal from Group B (animal #97009). No virus was detected in either organ of either animal.

Figure 13:
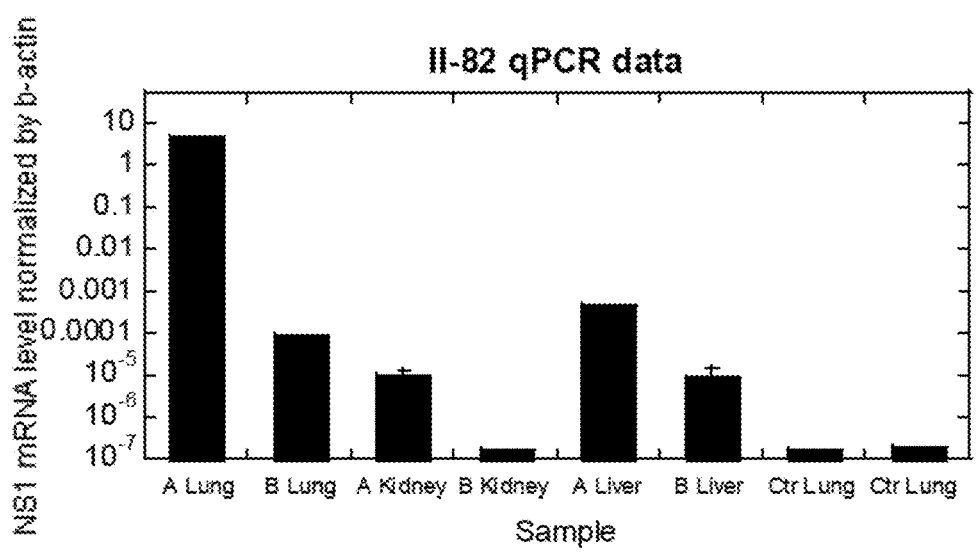
FIG. 13 shows RSV gene expression (NS1 mRNA) quantified by qPCR assay in the lung, kidney and liver of one animal from Group A (animal #96998) and one animal from Group B (animal #97009). NS1 mRNA expression was detected in all three organs collected from the animal in Group A, and in the lung and liver of animal in Group B.

RSV detection by qPCR. RSV gene expression (NS1 mRNA) was quantified by qPCR assay in the lung, kidney and liver of one animal from Group A (animal #96998) and one animal from Group B (animal #97009). NS1 mRNA expression was detected in all three organs collected from the animal in Group A, and in the lung and liver of animal in Group B (FIG. 13). For all three organs analyzed, RSV gene expression was higher in the animal in Group A animal compared to the animal in Group B.

Histopathology. Histopathology was analyzed in the lung, kidney and liver samples of one animal from Group A (animal #96998) and one animal from Group B (animal #97009). No significant differences were noted between the Group A and B kidney samples and between Group A and B liver samples analyzed. Pulmonary pathology in the Group A animal was stronger than in the Group B animal and was characterized by thickening and degeneration of bronchiolar epithelium, interstitial pneumonia, and mild alveolitis.

Immunosuppression was verified by significant decrease in whole blood cell and lymphocyte counts, and reduction in serum total IgG. Immunosuppressed animals treated with IVIG showed undetectable lung viral replication at day 4 p.i., and almost complete reduction in the prolonged viral replication caused by immunosuppression measured on day 10 (only two out of 5 animals in a group showed minimal viral replication). This reduction was accompanied by reduction in lung histopathology and decrease in the detection of viral RNA in lung, kidney, and liver samples of selected immunosuppressed animals.

Various modification, recombination, and variation of the described features and embodiments will be apparent to those skilled in the art without departing from the scope and spirit of the invention. Although specific embodiments have been described, it should be understood that the invention as claimed should not be unduly limited to such specific embodiments. Indeed, various modifications of the described modes and embodiments that are obvious to those skilled in the relevant fields are intended to be within the scope of the following claims. All publications and patents mentioned in the present application and/or listed below are herein incorporated by reference in their entireties.

What is claimed is:

1. A method of providing immunotherapy to a subject comprising administering to the subject an immunotherapeutic composition comprising:
   A) immune globulin prepared from a pooled plasma composition comprising plasma samples from 500 or more human plasma donors, wherein the pooled plasma composition has a final respiratory syncytial virus (RSV) neutralization titer of at least 1800, and an antibody titer for parainfluenza virus 1, parainfluenza virus 2, influenza A virus, and/or influenza B virus that is at least 1.3 times greater than the antibody titer in a control sample, wherein the control sample is a mixture of plasma samples obtained from 500 or more random human plasma donors, and wherein less than 50% of the donor plasma samples used for pooling are from donors with a RSV neutralization titer of at least 1800; and
   B) a pharmaceutically acceptable carrier;
   wherein the immunotherapeutic composition is intravenously administered in a single dose to provide between 250-2500 milligram (mg) immune globulin per kilogram (kg) to the subject.

2. The method of claim 1, wherein the immunotherapeutic composition is administered to the subject every three weeks.

3. The method of claim 1, wherein the immunotherapeutic composition is administered to the subject every four weeks.

4. The method of claim 1, wherein the subject is selected from the group consisting of an end stage renal disease (ESRD) patient, a patient on immunosuppressive therapy, an AIDS patient, a diabetic patient, a neonate, a transplant patient, a patient with malfunctioning immune system, an elderly person, a patient with autoimmune disease, a burn patient, a cancer patient, and a patient in an acute care setting.

5. The method of claim 4, wherein the subject is a patient on immunosuppressive therapy.

6. The method of claim 1, wherein the subject has a primary immunodeficiency disease (PIDD).

7. The method of claim 1, wherein the subject has an immunodeficiency.

8. The method of claim 1, wherein the immunotherapy is used to treat and/or prevent infection in the subject.

9. The method of claim 1, wherein the immunotherapy is used to treat a respiratory infection in the subject.

10. The method of claim 9, wherein the respiratory infection is an upper respiratory tract infection.

11. The method of claim 9, wherein the respiratory infection is a lower respiratory tract infection.

12. The method of claim 9, wherein the respiratory infection is caused by a pathogen selected from the group consisting of respiratory syncytial virus (RSV), parainfluenza virus, coronavirus, influenza virus, and metapneumovirus.

13. The method of claim 1, wherein the immunotherapy reduces viral load in the subject.

14. The method of claim 1, wherein the immunotherapy reduces the viral load in the lungs of the subject.

15. The method of claim 1, wherein the immunotherapy reduces the level of pathogenic viral RNA in an organ of the subject.

16. The method of claim 15, wherein the organ is selected from the lungs, liver and kidneys.

17. The method of claim 1, wherein the immune globulin is prepared from a pooled plasma composition comprising plasma samples from 1000 or more human plasma donors and wherein the control sample is a mixture of plasma samples obtained from 1000 or more random human plasma donors.

18. The method of claim 1, wherein the immunotherapeutic composition is intravenously administered in a single dose to provide 500 milligrams (mg) immune globulin per kilogram (kg) to the subject.

19. The method of claim 1, wherein the immunotherapeutic composition is intravenously administered in a single dose to provide 750 milligrams (mg) immune globulin per kilogram (kg) to the subject.

20. The method of claim 1, wherein the immunotherapeutic composition is intravenously administered in a single dose to provide 1500 milligrams (mg) immune globulin per kilogram (kg) to the subject.

* * * * *